US006426198B1

(12) United States Patent
Carstea et al.

(10) Patent No.: US 6,426,198 B1
(45) Date of Patent: Jul. 30, 2002

(54) GENES FOR NIEMANN-PICK TYPE C DISEASE

(75) Inventors: Eugene D. Carstea, Woburn, MA (US); Danilo A. Tagle, Gaithersburg, MD (US); Jill A. Morris, Chalfont, PA (US); Peter G. Pentchev, Kensington; William J. Pavan, Derwood, both of MD (US); Melissa A. Ashlock, Mont Vernon, NH (US); Stacie K. Loftus, Burtonsville, MD (US); Jessie Gu, Cambridge, MA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/462,136
(22) PCT Filed: Jul. 2, 1998
(86) PCT No.: PCT/US98/13862
§ 371 (c)(1),
(2), (4) Date: May 1, 2000
(87) PCT Pub. No.: WO99/01555
PCT Pub. Date: Jan. 14, 1999

Related U.S. Application Data

(60) Provisional application No. 60/051,682, filed on Jul. 3, 1997.

(51) Int. Cl.[7] .......................... C07K 1/00; C07H 21/04; C12N 1/20; C12P 21/06; G01N 33/566
(52) U.S. Cl. .......................... 435/69.1; 435/6; 435/7.2; 435/24.31; 435/7.21; 435/252.3; 435/320.1; 435/325; 530/350; 536/23.5; 436/501; 514/2
(58) Field of Search ........................ 530/350; 536/23.5; 435/6, 69.1, 7.1, 7.2, 252.3, 7.21, 320.1, 325, 24.31; 436/501; 514/2

(56) References Cited

U.S. PATENT DOCUMENTS 4,039,388 A    8/1977  Gal et al. ............. 195/103.5 R
5,859,328 A  * 1/1999  Nasrallah et al. ........... 800/205

FOREIGN PATENT DOCUMENTS

EP          0 520 843 A2   4/1992

OTHER PUBLICATIONS

Bowie et al., Science 247:1306–1310, 1990.*
Wells Biochemistry 29:8509–8517, 1990.*
Ngo et al., The Protein Folding Problem and Tertiary Structure, pp 492–495, 1994.*
Carstea et al., Science 227:228–231, 1997.*
Hillier et al., Accession No. W53013, sequence alignment, 1996.*
Marra et al., Accession No. W530720, sequence alignment, 1996.*
GenBank Accession No. H11606, 1995.*
GenBank Q67870, Mar. 23, 1995: sequence alignment.*
GenBank AA213311, Feb. 15, 2001: sequence alignment.*

"Genetic Diseases of Recognized Biochemical Abnormality," *Merritt's Textbook of Neurology*, Eight Edition, p. 508, 1989.
Brady et al, "Niemann–Pick Disease Types C and D," *Neurologic Clinics*, vol. 7, No. 1, p. 75–87, Feb. 1989.
"Nieman–Pick Disease," *Neurology in Clinical Practice*, vol. II, p. 1316, 1991.
Carstea et al., "Linkage of Niemann–Pick disease type C to human chromosome 18," *Proc. Natl. Acad. Sci. USA*, 90:2002–2004, Mar. 1993.
Carstea et al., "Localizing the human Nieman–Pick C gene to 18q11–12," *Am. J. Hum. Genet.*, vol. 55, No. 3, p. A182, Sep. 1994.
Vanier et al., "Genetic Hererogeneity in Niemann–Pick C Disease: A Study Using Somatic Cell Hybridization and Linkage Analysis," *Am. J. Hum. Genet.* 58: 118–125, 1996.
L. Hillier et al., "The WashU–Merck EST Project, zc02h09.r1 Soares parathyroid tumor NbHPA Homo sapiens cDNA clone 321185 5'," EMBL Database Entry HS013342, Accession No. W53013, XP002078611, Jun. 4, 1996.
M. Marra et al, "The Wash–HHMI Mouse EST project. Md15d07.r1 Soares mouse embryo NbME13.5 14.5 Mus musculus cDNA clone 368461 5'," EMBL Database Entry MM72024, Accession No. W53720, XP002078612, Jun. 6, 1996.
Gu et al., "Substantial narrowing of the Niemann–Pick C candidate interval by yeast artificial chromosome complementation," *Proc. Natl. Acad. Sci. USA*, 94:7378–7383, Jul. 1997.
Loftus et al., "Murine Model of Niemann–Pick C Disease: Mutation in a Cholesterol Homeostasis Gene," *Science*, 277:232–235, Jul. 11, 1997.
Carstea et al., "Niemann–Pick C1 Disease Gene: Homology to Mediators of Cholesterol Homeostasis," *Science*, 277:228–231, Jul. 11, 1997.
Carstea et al., "Newfound Gene Holds Key to Cell's Cholesterol Traffic," *Science*, 277:180–181, Jul. 11, 1997.
Miyawaki et al., Sphingomyelinosis, a New Mutation in the Mouse: A Model of Niemann–Pick Disease in Humans, *J. Hered.*, 73:257–263, 1982.
Morris et al., Lysosome Liquid Storage Disorder in NCTR–BALB/c Mice. I. Description of the Disease and Genetics, *Am. J. Pathol.*, 108:140–149, 1982.
Ohno et al., A Cell Line Derived from Sphingomyelinosis Mouse Shows Alterations in Intracellular Cholesterol Metabolism Similar to Those in Type C Nieman–Pick Disease, *Cell Structure & Function*, 17:229–235, 1992.
Sakiyama et al., A Lysosomal Storage Disorder in Mice: A Model of Niemann–Pick Disease, *J. Inherited Metab. Dis.*, 5:239–240, 1982.
Erickson et al., High Resolution Mapping of the spm (Niemann–Pick Type C) Locus on Mouse Chromosome 18, *Mamm. Genome*, 8(5):355–356, May 1997.

* cited by examiner

Primary Examiner—Yvonne Eyler
Assistant Examiner—Michael Brannock
(74) *Attorney, Agent, or Firm*—Klarquist Sparkman, LLP

(57) ABSTRACT

A gene for type C Niemann-Pick disease (NP-C) is disclosed, along with the amino acid sequence of the encoded peptide. Applications which are made possible by the present invention include detection of NP-C carriers and diagnosis of NP-C sufferers. The murine ortholog of the human gene is also disclosed.

13 Claims, 3 Drawing Sheets

```
              *                        **                                *        *        *        *
mNPC1    GYDLVQELCPGLFFDNVSLCCD  PHQSQFN-----TATEDY-----  QLQTLKSNLQLFLQOFLSRCPSCFYNLTLFCELTCS  105
hNPC1    GYDLVQELCPGLFFDNVSLCCD  PRQSQFN-----TATEDY-----  RLQTLKDNLQLFLQOFLSRCPSCFYNLNLFCELTCS  106
F02E8p   AYEKNVEFCPHLLTGDNKLCCT  PNQQDFNSTSEMKPIEKKEGF    SQAEGLTKQARHILGRCPSCFDNFAKLNCEFTCS  107
Lpa11p   TSKLVEWCGEEWKEVRYACCT   ADQGRFNMTKVEKS-------    KDNVALRDNLQKAQPLSSCPNCLKNFNNLFCHFTCA  173
                                                                                                  108

*                                            *        *
mNPC1    FDPKTPENKTNVKELEYYVGQSFANAMYNACRDVEAP   166
hNPC1    ----VDPVTNQKTNVKELQYYVGQSFANAMYNACRDVEAP   167
F02E8p   TPEYQPAEAYNTWEYRISTDFAEGMNSSCKDVTFG       162
Lpa11p   KEDKPIVAELDVFWNSSWASEFYDSCKNIKFS          173
```

GENES FOR NIEMANN-PICK TYPE C DISEASE

This application claims benefit of Provisional Appln. No. 60/051,682 filed Jul. 3, 1997.

FIELD OF THE INVENTION

This invention relates to nucleic acid sequences corresponding to the human gene for type C Niemann-Pick disease. The sequences are useful, among other applications, for the diagnosis of this disease. Also provided is the mouse homolog of this human gene.

BACKGROUND OF THE INVENTION

Niemann-Pick disease is the name given to a class of inherited lipid storage diseases. Four types of the disease are recognized, Types A, B, C and D. Niemann-Pick disease type C (NP-C) is an autosomal recessive neurovisceral lipid storage disorder which leads to systemic and neurological abnormalities (Brady et al., 1989). Clinical features of the disease include variable hepatosplenomegaly, vertical supranuclear ophthalmoplegia, progressive ataxia, dystonia and dementia (Pentchev et al., 1989). Cataplexy and seizures may occur later in the course of the illness. NP-C is characterized by phenotypic variability, with onset ranging from birth to early adulthood (Fink et al.. 1989). Type C Niemann-Pick disease differs from types A and B in that the latter two forms are lipidoses resulting from a lesion in the sphingomyelinase gene located on chromosome 11 (Pereira et al., 1991). In contrast, the underlying genetic defect of NP-C remains unknown. Type D Niemann-Pick disease (also known as the Nova Scotia variant) is allelic to type C and occurs in descendents of western Nova Scotians.

The biochemical hallmark of NP-C cells is the abnormal accumulation of unesterified cholesterol in lysosomes, which results in delayed homeostatic regulation of both uptake and esterification of low density lipoprotein (LDL) cholesterol (Sokol et al., 1988; Blanchette-Mackie et al., 1988; Pentchev et al., 1994; Pentchev et al., 1987). Accumulation of lysosomal cholesterol in the cells of NP-C sufferers can be detected cytochemically by the cholesterol-specific fluorescent dye, filipin. Normally, endocytosed LDL-derived cholesterol is mobilized from lysosomes to the endoplasmic reticulum for esterification. As a result, there is little free cholesterol accumulation in iysosomes detectable by filipin staining in normal cells. In contrast, in NP-C cells the lysosomal accumulation of the endocytosed LDL-derived free cholesterol results in a specific perinuclear filipin-staining pattern. Biochemically, the NP-C phenotype can most conviently be monitored by LDL-induced cholesterol ester synthesis. Cholesterol ester synthesis is markedly stimulated by LDL in normal cells, but not in NP-C cells.

Two independent murine models having autosomal recessive lysosomal storage defects have been described (Morris et al., 1982; Miyawaki et al., 1982; Sakiyama et al, 1982). The pathological features of these murine mutants are similar to human NP-C (Higashi et al., 1991; Ohno et al., 1992), but, to date, the genetic defect in these mouse lines remains uncharacterized.

If the gene underlying NP-C could be isolated, it could facilitate the detection, diagnosis, and perhaps treatment of the disease. It is the objective of this invention to provide a human cDNA corresponding to the gene for NP-C, as well as the cDNA underlying the NP-C murine models.

SUMMARY OF THE INVENTION

The present invention provides, for the first time, an isolated human nucleic acid molecule which is able to correct the cellular defect characteristic of Niemann-Pick type C disease. It is shown that NP-C patients carry mutations in the genomic copies of this nucleic acid. Orthologs of the disclosed nucleic acid molecule from other species are also provided.

More specifically, the invention provides an isolated human cDNA, herein referred to as the human NPC1 cDNA which, when transiently expressed in human cells derived from NP-C patients, is able to correct the abnormal lysosomal cholesterol accumulation that is characteristic of such cells. Also provided by this invention is the nucleotide sequence of this human cDNA molecule, as well as the nucleotide sequences of corresponding cDNAs from mouse, yeast and the worm C. elegans. The amino acid sequences of the proteins encoded by these cDNAs are also provided.

Having provided the nucleotide sequence of the human NPC1 cDNA (as well as the murine ortholog), correspondingly provided are the complementary DNA strands of these cDNA molecules and DNA molecules which hybridize under stringent conditions to these cDNA molecules or their complementary strands. Such hybridizing molecules include DNA molecules differing only by minor sequence changes, including nucleotide substitutions, deletions and additions. Also comprehended by this invention are isolated oligonucleotides comprising at least a segment of the disclosed cDNA molecules or the complementary strands of these molecules, such as oligonucleotides which may be employed as DNA hybridization probes or DNA primers useful in the polymerase chain reactiorn. Hybridizing DNA molecules and variants on the NPC1 cDNAs may readily be created by standard molecular biology techniques.

Through the manipulation of the nucleotide sequences provided by this invention by standard molecular biology techniques, variants of the NPC1 proteins may be made which differ in precise amino acid sequence from the disclosed proteins yet which maintain the basic functional characteristics of the disclosed NPC1 proteins or which are selected to differ in some characteristics from these proteins. Such variants are another aspect of the present invention.

Also provided by the present invention are recombinant DNA vectors comprising the disclosed DNA molecules, and transgenic host cells containing such recombinant vectors.

Having provided the isolated human NPC1 cDNA sequence and the orthologous murine cDNA, also comprehended by this invention are the genomic genes from which these cDNAs are derived.

The present invention also provides methods for using the disclosed cDNAs, the corresponding genomic gene and derivatives thereof, and of the protein, and derivatives thereof, in aspects of diagnosis of NP-C and detection of NP-C carriers. One particular embodiment of the present invention is a method for screening a subject to determine if said subject carries a mutant NPC1 gene. The method comprises detecting the presence of nucleotide differences between the sequence of the subject's NPC1 gene ORF compared to the NPC1 cDNA sequence disclosed herein, and determining whether any such sequence differences will result in the expression of an aberrant NPC1 gene product in the subject. The step of detecting nucleic acid sequence differences may be performed using several techniques including: hybridization with oligonucleotides (including, for example, the use of high-density oligonucleotide arrays); PCR amplification of the NPC1 gene or a part thereof using oligonucleotide primers; RT-PCR amplification of the NPC1 RNA or a part thereof using oligonucleotide primers, and direct sequencing of the NPC1 gene of the subject's genome using oligonucleotide primers.

The disclosed sequences will also be useful in the creation and study of mutants in the NPC1 locus, which in turn may yield valuable information about the biochemical pathways underlying the disease, as well as information about cholesterol metabolism.

A further aspect to the present invention is a preparation comprising specific binding agents, such as antibodies, that specifically detect the NPC1 protein. Such specific binding agents may be used in methods for screening a subject to assay for the presence of a mutant NPC1 gene. One exemplary method comprises providing a biological sample of the subject which sample contains cellular proteins and providing an immunoassay for quantitating the level of NPC1 protein in the biological sample.

The foregoing and other features and advantages of the invention will become more apparent from the following detailed description and accompanying drawings. Those skilled in the art will appreciate that the utility of this invention is not limited to the specific experimental modes and materials described herein.

BRIEF DESCRIPTION OF DRAWINGS

FIG. 3 is a schematic comparison of the NPC domain in the orthologous sequences from human (residues 55 to 166 of SEQ ID NO: 2), mouse (residues 97 to 208 of SEQ ID NO: 4), yeast (residues 56 to 162 of SEQ ID NO: 6) and *C. elegans* (residues 57 to 173 of SEQ ID NO: 9). Identical residues in at least 2 of the 4 sequences are highlighted in black. Similar residues are shaded in gray. The NPC domain represents region of high sequence conservation in addition to the transmembrane domains and sterol-sensing domains. No structural or motif similarity in the database has been attributed to this region. Conserved cysteines are indicated by asterisks.

SEQUENCE LISTING

Figure 1:
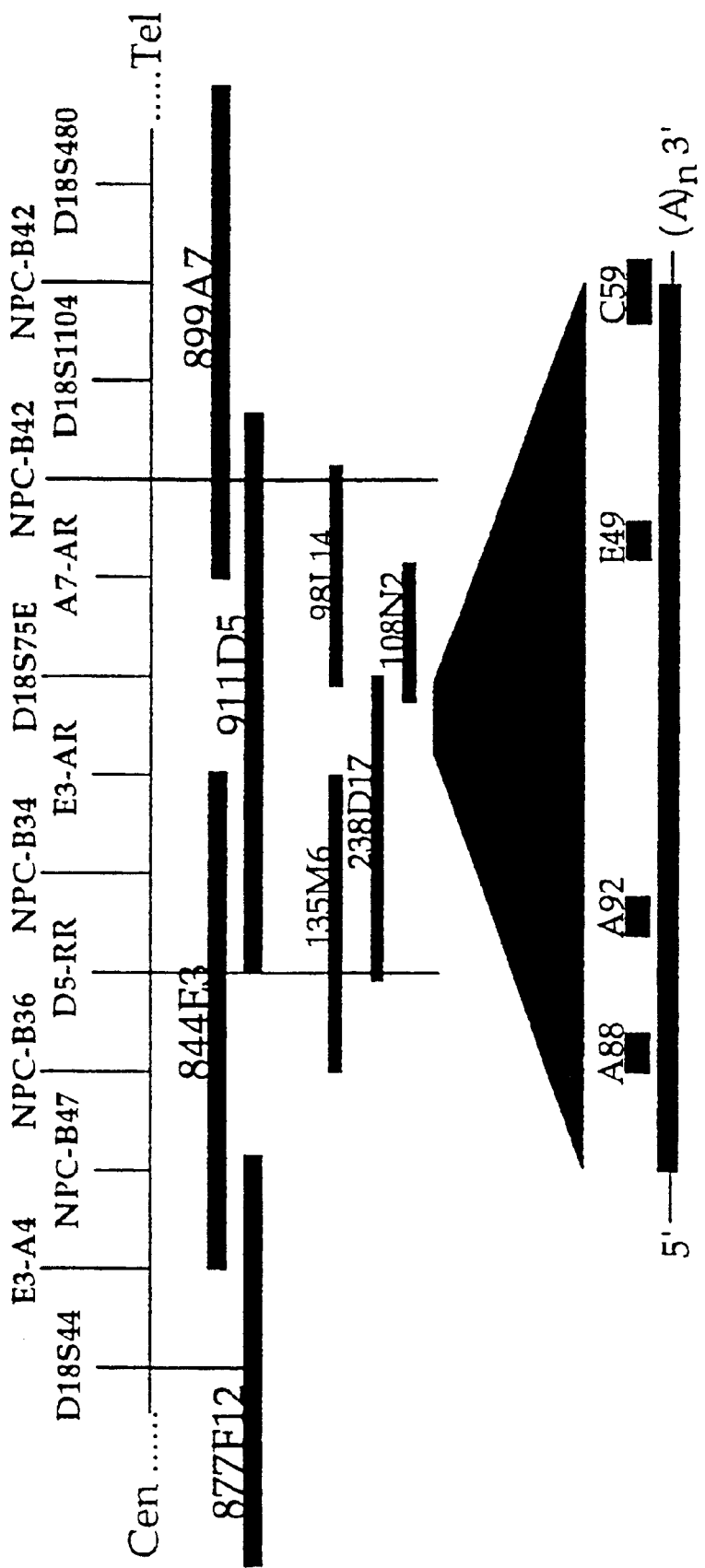
FIG. 1 shows, schematically, the cloning of the hNPC1 cDNA. (i) The 1 cM genetic interval, covering a physical distance of ~1500 Kb, is defined by microsatellite markers D18S44 and D18S1388. It is represented schematically by equally spaced loci and not drawn to scale. (ii) Complementation with YAC 911_D_5 (hatched) refined the interval to a region between D18S1382 and D18S1388. BACs were assembled across the NPC interval and used to generate genomic subclones for exon trapping. (iii) Of the resultant trapped inserts, 4 of the verified exons, A88, A92, E49, and C59 mapped to NPC1. (iv) The 4673 bp cDNA is represented by an ORF of 3834 bp, and a 713 bp 3' UTR.
Figure 2:
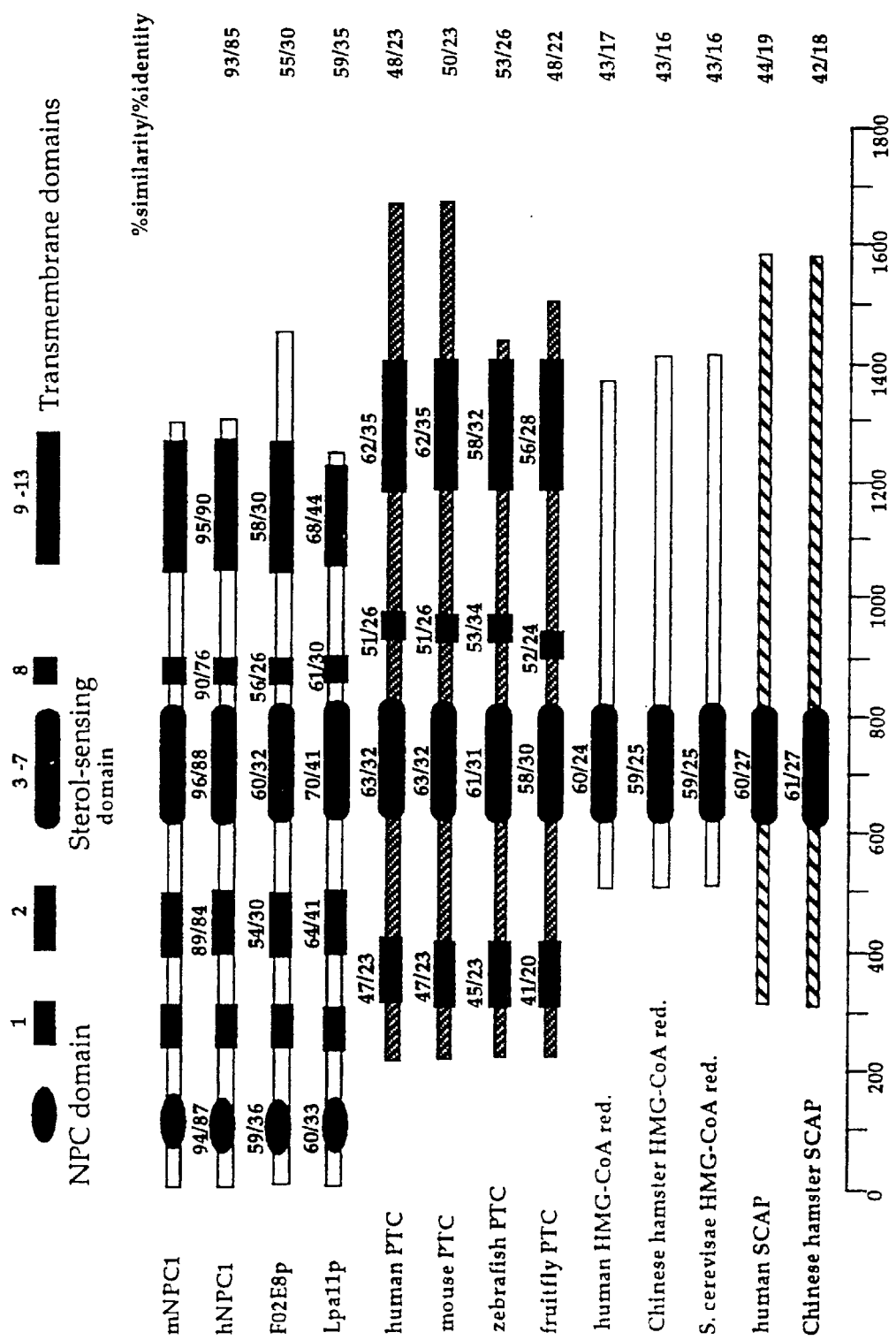
FIG. 2 is a schematic representation of comparisons between orthologs from NPC1, PTC, HMG-CoA and SCAP proteins. NPC1 sequences are from mouse (mNPC1), human (hNPC1), *C. elegans* (FO2E8p; Genbank #U53340), *S. cerevisiae* (Lpal lp; Genbank #U33335); Patched sequences are from human PTC (Genbank #U59464), mouse PTC (Genbank #U46155), zebrafish PTC (Genbank #X98883), fruitfly PTC (Genbank #M28999); HMG-CoA sequences are from human HMG-CoA (Genbank #M11058), Chinese hamster HMG-CoA (Genbank #L00183), *S. cerevisiae* HMG-CoA (Genbank #M22002); and SCAP sequence from Chinese hamster (SCAP; Genbank #U67060). Blocks of homologies were identified using MACAW. Pairwise comparisons in relation to mNPC1 using entire protein sequences (values shown in the rightmost column) or within domains (as indicated over the shapes designating each domain) were performed using GCG software package. Transmembrane homologies are relative to the twelve putative transmembrane domains of human PTC.

The sequence listing appended hereto includes 8 sequences, as follows:

Seq. I.D. No. 1 shows the nucleotide sequence of the human NPC1 cDNA.

Seq. I.D. No. 2 shows the amino acid sequence of the human NPC1 peptide.

Seq. I.D. No. 3 shows the nucleotide sequence of the murine NPC1 cDNA.

Seq. I.D. No. 4 shows the amino acid sequence of the murine NPC1 peptide.

Seq. I.D. No. 5 shows the nucleotide sequence of the yeast (*Saccharomyces cerevisiae*) NPC1 ortholog.

Seq. I.D. No. 6 shows the amino acid sequence of the *S. cerevisiae* NPC1 ortholog peptide.

Seq. I.D. No. 7 shows the nucleotide sequence of the *Caenorhabditis elegans* genomic NPC1 ortholog.

Seq. I.D. No. 8 shows the nucleotide sequence of the putative cDNA corresponding to the *Caenorhabditis elegans* NPC1 ortholog.

Seq. I.D. No. 9 shows the amino acid sequence of the *C. elegans* NPC1 ortholog peptide.

Seq. I.D. Nos. 10 and 11 show primers that may be used to amplify the ORF of the human NPC1 cDNA.

Seq. I.D. Nos. 12 and 13 show primers that may be used to amplify the ORF of the murine NPC1 cDNA.

Definitions

In order to facilitate review of the various embodiments of the invention, the following definitions of terms and explanations of abbreviations are provided:

NP-C: Niemann-Pick type C disease.

NPC1 gene: A gene, the mutant forms of which are associated with Neimann-Pick type C disease. Herein, the human and murine, NPC1 genes are primarily discussed. For convenience, the human gene is referred to as hNPC1 and the murine gene as mNPC1 (this same nomenclature is also used to distinguish between the human and murine cDNAs and proteins). Where no "h" or "m" designation is given, reference to the NPC1 gene generally is intended, i.e., not limited to any particular species (orthologous sequences from yeast and *C. elegans* are also presented herein). The definition of an NPC1 gene includes the various sequence polymorphisms that exist in the species in question.

NPC1 cDNA: The NPC1 cDNA is functionally defined as a cDNA molecule which, when transfected into NP-C cells (such that the NPC1 protein encoded by the cDNA is expressed), is able to restore the normal phenotype by correcting the abnormal accumulation of LDL-derived cholesterol in the lysosomes. This may conveniently be determined cytochemically by the filipin staining assay or biochemically by the LDL-induced cholesterol ester synthesis assay, both of which are described in detail below. The NPC1 cDNA is derived by reverse transcription from the mRNA encoded by the NPC1 gene and lacks internal non-coding segments and transcription regulatory sequences found in the NPC1 gene.

NPC1 protein: the protein encoded by an NPC1 gene or cDNA. This protein may be functionally characterized by its ability, when expressed in NP-C cells, to correct the lysosomal cholesterol accumulation phenotype that is characteristic of such cells. Thus, "NPC1 protein biological activity" refers to the ability of a protein to correct the lysosomal cholesterol accumulation phenotype that is characteristic of NP-C cells.

NP-C sufferer or NP-C homozygote: a person who carries a mutant NPC1 gene on each copy of chromosome 18, such that the person exhibits clinical symptoms of Niemann-Pick type C disease.

NP-C carrier or NP-C heterozygote: a person who does not exhibit clinical symptoms of NP-C but who carries one mutant form of the NPC1 gene and may transmit this mutant gene to progeny.

Mutant NPC1 gene: a form of the NPC1 gene that does not encode a functional NPC1 protein and which is associated with Niemann-Pick type C disease. Functionally, transfection of a mutant NPC1 gene or cDNA into NP-C cells does not correct the aberrant cholesterol accumulation phenotype of such cells.

Isolated: An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

cDNA (complementary DNA): a piece of DNA lacking internal, non-coding segments (introns) and regulatory sequences which determine transcription. cDNA is synthesized in the laboratory by reverse transcription from messenger RNA extracted from cells.

ORF (open reading frame): a series of nucleotide triplets (codons) coding for amino acids without any termination codons. These sequences are usually translatable into a peptide.

Ortholog: two nucleotide sequences are orthologs of each other if they share a common ancestral sequence and diverged when a species carrying that ancestral sequence split into two species. Ortholgous sequences are also homologous sequences.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, ©1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the human NPC1 cDNA or gene will anneal to a-target sequence such as an NPC1 gene homolog from rat contained within a genomic rat genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the NPC1 cDNA or gene sequences.

The invention thus includes isolated nucleic acid molecules that comprise specified lengths of the disclosed NPC1 cDNA or gene sequences. Such molecules may comprise at least 20, 25, 30, 35, 40 or 50 consecutive nucleotides of these sequences and may be obtained from any region of the disclosed sequences. By way of example, the mouse and human cDNA and gene sequences may be apportioned into halves or quarters based on sequence length, and the isolated nucleic acid molecules may be derived from the first or second halves of the molecules, or any of the four quarters. The mouse cDNA, shown in Seq. I.D. No. 3 may be used to illustrate this. The mouse cDNA is 5029 nucleotides in length and so may be hypothetically divided into halves (nucleotides 1–2515 and 2516–5029) or quarters (nucleotides 1–1257, 1258–2515, 2516–3773 and 3774–5029). Nucleic acid molecules may be selected that comprise at least 20, 25,30, 35, 40 or 50 consecutive nucleotides of any of these portions of the mouse cDNA. Thus, one such nucleic acid molecule might comprise at least 25 consecutive nucleotides of the region comprising nucleotides 1–1257 of the disclosed mouse cDNA. Similarly, the human cDNA shown in Seq. I.D. No. 1 may be divided into halves (nucleotides 1–2275 and 2276–4550) or quarters (nucleotides 1–1137, 1138–2275, 2276–3413 and 3414–4550) and nucleic acid molecules comprising specified lengths of consecutive nucleotides may be selected from any one of these regions.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Purified: the term purified does not require absolute purity; rather, it is intended as a relative term. Thus, for example, a purified NPC1 protein preparation is one in which the NPC1 protein is more pure than the protein in its natural environment within a cell. Preferably, a preparation of an NPC1 protein is purified such that the NPC1 protein represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: the similarity between two nucleic acid sequences, or two amino acid sequences is expressed in terms of the similarity between the sequences, otherwise referred to as sequence identity. Sequence identity is frequently measured in terms of percentage identity (or similarity or homlogy); the higher the percentage, the more similar the two sequences are. Homologs of the human and mouse NCP1 proteins will possess a relatively high degree of sequence identity when aligned using standard methods.

Methods of alignment of sequences for comparison are well-known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI online site under the "BLAST" heading. A description of how to determine sequence identity using this program is available at the NCBI online site under the "BLAST overview" subheading.

Homologs of the disclosed NCP1 proteins are typically characterized by possession of at least 70% sequence identity counted over the full length alignment with the disclosed amino acid sequence of either the human or mouse NPC1 amino acid sequences using the NCBI Blast 2.0, gapped blastp set to default parameters. Proteins with even greater similarity to the reference sequences will show increasing percentage identities when assessed by this method, such as at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the NCBI online site under the "Frequently Asked Questions" subheading. One of skill in the art will appreciate that these sequence identity ranges are provided for guidance only; it is entirely possible that strongly significant homologs could be obtained that fall outside of the ranges provided. The present invention provides not only the peptide homologs are described above, but also nucleic acid molecules that encode such homologs.

One indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (1993), and are discussed in more detail below.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequence that all encode substantially the same protein.

Specific binding agent: An agent that binds substantially only to a defined target. Thus a NPC1 protein specific binding agent binds substantially only the NPC1 protein. As used herein, the term "NPC1 protein specific binding agent" includes anti-NPC1 protein antibodies and other agents that bind substantially only to the NPC1 protein.

The term "anti-NPC1 protein antibodies" encompasses monoclonal and polyclonal antibodies that are specific for the NPC1 protein, i.e., which bind substantially only to the NPC1 protein when assessed using the methods described below, as well as immunologically effective portions ("fragments") thereof. The anti-NPC1 protein antibodies used in the present invention may be monoclonal antibodies (or immunologically effective portions thereof) and may also be humanized monoclonal antibodies (or immunologically effective portions thereof). Immunologically effective portions of monoclonal antibodies include Fab, Fab', F(ab')$_2$ Fabc and Fv portions (for a review, see Better and Horowitz, 1989). Anti-NPC1 protein antibodies may also be produced using standard procedures described in a number of texts, including Harlow and Lane (1 988).

The determination that a particular agent binds substantially only to the NPC1 protein may readily be made by using or adapting routine procedures. One suitable in vitro assay makes use of the Western blotting procedure (described in many standard texts, including Harlow and Lane (1988)). Western blotting may be used to determine that a given NPC1 protein binding agent, such as an anti-NPC1 protein monoclonal antibody, binds substantially only to the NPC1 protein.

Mammal: This term includes both human and non-human mammals. Similarly, the term "patient" includes both human and veterinary subjects.

Additional definitions of terms commonly used in molecular genetics can be found in Benjamin Lewin, Genes V published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

DETAILED DESCRIPTION OF THE INVENTION

This invention provides the nucleotide sequence of the human Niemann-Pick type C cDNA. This human cDNA sequence, which is depicted in Seq. I.D. No. 1, is herein referred to as the human NPC1 or hNPC1 cDNA. The hNPC1 cDNA encodes a protein which is herein referred to as the human NPC1 or hNPC1 protein. The amino acid sequence of the hNPC1 protein is also part of this invention and is depicted in Seq. I.D. No. 2.

Mutations in the gene corresponding to the HNPC1 cDNA can give rise to defective forms of the hNPC1 protein. Defective forms of the protein (i.e., those which cannot fully perform the functions of the normal hNPC1 protein) underly the NP-C disease condition. Because NP-C disease is a recessive condition, only those individuals in which both copies of the hNPC1 gene are mutated manifest the clinical symptoms of NP-C. Individuals who carry just one mutated hNPC1 gene do not manifest these clinical symptoms, but are carriers of the disease. The provision of the hNPC1 cDNA sequence now enables methods of detecting the presence of mutations in the gene corresponding to the hNPC1 cDNA, and thereby facilitates the determination of whether an individual is an NP-C sufferer, an NP-C carrier or is "healthy" with respect to NP-C. Methods by which the NP-C status of an individual can be determined are also encompassed by this invention.

This invention also includes a murine cDNA, an ortholog of the hNPC1 cDNA, which is demonstrated to underly the biochemical and histopathological defects in the two mouse models of NP-C. The murine cDNA sequence, herein referred to as the murine NPC1 or mNPC1, is shown in Seq. I.D. No. 3 and the amino acid sequence of the encoded protein (the murine NPC1 or mNPC1 protein) is shown in Seq. I.D. No. 4. The provision of the murine sequences will greatly facilitate the study of type C Niemann-Pick disease through the murine disease model. Additionally, orthologous cDNA sequences from *Saccharomyces cerevisiae* and *Caenorhabditis elegans* are presented in Seq. I.D. Nos. 5 and 7, respectively, and the amino acid sequences of the proteins encoded by these cDNAs are presented in Seq. I.D. Nos. 6 and 8, respectively. These and the human and murine sequences will be useful in the creation and study of additional models for NP-C, as well as for the study of cholesterol metabolism, signal transduction, neurodegeneration, apoptosis and neurobiology in general.

Following a description of materials and methods for use in conjunction with this invention, sections describing the isolation and characterization of the human and murine NPC1 cDNAs as well as preferred methods for making these sequences are presented. Also presented are methods for expressing the human and murine NPC1 proteins, methods for producing specific binding agents, such as antibodies, that specifically bind to these proteins, and methods for producing sequence variants. In addition, methods for using the sequence information to detect the presence of mutant NPC1 genes in human subjects are described, as are methods of using specific binding agents to detect levels of NPC1 protein in body tissues.

1. Materials and Methods
   a. General Molecular Biology Methods

Standard molecular biology, biochemistry and immunology methods are used in the present invention unless otherwise described. Such standard methods are described in Sambrook et al. (1989), Ausubel et al (1987) and Harlow and Lane (1988).

Oligonucleotides can be chemically synthesized using standard methods such as the phosphoramidite triester method (Beaucage et al., 1981) on commercially available automated oligonucleotide synthesizers (available from, e.g., Applied Biosystems, Foster City, Calif.).

The nucleotide sequences of cloned NPC1 cDNAs and genes can be verified using standard DNA sequencing techniques such as the di-deoxy sequencing method described by Sanger et al. (1977).

b. Cell Culture Methods

Cell lines were grown as monolayers in tissue culture flasks or dishes. The CHO cell mutant CT60 and its variant CT60 neo$^R$ HAT$^S$ were provided by Dr. T. Y. Chang (Dartmouth College of Medicine, Hanover, N.H.) and grown in CT60 medium: HAM's F-12 (F-1 2) medium (Biofluids, Inc., Rockville, Md.) supplemented with 10% fetal bovine serum (FBS, Hyclone Laboratories, Inc., Logan, Utah), 2 mM glutamine, 100 units/ml penicillin, and 100 ug/ml streptomycin. The mouse ovarian granulosa cell lines, ELN and ELC, obtained from normal and NP-C BALB/c mice, respectively, by SV-40 transformation (Amsterdam et al., 1992) were grown in a 1:1 mixture of F-12 and Dulbecco's modified Eagle's medium (DMEM) supplemented with 5% FBS and the above reagents. Yeast spheroplast fusion clones derived from CT60 cells were selected and maintained in CT60 medium as described above, plus 400 ug/ml G-4 18 (Gibco BRL). CT60-ELN/ELC cell fusion clones were selected and propagated in the same medium plus 1×HAT ($10^{-4}$M hypoxanthine, $4\times10^{-7}$ M aminopterin, $1.6\times10^{-5}$M thymidine). Normal human fibroblasts (derived from normal volunteers of the Developmental and Metabolic Neurology Branch, NRNDS, NIH, under guidelines approved by NIH clinical research committees) and NP-C human fibrobfasts (3123; NIGMS Human Genetic Mutant Cell Repository, Coriell Institute for Medical Research, Camden, N.J.) were propagated in DMEM supplemented with 10% FBS.

c. Yeast Spheroplast Fusion

All YACs used for spheroplast fusions were modified with a gene conferring resistance to neomycin by homologous recombination using the pRAN4 vector as described by Srivastava et al. (1991). Yeast spheroplasts were prepared and fused to recipient cells and clones were derived as described by Mogayzel et al. (1997) and Huxley et al. (1991).

d. Fiiipin Staining

Cells were stained with filipin and viewed by fluorescence microscopy according to Kruth and Vaughan (1980) and Pentchev et al. (1985), with the following modifications. Cells were plated in 2-well chamber slides (Nunc, Inc., Naperville, Ill.) in F-12 media supplemented with 5% lipoprotein-depleted serum (LPDS, Perimmune, Inc., Rockville, Md.) for two to three days before human LDL (PerImmune, Inc.) was added (50 mg/ml). After overnight incubation in the presence of LDL, the cells were washed three times with PBS and fixed with 3% paraformaldehyde in PBS for 30 min. The fixed cells were then washed in PBS (5 min×3), quenched with glycine (1.5 mg/ml in PBS; 10 min) and 2 ml of fresh filipin (Sigma) solution (0.05 mg/ml in PBS) were added to each slide (30 min). Slides were rinsed with PBS, gaskets were removed, a drop of phenylenediamine/glycerol was added, and slides were mounted with coverslips.

Fluorescence signals were detected using a Zeiss Axiovert 405M microscope (Carl Zeiss, Thomwood, N.Y.) equipped with a filter for observation at the appropriate wavelengths: 365 nm excitation and 395 nm emission. Photographs were obtained using 4 second exposures at a magnification of 320×.

e. Lipid Analysis

When LDL is endocytosed and hydrolyzed into free cholesterol in lysosomes, cholesterol ester synthesis is activated by the increase in the free cholesterol pool. This reaction may be monitored in vitro by the incorporation of exogenously derived [$^3$H] oleic acid into cholesterol [$^3$H] oleate.

The amount of radioactive tracer [$^3$H] oleic acid (DuPont, New England Nuclear; specific activity of 200,000 dpm/nmol) incorporation into cholesterol ester and triglyceride was measured by thin layer chromatography as described by Pentchev et al. (1985; 1986), with the following modifications. Cells were seeded in 6-well plates and incubated with [$^3$H] oleic acid (100 mM) and human LDL (50 mg/ml). After 18 hr incubation, lipids and proteins were extracted. Non-radioactive cholesterol oleate and triolein were added to the lipid extract before thin layer chromatography was performed. Proteins were assayed by the Lowry method (Lowry et al., 1951). The amount of cholesterol oleate was normalized to the amount of protein (in mg) and compared in the presence or absence of LDL (D cholesterol [$^3$H] oleate synthesis). The D was compared to controls using a non-paired, two-tailed T-test.

f. Northern Blot Analysis

RNA was extracted from cell monolayers using TRIZOL (GibcoBRL), following the product instructions. For each RNA sample, 10 ug were loaded on a 1.2% agarose/formaldehyde gel. Northern blotting and hybridization were performed as described by Mogayzel et al. (1997). Probes were labeled by random oligo extension (Ready-To-Go kit, Pharmacia Biotech, Piscataway, N.J.), following the kit instructions. After a 10 min denaturation, repeated sequences were blocked by incubating the probe with unlabeled human placental and Cot-1 DNA at 65 ° C. for 30 min.

g. Cell Fusions

Cell fusions were performed using polyethylene glycol (PEG) according to Davison et al. (1976), with the following modifications: CT60 neo$^R$ HAT$^S$ and ELN or ELC cells were seeded as a mixture (1:1 ratio) at 1.4×10$^6$ cells/100 mm dish and grown in CT60 medium at 37° C. overnight. Cells were washed with PBS, treated with the dropwise addition of 4 ml F-12 medium containing 40% polyethylene glycol (PEG 1500, Boehringer Mannheim) and 5% dimethyl sulfoxide and incubated at room temperature for 2 min. Plates were washed twice with CT60 medium and incubated in the same media for 24 hr. Cells from each fusion were trypsinized and seeded onto three 100 mm plates, cultured for two more days and then switched to double selection media consisting of F-12/10% FBS with 400 ug/ml G418 and 1×HAT. Clones were isolated and expanded prior to analysis.

h. DNA Preparation for STS Content Analysis

Cell hybridization and yeast spheroplast fusion derived clones were frozen at 333 10$^6$ cells per ml in microcentrifuge tubes. For DNA lysates, each tube was thawed, cells were pelleted, washed once with PBS and resuspended in 50 ul of lysis buffer (1×Taq buffer, Perkin Elmer), 0.05 mg/ml Proteinase K, 20 mM DTT, and 0.5 ug/ml sarkosyl). The suspension was incubation overnight at 37° C., boiled for 15 minutes, then pelleted at 13,000 rpm for 5 minutes. An aliquot of the supernatant was used for PCR using primers D18Mit64 and D18Mit146 (MIT Database) and an annealing temperature of 55° C.

2. Location of Human Gene for NPC on Yeast Artificial Chromosome

Efforts to isolate a gene responsible for NP-C using positional cloning have established an NP-C critical interval of 1 centiMorgan on human chromosome 18, flanked by the markers D18S44 and NPC-B42. In addition, there are two independent murine mutants with an autosomal recessive lysosomal cholesterol storage defect (Morris et al., 1982; Miyawaki et al. 1982; Sakiyama et al., 1982). The pathological features of these murine mutants are similar to human NP-C. Linkage analysis using one of these mutant strains (an inbred C56BL/KsJ sphingomyelinosis strain) placed the NP-C locus near the glucocorticoid receptor-1 gene on mouse chromosome 18. Restoration of the normal intracellular distribution and esterification of exogenous cholesterol was achieved when human chromosome 18, a chromosome partly syntenic to mouse chromosome 18 (McKusick, 1990), was transferred into an immortalized cell line derived from this strain (SPM-3T3 cells) (Kurimasa et al., 1993). Genetic cross breeding studies suggested that the gene responsible for NP-C in the C56BL/KsJ sphingomyelinosis mice was the same gene mutated in the other strain (NP-C BALB/c) (Yamamoto et al., 1994), while cell fusiori studies with an SV40-transformed ovarian granulosa cell line (Amsterdam et al., 1992) derived from the NP-C BALB/c mice suggested that these mice were genotypically allelic to human NP-C linked to chromosome 18. These data were consistent with the linkage of human NP-C to chromosome 18q11-12 and strongly suggested that murine and human NP-C are caused by mutations in the same gene.

In addition to the human and mouse NP-C phenotypes, a Chinese hamster ovary (CHO) cell line which exhibits the NP-C phenotype (CT60) has also been described (Cadigan et al., 1990). This cell line was generated from normal CHO cells using chemical mutagenesis, and was selected based on its cholesterol metabolism profile. The CT60 cell line displays sequestration of unesterfied cholesterol in the acidic compartment of the lysosomal/endosomal fraction and markedly reduced activation of cholesterol ester synthesis by LDL. Thus, it appears that CT60 has a remarkable phenotypic resemblance to human and mouse NP-C, and that the basic defect is in translocation of lysosomal LDL-derived cholesterol to the endoplasmic reticulum for esterification. Although these cells remained to be confirmed genotypically, the data support CT60 as a potential CHO counterpart of NP-C.

a. Formation of Heterokaryons between CT60 Cells and Normal or NP-C Mouse Ovarian Cells To assess whether the CHO mutant CT60 is genotypically allelic to mouse NP-C, cell fusion studies were performed. A CT60 variant which is resistant to neomycin (neo$^R$) and sensitive to hypoxanthine, aminopterin, and thymidine (HAT) (CT60 neo$^R$ HAT$^S$; T. Y. Chang, personal communication) was fused to SV40 transformed mouse ovarian granulosa cell lines, ELN or ELC, derived from normal or NP-C BALB/c mice, respectively. It was hypothesized that if the mutation causing the NP-C-like phenotype in CT60 cells was allelic to the gene responsible for murine NP-C, heterokaryons of CT60 neo$^R$ HAT$^S$ and mouse cells would show phenotypic correction with ELN, but not with ELC cells. After two weeks of neo/HAT double selection, clones were isolated and expanded. Six clones each were successfully propagated from fusions performed with CT60 neo$^R$ HAT$^S$ and either ELN or ELC cells and characterized for retention of the gene responsible for murine NP-C on mouse chromosome 18 by polymerase chain reaction (PCR) using two polymorphic sequence-tagged-site (STS) markers unique to the mouse NP-C interval, D18Mit64 proximal to, and D18Mit146 distal to, the gene responsible for murine NP-C. These two markers were present in all six CT60 neo$^R$ HAT$^S$-ELN fusion clones and all six CT60 neo$^R$ HAT$^S$-ELC fusion clones; but not in the parental cell line CT60 neo$^R$ HAT$^S$, suggesting that the heterokaryons retained at least one copy of the gene responsible for murine NP-C on chromosome 18.

b. Complementation of CT60 Cells by Normal Mouse Ovarian Cells

ELN and ELC derived CT60 neo$^R$ HAT$^S$ heterokaryon clones were evaluated for normalization of the NP-C phenotype by filipin staining and cholesterol esterification analysis. Each of the six CT60 neo$^R$ HAT$^S$-ELN clones containing the mouse NP-C interval demonstrated correction of the NP-C phenotype as indicated by filipin staining.

Correction of the NP-C phenotype was not observed in any of the six CT60 neo$^R$ HAT$^S$-ELC fusion clones by filipin staining.

Cholesterol esterification analyses were performed on parental cell lines and fusion clones as a secondary method of screening for correction of the NP-C phenotype. Following overnight uptake of LDL by normal cells (ELN), cholesterol ester synthesis was markedly increased. In contrast, stimulation of cholesterol ester synthesis was much less in CT60 neo$^R$ HAT$^S$ and in the NP-C cells (ELC). In the CT60 neo$^R$ HAT$^S$-ELN fusion clones, cholesterol ester synthesis was significantly increased compared to CT60 neo$^R$ HAT$^S$-ELC fusion clones (p~$10^{-7}$), demonstrating complementation of the CT60 NP-C defect by the normal, but not the NP-C genome.

c. Transfer of VACs from the NP-C Interval to CT60 Cells by Yeast Spheroplast Fusion The human gene responsible for NP-C has been localized to a genomic region on chromosome 18, flanked by the genetic markers D18S44 centromerically and NPC-B42 telomerically; the physical map assembled across this interval includes three overlapping YACs, 877F12, 844E3 and 911D5, which span the interval completely (data not shown). These three YACs were modified with a neomycin resistance gene by homologous recombination and then introduced into the NP-C CHO cell line, CT60, by spheroplast fusion. Similarly, another YAC which contains the cystic fibrosis transmembrane conductance regulator gene (CFTR) from chromosome 7, modified with a neomycin resistance gene (yCFTR325-Neo), was used for fusion as an unlinked YAC control.

Spheroplast fusion resulted in neo resistant clones from each of the YACs 877F12, 844E3, and 911D5 (22, 29, and 37 clones, respectively). Neo resistant clones were also obtained from fusions with the control YAC, yCFTR325-Neo. Clonal cell lines were expanded and initially characterized by STS content mapping using STS primers from the NP-C locus. The expected STS contents were found in 8, 10 and 34 clones derived from 877F12, 844E3, and 911D5, respectively. The detailed analyses described below were carried out in 2 clones from 877F12, 2 clones from 844E3 and 5 clones from 911D5.

d. Complementation of the NP-C Phenotype in CT60 Cells by a Single Human YAC from the NP-C Interval Complementation in the YAC fusion clones was analyzed cytologically and biochemically. Filipin staining indicated that all clones evaluated from 911D5 fusions no longer accumulated perinuclear lysosomal cholesterol. In contrast, parental CT60 cells as well as clones derived from 844E3, 877F12 and CFTR displayed extensive perinuclear staining. These findings indicated that the NP-C phenotype was corrected specifically only when YAC 911D5 was present in these cells.

In support of the cytological data, when cellular cholesterol ester synthesis was analyzed, LDL-stimulated esterification was significantly increased compared to CT60 in all clones derived from 911D5, but not in either clone derived from 844E3 or clone A5 derived from 877F12. Clone 877F12A33 displayed modest stimulation of cholesterol esterification compared to CT60, but remained significantly different from control CHO cells (p<0.05). While this data could be taken to suggest partial complementation by 877F12, the filipin staining result clearly demonstrated that 877F12 did not complement the NP-C associated lysosomal accumulation of cholesterol. Together, the phenotypic analyses suggested that 911D5 harbors a human gene capable of correcting the NP-C phenotype, and that the critical interval for identification of the gene responsible for NP-C has been narrowed from the 1 cM interval defined by markers D18S44 and NPC-B42 to the region contained within YAC 911D5, specifically the 300400 kilobases (kb) proximal to NPC-B42.

3. Isolation of Human NP-C cDNA,hNPC1 a. Cloning and Sequencing of hNPC1 cDNA

Following the reduction of the NP-C interval to the 300–400 Kb defined by markers D18S1382 and D18S1388, Bacterial Artificial Chromosomes (BACs) assembled across the interval were sub-cloned into the exon-trapping vectors pSPL3 and pTAG4 according to Krizman et al (1997). Among the trapped exons that mapped to YAC 911D5 and its associated BACs (see FIG. 1), the 3' exon C59 showed identity to an expressed sequence tag (EST) H11600 (GenBank) and the corresponding cluster of 14 ESTs (WI-14881) identified by UNIGENE (Schuler et al, 1996). Northern blot analysis of a multi-tissue RNA panel (Clontech) using EST clone H11600 as probe identified a transcript of approximately 4.9 kb. To extend this clone 5', antisense primers were designed from clone H11600 and used to amplify from adapter-ligated cDNA libraries by long-range PCR (the libraries used were the human fetal brain, ovary and fibroblast Marathon-Ready cDNA libraries (Clontech)). Through successive extensions, the sequence of the entire open reading frame (ORF) was identified. From this, primers were designed to the 5' most sequences and 3' most sequence and used to amplify a single 4673 bp clone, 704-1 containing the entire ORF. Clone 704-1 is hereafter referred to as hNPC1. The authenticity of this clone was provided by 3 additional trapped internal exons that mapped to the NPC1 ORF (FIG. 1).

The hNPC1 cDNA sequence (GenBank accession # AF002020), presented in Seq. I.D. No. 1 predicts a protein of 1278 amino acids with an estimated molecular weight of 142 KDa (Seq. I.D. No.2). The amino terminus contains a 24-amino acid sequence including a central core of 13 hydrophobic amino acids typical of signal peptides that target proteins to the endoplasmic reticulum. Analysis of regions of hydrophobicity and structural motif comparisons predict an integral membrane protein with as many as 16 possible transmembrane (TM) regions. The di-leucine motif (LLNF) found at the C-terminal of hNPC1 has been shown to be a lysosomal targeting sequence for the multitransmembrane lysosomal resident protein Limp II (Orgata et al., 1994); it also mediates endocytosis (Hunziker et al., 1992). Database sequence comparisons revealed extensive identity/similarity to uncharacterized NP-C orthologs in mouse (85%/93%), in yeast (34%/57%) and in C. elegans (30%/55%). A region between residues 55–164, which is free of TM regions, is strongly conserved phylogenetically in these species suggesting functional importance. Within this sequence lies a leucine heptad motif or leucine zipper (residues 73–94) which may mediate polypeptide multimerization as it does for certain transcription factors (Landschultz et al., 1988). A tyrosine phosphorylation site is suggested at residue 506 (Cooper et al., 1984).

b. Verification of Sequence Identity by Complementation in Transient Expression Assays To verify the identity of the hNPC1 cDNA, it was transiently expressed in NPC1-genotyped human fibroblasts and the cells were assayed for filipin staining. The method used, which may also be used for assaying the effects of NPC1 sequence variants, was as follows. DNA vectors 5-4 (704F/G60), 8-1 (87F/G60) 1-1 (704F/G60) and antisense 7-5 (704F/G60) were extraced/purified by alkaline lysis and CsCl gradient centrifugation. On day 0, NPC1 fibroblasts (GM-3123) were plated at 70,000 cells per well in Lab-Tek Chamber Slides (Nunc). On day 1, lipofectamine transfection was performed according to the manufacturer's recommendation (Gibco BRL). On day 2, cells were rinsed once with PBS and then EMEM medium with 10% lipoprotein-deficient serum (LPDS) was then added to the cells for 36 hrs and then replaced with LPDS medium +/−LDL (50 ug/ml) for 24 hrs. The NPC1 genotyped cells were fixed, stained with filipin and cytochemically viewed as described by Blanchette-Mackie et al., (1988). For evaluation, 8–1 fields consisting of approximately 200 cells were randomly selected and viewed with a 25×objective on a microscope slides. Mutant cells with intense filipin fluorescence in perinuclear vacuoles were judged to represent the typical lysosomal cholesterol lipidosis characteristic of NP-C cells. Individual cells discernibly free of the intense perinuclear vacuole fluorescence of neighboring cells were considered to be "corrected". Frequently these "corrected' cells appeared in patches of 2 or more cells and their lysosomes were often seen scattered throughout the cytoplasm.

The results of these assays were as follows. Control cultures representing untransfected (1.9%), mock-transfected (0.4%) and transfection with antisense NPC1 constructs (2.4%) contained the indicated percentage of mutant NP-C1 cells that showed no notable filipin staining of perinuclear vesicles. In contrast, experimental test cultures treated with the cDNA vectors 5-4 (23%), 8-1 (22%), and 1-1 (19%) increased the level of corrected cells to the indicated levels.

Thus, the introduction of NPC1 expression vectors into cultured NPC1-genotyped human fibroblasts by transient transfection restored a normal phenotype by significantly increasing the population of cells which did not accumulate LDL-derived cholesterol in lysosomes. In summary, NP-C cultures that were not treated with the cDNA contained only 1.6+/−1−1.0% cells that were seen to be free of lysosomal cholesterol storage. In contrast, transfection with three independent NPC1 constructs increased (to 21+/−2%) the population of mutant cells that contained no cholesterol accumulation indicating significant (p=0.002) recovery of the normal phenotype.

C. Detection of Mutations in hNPC1 in NP-C Patients

Single-strand conformational polymorphism (SSCP) analysis was used to detect the presence of mutations in the hNPC1 gene in NP-C patients. SSCP analysis was carried out on both cDNA and genomic DNA samples. cDNA was generated from cultured fibroblast RNA using the Super-script System (LTI). For genomic DNA, intron/exon boundaries were identified for 19 exons of NPC1 (constituting 72% of the ORF) thus permitting PCR-based SSCP analysis from genomic DNA using primers designed from intron sequences. DNA was isolated from blood with the Puregene kit (GentraSystem). All PCR were performed in 10 ml reactions using Taq (Perkin Elmer) containing 50 ng of DNA containing a dNTP (0.25 mM each of dA, dG, dT and $^{32}$P-dCTP). Samples were run on 0.6×TBE-buffered MDE (FMC) SSCP gels at 4 W for 14 h. SSCP confomers were excised from the gel and reamplified using the original primer set. Re-amplification products were sequenced (ABI) and compared to normal controls.

8 separate mutations in 9 unrelated NP-C families were identified using this approach; these are summarized in Table 1, below. Among the distinct mutations, a 4-bp insertion results in a frameshift at codon 1205 leading to a premature termination. Of the two multiple nucleotide deletions, a 75-bp deletion (nt 1875–1947) virtually eliminates one predicted domain, TM4, and most of the intervening spacer leading to TM5. To date, 5 missense mutations have been identified; in two instances identical mutations, T1036M (C>T transition) or N1156S (A>G transition), were present in separate families presumed unrelated. Missense mutations at codons 1156 and 1186 result in changes of amino acids that are invariant in phylogenetic orthologs. None of the reported mutations were observed in control DNA samples from 68 unaffected and unrelated individuals.

Positional cloning, mutation detection and cDNA-based expression/correction therefore establish hNPC1 as the gene locus for the major form of NP-C disease.

TABLE 1

Mutations of NPC1 gene in Niemann-Pick C families

| Patient | mRNA sequence change | Predicted protein alteration | Transmembrane region affected | Genotype status |
|---|---|---|---|---|
| ENZ 145 | nt597/Del/6bp (AGGCAC) | Del aa201–202(Gin, Ala) | — | Cmpd Htz |
| 93.47 | nt1775/Del/75bp | Del aa605–629(25aa) | 4 | Cmpd Htz |
| 92.31 | nt2783(A>C) | aa 928/Gin>Pro | — | Cmpd Htz |
| 87.15 | nt3107(C>T) | aa 1036/Thr>Met | 10 | Homozygous |
| 94.17 | nt3107(C>T) | aa 1036/Thr>Met | 10 | Cmpd Htz |
| 94.41 | nt3467(A>G) | aa 1156/Asn*>Ser | 14 | Cmpd Htz |
|  | nt3557(A>G) | aa 1186/Arg*>His | — | — |
| ENZ146 | nt3467(A>G) | aa 1156/Asn*>Ser | 14 | Cmpd Htz |
| 91.78 | nt3499(T<C) | aa 1116/Phe>Leu | — | Cmpd Htz |
| ENZ144 | nt3613Ins/4bp(ACTT) | Frame shift/aa1205>stop | 15–16 | Cmpd Htz |

*amino acid residue conserved in human, mouse, C. elegans, and S. Cerevisae.

4. Isolation of Murine NP-C cDNA, mNPC1 a. The Murine Models

Insights into the biochemical and histopatholgical defects associated with NP-C have come through the use of two murine models which share many of the clinical abnormalities observed in humans with NP-C: elevated levels of sphingomyelin and unesterified cholesterol in liver and spleen, presence of foamy macrophages, neuronal vacuoles, focal axonal swelling, and decreased Purkinje cell number (Higashi et al., 1991). The two murine NP-C models, C57B1Ks/J spm and BALB/c npc$^{nih}$ arose as spontaneous mutations, were determined allelic by cross breeding and have been independently localized to mouse chromosome 18 in a region syntenic to the human NPC1 locus (Erickson, 1997; Morris et al., 1982; Miyawaki et al., 1982; Sakai et al., 1991; Yamamoto et al, 1994). Confirmation that the two mouse loci belong to the same complementation group as the human NPC1 locus was determined using heterokaryon fusions of human NPC1 fibroblasts to mouse mutant cell lines and by DNA mediated complementation using a YAC from the human NPC1 critical region (Akaboshi et al., 1997 and data presented above). Combined, these studies indicate that the same gene is altered in the two mouse NP-C models (spm and npc$^{nih}$) and that the orthologous gene in the mouse models is defective at the human NPC1 locus.

b. Cloning the mNPC1 cDNA

The candidate gene map from the human NPC1 critical region, addressed above, has been combined with high resolution linkage mapping and candidate gene analysis using the BALB/c npc$^{nih}$ mouse model to identify the molecular defect responsible for the neurovisceral abnormalities in NP-C disease. Genetic linkage analysis with 1552 meioses was used to define a 0.36 cM mouse NPC1 critical region. The murine and human genetic resources were integrated by using mouse linkage markers and mouse orthologs of two human ESTs located within human NPC1 critical region to assemble a mouse BAC contig. Partial cDNA clones for the two orthologous genes in mouse (Genbank # AA002656 and MW83C06), were identified in dbEST by BLAST analysis using sequences from the respective human orthologous genes 190B6 and Npc1.

The expression patterns of the two genes, AA002656 and MW83C06 (now termed mNpc1') was examined by Northern blot analysis of RNA isolated from wild type and mutant tissues. While both genes were expressed in all wild type tissues examined. a vast reduction of Npc1 mRNA was observed in npc$^{nih}$/npc$^{nih}$ liver, brain and spm/spm liver compared to wild type tissues. The mNpc1 cDNA sequences from wild type and affected animals were directly compared to determine if the reduced expression in affected tissues was a primary defect in the mNpc1 gene or a secondary event resulting from the NP-C phenotypes. Since both npc$^{nih}$ and spm are isogenic mutations (arising and maintained on inbred genetic backgrounds) any genetically linked, genomic alterations identified between affected and wild-type control mice is most likely causative of the disorder. Although Northern blot analyses demonstrated reduced levels of mRNA in affected tissues, mNpc1 cDNA could be amplified from affected tissues by RT-PCR. Sequence analysis of the cDNA clones from BALB/c npc$^{nih}$/npc$^{nih}$ mouse liver and brain RNA, identified 44 bps of wild type sequence replaced with 24 bps of previously unidentified sequence which results in a frameshift and early truncation of the putative ORF.

The putative mutation in mNpc1 was subsequently confirmed by isolation of the corresponding genomic region from npc$^{nih}$/npc$^{nih}$ affected and control mice. Sequence comparison of the genomic region identified an 824 bp insertion of retrotransposon-like sequences from the Mammalian Apparent LTR-Retrotransposon (MaLR) family (Smit, 1993; Heilein et al., 1986; Kelly, 1994; Cordonnier, 1995). The inserted sequence does not contain a full length MaLR, however, two distinct regions can be identified; the initial 458 bp shows 81% identity to internal sequences of the human endogenous retroviral-like element, HERV-L (Cordonnier et al., 1995), the terminal 370 bp corresponds to the 3' terminus of a mouse transcript (MT) retrotransposon-like sequence (Heilein et al., 1986). Comparison of wild type and npc$^{nih}$/npc$^{nih}$ mutant mNpc1 intronic sequences identified that in addition to the inserted sequences, 703 bp of wild type sequences were deleted. Consistent with the npc$_{nih}$ mutation, MaLR transposition events are prone to rearrangements at integration sites.

These results demonstrate that the NP-C phenotypes observed in BALB/c npc$^{nih}$/npc$^{nih}$ mice result from a mutation of the Npc1 gene. In addition, since npc$^{nih}$ is in the same complementation group and located in the syntenic portion of the genome as the human NPC1 locus, these results are consistent with the findings that the human NPC1 gene is also responsible for the abnormal cholesterol homeostasis and neurodegeneration observed in humans with NP-C disease.

c. Sequence Analysis

Analysis of the mNpc1 cDNA (depicted in Seq. I.D. No. 3) predicts an ORF of 1278 amino acids (Seq. I.D. No. 4) which encodes an N-terminal putative signal peptide sequence followed by a domain that is unique to the NPC1 orthologs (in mouse, human, C. elegans and S. cerevisiae), and thirteen putative transmembrane domains that include a potential sterol-sensing domain (SSD)(see FIG. 3). The NPC domain consists of 112 amino acids and is marked by eight cysteine residues whose spacing is conserved between all NPC1 orthologs analyzed (FIG. 4). Extensive sequence similarity is observed between the murine NPC1 gene and its human ortholog in both the 3834 bps of putative ORF and in a portion of the 3' UTR. In addition, both murine and human orthologs of AA002656 and Npc1 are transcribed in opposite orientations, overlap for 284 bp of the 3' end and within this region exhibit 163 bps of evolutionary conservation (86% nucleic acid identity). A functional significance for this overlap and evolutionary conservation is not clear, however possibilities include co-regulation of mRNA transcription by sharing an enhancer element, regulation of RNA stability or translation due to direct, interaction between Npc1 mRNA and AA002656 mRNA.

The prediction of a SSD in the NPC1 protein is based upon homology to two other genes that have previously been identified as having SSDs and are also crucial for intracellular cholesterol homeostasis, HMG-CoA reductase and SREB cleavage activating protein (SCAP). The region of HMG-CoA reductase containing the SSD is responsible for its targeted degradation in response to intracellular sterol levels (Skalnik et al., 1988; Gil et al., 1985). HMG-CoA reductase activity is also transcriptionally regulated by cholesterol levels via the membrane bound transcription factors SREBP1 and SREBP2, whose cleavage and release from the membrane is in turn regulated by the sterol responsive gene, SCAP. A D443N mutation in the SSD of SCAP blocks its inhibition of cleavage stimulating activity of the transcription of SREBP factors, and directly alters intracellular cholesterol responsive pathways through transcriptional regulation (Hua et al., 1996). Of interest, this amino acid is also conserved in the putative SSD in NPC1 of mouse, man and worm (FIG. 3). The presence of a putative SSD in NPC1 suggests that its function involves direct interactions with sterol moieties. This is consistent with the abnormalities in cellular cholesterol homeostasis observed in individuals with NP-C disease.

Extensive amino acid homology is also observed between the putative transmembrane and SSD of NPC1 with eleven of the twelve transmembrane domains of the Patched (PTC) protein. The presence of a SSD has not been previously described in PTC, nor has PTC been implicated in cholesterol homeostasis. However recently, several links have been made between PTC signaling, neuronal development and cholesterol homeostasis. The secreted signaling molecule, Sonic Hedgehog (SHH), contains a covalently attached cholesterol moiety and has been shown to biochemically interact with PTC. In addition, mutations in SHH, or mutations that result in endogenous cholesterol deficiency (genetic deficiencies of apolipoprotein B, megalin or 7-dehydrocholesterol-$\Delta^7$-reductase (Smith-Lemli-Opitz syndrome)) result in abnormal central nervous system development and function including holoprosencephaly. Given the structural similarities between NPC1 and PTC, it raises the possibility that NPC1 could also interact with protein-sterol complexes that are required for normal neuronal development and/or function. Alternatively, alterations in cellular cholesterol homeostasis in utero could indirectly reduce the function of proteins, such as SHH, that require a cholesterol adduct for normal neuronal development and/or function. While neuro-developmental anomalies such as holoprosencephaly have not been observed in $npc^{nih}/npc^{nih}$ mice, there is a significant deviation from the expected ratio of $npc^{nih}/npc^{nih}$ mice obtained from intercrosses. Further developmental and histological analyses using the BALB/c $Npc1^{npc-nih}$ mouse model are needed to determine if the neurological defects in NP-C result from defective neural development or arise secondary to the iysosomal cholesterol accumulation. Biochemical and genetic analyses of the NPC1 protein using the mouse, worm and yeast model systems will provide powerful resources for assessment of pharmacological interventions and for understanding the role of NPC1 in intracellular cholesterol homeostasis and in the etiology of neurodegeneration in NP-C disease.

5. Preferred Method for Making NPC1 cDNAs

The foregoing discussion describes the original means by which the human and murine NPC1 cDNAs were obtained and also provides the nucleotide sequence of these cDNAs. With the provision of this sequence information, the polymerase chain reaction (PCR) may now be utilized in a more direct and simple method for producing these cDNAs.

To amplify the human or murine cDNA sequences, total RNA is extracted from human or murine fibroblast cells, respectively, and used as a template for performing the reverse transcription-polymerease chain reaction (RT-PCR) amplification of cDNA. Methods and conditions for RT-PCR are described above and in Kawasaki et al. (1990). The selection of PCR primers will be made according to the portions of the particular cDNA which are to be amplified. Primers may be chosen to amplify small segments of a cDNA or the entire cDNA molecule. Variations in amplification conditions may be required to accommodate primers of differing lengths; such considerations are well known in the art and are discussed in Innis et al. (1990). For example, the open reading frame of the human NPC1 cDNA may be amplified using the following combination of primers:

primer A1 5' ATGACCGCTCGCGGCCTGGCCCTTG 3' (Seq. I.D. No. 10)
primer A2 5' GAAATTTAGAAGCCGTTCGCGCTC 3' (Seq. I.D. No. 11)
and the ORF of the murine NPC1 cDNA may be amplified using the following combination of primers:
primer B1 5' ATGGGTGCGCACCACCCGGCCCTC 3' (Seq. I.D. No. 12)
primer B2 5' AAAATTGAGGAGTCGTTCTCTCTC 3' (Seq. I.D. No. 13)

These primers are illustrative only; it will be appreciated by one skilled in the art that many different primers may be derived from the provided cDNA sequence in order to amplify particular regions of the cDNAs.

Alternatively, the gene sequences corresponding to the cDNA sequences presented herein (i.e. the genomic sequence including introns) or pieces of such gene sequences may be obtained by amplification using primers based on the presented cDNA sequences using human or murine genomic DNA as a template.

6. Isolation of NP-C Genomic Sequences

Having provided herein the cDNA sequence of the human and mouse NPC1 cDNAs, cloning of the corresponding genomic nucleotide sequences is now enabled. These genomic sequence may readily be obtained by standard laboratory methods, such as RACE-PCR amplification using a human genomic DNA library or genomic DNA extracted directly from human cells as a template. As discussed above (and illustrated in FIG. 1), the inventors have determined that the human NPC1 gene is present on YAC 911D5 between the markers D18S1382 and D18S1388 and also on the corresponding BACs 238D17, 98L14 and 108N2. Therefore, the genomic region that includes the human NPC1 gene has been identified and the genomic sequence may be readily obtained using the cDNA sequence information presented herein. The human genomic sequence may thus be determined by probing a cosmid library made from YAC 911D5 or from the corresponding BACs and thereafter sequencing the hybridizing sub-clones. Alternatively the BACs may be sequenced directly.

Having the intron sequence data for the genomic sequence will be valuable for diagnostic applications, e.g., looking for splice-site mutations. The various applications described below (e.g., expression of the NPC1 protein for use in producing antibodies) are described using the NPC1 cDNA sequences, but may also be performed using the corresponding genomic sequences.

7. Production of Nucleotide Sequence Variants of NPC1 cDNAs and Amino Acid Sequence Variants of NPC1 Proteins Seq. I.D. Nos. 1 and 3 show the nucleotide sequences of the human and murine NPC1 cDNAs, respectively, and the amino acid sequence of the human and murine NPC1 proteins encoded by these cDNAs are shown in Seq. I.D. Nos. 2 and 4, respectively. Orthologous sequences from yeast and *C. elegans* are also provided in the sequence listing. The biological activity of the NPC1 protein (whether of human or murine origin) is its ability to prevent abnormal lysosomal cholesterol accumulation when transiently expressed in NP-C cells. In other words, this protein complements the cholesterol accumulation that phenotypically characterizes NP-C cells. This activity of the NPC1 protein may readily be determined using transient expression studies in NP-C fibroblasts in conjunction with filipin staining as described in Section 3(b) above.

Having presented the nucleotide sequence of the human, murine, yeast and *C. elegans* NPC1 cDNAs and the amino acid sequences of the encoded proteins, this invention now also facilitates the creation of DNA molecules, and thereby proteins, which are derived from those disclosed but which vary in their precise nucleotide or amino acid sequence from those disclosed. Such variants may be obtained through a combination of standard molecular biology laboratory techniques and the nucleotide sequence information disclosed by this invention.

Variant DNA molecules include those created by standard DNA mutagenesis techniques, for example, M13 primer mutagenesis. Details of these techniques are provided in Sambrook et al. (1989), Ch. 15. By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the biological activity of the NPC1 protein are comprehended by this invention.

DNA molecules and nucleotide sequences which are derived from the disclosed DNA molecules as described above may also be defined as DNA sequences which hybridize under stringent conditions to the DNA sequences disclosed, or fragments thereof. Hybridization conditions resulting in particular degrees of stringency will vary depending upon the nature of the hybridization method of choice and the composition and length of the hybridizing DNA used. Generally, the temperature of hybridization and the ionic strength (especially the Na$^+$ concentration) of the hybridization buffer will determine the stringency of hybridization. Calculations regarding hybridization conditions required for attaining particular degrees of stringency are discussed by Sambrook et al. (1989), chapters 9 and 11, herein incorporated by reference. By way of illustration only, a hybridization experiment may be performed by hybridization of a DNA molecule (for example, a variant of the hNPC1 cDNA) to a target DNA molecule (for example, the hNPC1 cDNA) which has been electrophoresed in an agarose gel and transferred to a nitrocellulose membrane by Southern blotting (Southern, 1975), a technique well known in the art and described in Sambrook et al. (1989). Hybridization with a target probe labeled, for example, with [$^{32}$P]-dCTP is generally carried out in a solution of high ionic strength such as 6×SSC at a temperature that is 20–25° C. below the melting temperature, T$_m$, described below. For such Southern hybridization experiments where the target DNA molecule on the Southern blot contains 10 ng of DNA or more, hybridization is typically carried out for 6–8 hours using 1–2 ng/ml radiolabeled probe (of specific activity equal to 10$^9$ CPM/µg or greater). Following hybridization, the nitrocellulose filter is washed to remove background hybridization. The washing conditions should be as stringent as possible to remove background hybridization but to retain a specific hybridization signal. The term T$_m$ represents the temperature above which, under the prevailing ionic conditions, the radiolabeled probe molecule will not hybridize to its target DNA molecule. The T$_m$ of such a hybrid molecule may be estimated from the following equation (Bolton and McCarthy, 1962):

$$T_m = 81.5° C. - 16.6(\log_{10}[Na^+]) + 0.41(\%G+C) - 0.63(\% \text{ formamide}) - (600/l)$$

Where l=the length of the hybrid in base pairs.
This equation is valid for concentrations of Na$^+$ in the range of 0.01 M to 0.4 M, and it is less accurate for calculations of T$_m$ in solutions of higher [Na$^+$]. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., 1989).

Thus, by way of example, for a 150 base pair DNA probe with a hypothetical GC content of 45%, a calculation of hybridization conditions required to give particular stringencies may be made as follows:

For this example, it is assumed that the filter will be washed in 0.3×SSC solution following hybridization, thereby

[Na$^+$]=0.045M
%GC=45%
Formamide concentration=0
l=150 base pairs $$T_m = 81.5 - 16(\log_{10}[Na^+]) + (0.41 \times 45) - (600/150)$$

and so T$_m$=74.4° C.

The T$_m$ of double-stranded DNA decreases by 1–1.5° C. with every 1% decrease in homology (Bonner et al., 1973). Therefore, for this given example, washing the filter in 0.3×SSC at 59.4–64.4° C. will produce a stringency of hybridization equivalent to 90%; that is, DNA molecules with more than 10% sequence variation relative to the target cDNA will not hybridize. Alternatively, washing the hybridized filter in 0.3×SSC at a temperature of 65.4–68.4° C. will yield a hybridization stringency of 94%; that is, DNA molecules with more than 6% sequence variation relative to the target cDNA molecule will not hybridize. The above example is given entirely by way of theoretical illustration. One skilled in the art will appreciate that other hybridization techniques may be utilized and that variations in experimental conditions will necessitate alternative calculations for stringency.

For purposes of the present invention, "stringent conditions" encompass conditions under which hybridization will only occur if there is less than 25% mismatch between the hybridization probe and the target sequence. "Stringent conditions" may be broken down into particular levels of stringency for more precise definition. Thus, as used herein, "moderate stringency" conditions are those under which DNA molecules with more than 25% sequence variation (also termed "mismatch") will not hybridize; conditions of "medium stringency" are those under which DNA molecules with more than 15% mismatch will not hybridize, and conditions of "high stringency" are those under which DNA sequences with more than 10% mismatch will not hybridize. Conditions of "very high stringency" are those under which DNA sequences with more than 6% mismatch will not hybridize.

The degeneracy of the genetic code further widens the scope of the present invention as it enables major variations in the nucleotide sequence of a DNA molecule while maintaining the amino acid sequence of the encoded protein. For example, the third amino acid residue of the mNPC1 protein is alanine. This is encoded in the mNPC1 cDNA by the nucleotide codon triplet GCG. Because of the degeneracy of the genetic code, three other nucleotide codon triplets—GCT, GCC and GCA—also code for alanine. Thus, the nucleotide sequence of the MNPC1 cDNA could be changed at this position to any of these three codons without affecting the amino acid composition of the encoded protein or the characteristics of the protein. The genetic code and variations in nucleotide codons for particular amino acids are presented in Tables 2 and 3. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein also comprehended by this invention.

TABLE 2

The Genetic Code

| First Position (5' end) | Second Position | | | | Third Position (3' end) |
|---|---|---|---|---|---|
| | T | C | A | G | |
| T | Phe | Ser | Tyr | Cys | T |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |

TABLE 2-continued

The Genetic Code

| First Position (5' end) | Second Position | | | | Third Position (3' end) |
| --- | --- | --- | --- | --- | --- |
| | T | C | A | G | |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

"Stop (och)" stands for the ocre termination triplet, and "Stop(amb)" for the amber.
ATG is the most common initiator codon;
GTG usually codes for valine, but it can also code for methionine to initiate an mRNA chain.

TABLE 3

The Degeneracy of the Genetic Code

| Number of Synonymous Codons | Amino Acid | Total Number of Codons |
| --- | --- | --- |
| 6 | Leu, Ser, Arg | 18 |
| 4 | Gly, Pro, Ala, Val, Thr | 20 |
| 3 | Ile | 3 |
| 2 | Phe, Tyr, Cys, His, Gln, Glu, Asn, Asp, Lys | 18 |
| 1 | Met, Trp | 2 |

Total number of codons for amino acids 61
Number of codons for termination 3
Total number of codons in genetic code 64

One skilled in the art will recognize that the DNA mutagenesis techniques described above may be used not only to produce variant DNA molecules, but will also facilitate the production of proteins which differ in certain structural aspects from the NPC1 protein, yet which proteins are clearly derivative of this protein and which maintain the essential functional characteristic of the NPC1 protein as defined above. Newly derived proteins may also be selected in order to obtain variations on the characteristic of the NPC1 protein, as will be more fully described below. Such derivatives include those with variations in amino acid sequence including minor deletions, additions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for optimal activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure.

Substitutional variants are those in which at least one residue in the amino acid sequence has been removed and a different residue inserted in its place. Such substitutions generally are made in accordance with the following Table 4 when it is desired to finely modulate the characteristics of the protein. Table 4 shows amino acids which may be substituted for an original amino acid in a protein and which are regarded as conservative substitutions.

TABLE 4

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 4, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the NPC1 protein by transient expression of the protein in question in NP-C cells in conjunction with filipin staining as described above.

The murine and human NPC1 genes, NPC1 cDNAs, DNA molecules derived therefrom and the protein encoded by these cDNAs and derivative DNA-molecules may be utilized in aspects of both the study of NP-C and for diagnostic and therapeutic applications related to NP-C. Utilities of the present invention include, but are not limited to, those utilities described herein. Those skilled in the art will recognize that the utilities herein described are not limited to the specific experimental modes and materials presented and will appreciate the wider potential utility of this invention.

8. Expression of NP-C Proteins

With the provision of the human and murine NPC1 cDNAs, the expression and purification of the corresponding NPC1 protein by standard laboratory techniques is now enabled. The purified protein may be used for functional analyses, antibody production and patient therapy. Furthermore, the DNA sequence of the NPC1 cDNA and the mutant NPC1 cDNAs isolated from NP-C patients as disclosed above can be manipulated in studies to understand the expression of the gene and the function of its product. In this way, the underlying biochemical defect which results in the symptoms of NP-C can be established. The mutant versions of the NPC1 cDNA isolated to date and others which may be isolated based upon information contained herein, may be studied in order to detect alteration in expression patterns in terms of relative quantities, tissue specificity and functional properties of the encoded mutant NPC1 protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpe gene linked to NPC1 proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (1989) (ch. 17, herein incorporated by reference). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (1989) and are well known in the art. Often, proteins expressed at high levels are found in insoluble inclusion bodies. Methods for extracting proteins from these aggregates are described by Sambrook et al. (1989) (ch. 17). Vector systems suitable for the expression of lacZ fusion genes include the pUR series of vectors (Ruther and Muller-Hill, 1983), pEX1-3 (Stanley and Luzio, 1984) and pMR100 (Gray et al., 1982). Vectors suitable for the production of intact native proteins include pKC30 (Shimatake and Rosenberg, 1981), pKK177-3 (Amann and Brosius, 1985) and pET-3 (Studiar and Moffatt, 1986). NPC1 fusion proteins may be isolated from protein gels, lyophilized, ground into a powder and used as an antigen. The DNA sequence can also be transferred to other cloning vehicles, such as other plasmids, bacteriophages, cosmids, animal viruses and yeast artificial chromosomes (YACs) (Burke et al., 1987). These vectors may then be introduced into a variety of hosts including somatic cells, and simple or complex organisms, such as bacteria, fungi (Timberlake and Marshall, 1989), invertebrates, plants (Gasser and Fraley, 1989), and mammals (Pursel et al., 1989), which cell or organisms are rendered transgenic by the introduction of the heterologous NPC1 cDNA.

For expression in mammalian cells, the cDNA sequence may be ligated to heterologous promoters, such as the simian virus (SV)40, promoter in the pSV2 vector (Mulligan and Berg, 1981), and introduced into cells, such as monkey COS-1 cells (Gluzman, 1981), to achieve transient or long-term expression. The stable integration of the chimeric gene construct may be maintained in mammalian cells by biochemical selection, such as neomycin (Southern and Berg, 1982) and mycophoenolic acid (Mulligan and Berg, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., 1981; Gorman et al., 1982). The level of expression of the cDNA can be manipulated with this type of vector, either by using promoters that have different activities (for example, the baculovirus pAC373 can express cDNAs at high levels in *S. frugiperda* cells (Summers and Smith, 1985) or by using vectors that contain promoters amenable to modulation, for example, the glucocorticoid-responsive promoter from the mouse mammary tumor virus (Lee et al., 1982). The expression of the cDNA can be monitored in the recipient cells 24 to 72 hours after introduction (transient expression).

In addition, some vectors contain selectable markers such as the gpt (Mulligan and Berg, 1981) or neo (Southern and Berg, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., 1981) or Epstein-Barr (Sugden et al., 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973) or strontium phosphate (Brash et al., 1987), electroporation (Neumann et al., 1982), lipofection (Felgner et al., 1987), DEAE dextran (McCuthan et al., 1968), microinjection (Mueller et al., 1978), protoplast fusion (Schafner, 1980), or pellet guns (Klein et al., 1987). Alternatively, the cDNA can be introduced by infection with virus vectors. Systems are developed that use, for example, retroviruses (Bernstein et al., 1985), adenoviruses (Ahmad et al., 1986), or Herpes virus (Spaete et al., 1982).

These eukaryotic expression systems can be used for studies of the NPC1 gene and mutant forms of this gene, the NPC1 protein and mutant forms of this protein. Such uses include, for example, the identification of regulatory elements located in the 5' region of the NPC1 gene on genomic clones that can be isolated from human genomic DNA libraries using the information contained in the present invention. The eukaryotic expression systems may also be used to study the function of the normal complete protein, specific portions of the protein, or of naturally occurring or artificially produced mutant proteins. Naturally occurring mutant proteins exist in patients with NP-C, while artificially produced mutant proteins can be designed by site directed mutagenesis as described above. These latter studies may probe the function of any desired amino acid residue in the protein by mutating the nucleotide coding for that amino acid.

Using the above techniques, the expression vectors containing the NPC1 gene or cDNA sequence or fragments or variants or mutants thereof can be introduced into human cells, mammalian cells from other species or non-mammalian cells as desired. The choice of cell is determined by the purpose of the treatment. For example, monkey COS cells (Gluzman, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Expression of the NPC1 protein in eukaryotic cells may be used as a source of proteins to raise antibodies. The NPC1 protein may be extracted following release of the protein into the supernatant as described above, or, the cDNA sequence may be incorporated into a eukaryotic expression vector and expressed as a chimeric protein with, for example, α-globin. Antibody to α-globin is thereafter used to purify the chimeric protein. Corresponding protease cleavage sites engineered between the α-globin gene and the cDNA are then used to separate the two polypeptide fragments from one another after translation. One useful expression vector for generating β-globin chimeric proteins is pSG5 (Stratagene). This vector encodes rabbit β-globin.

The recombinant cloning vector, according to this invention, then comprises the selected DNA of the DNA sequences of this invention for expression in a suitable host. The DNA is operatively linked in the vector to an expression control sequence in the recombinant DNA molecule so that the NPC1 polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this invention, may be selected from the group consisting of bacteria; yeast; fungi; plant; insect; mouse or other animal; or human tissue cells.

It is appreciated that for mutant or variant DNA sequences, similar systems are employed to express and produce the mutant or variant product.

9. Production of Anti-NPC1 Protein Antibodies a. Production of an Antibody to NPC1 Protein Monoclonal or polyclonal antibodies may be produced to either the normal NPC1 protein or mutant forms of this protein. Optimally, antibodies raised against the NPC1 protein will specifically detect the NPC1 protein. That is, antibodies raised against the hNPC1 protein would recognize and bind the hNPC1 protein and would not substantially recognize or bind to other proteins found in human cells. The determination that an antibody specifically detects an NPC1 protein is made by any one of a number of standard immunoassay methods; for instance, the Western blotting technique (Sambrook et al., 1989). To determine that a given antibody preparation (such as one produced in a mouse against the hNPC1 protein) specifically detects the hNPC1 protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the hNPC1 protein will, by this technique, be shown to bind to the hNPC1 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-hNPC1 protein binding.

Antibodies that specifically bind to an NPC1 protein belong to a class of molecules that are referred to herein as "specific binding agents." Specific binding agents that are capable of specifically binding to an NPC1 protein may include polyclonal antibodies, monoclonal antibodies (including humanized monoclonal antibodies) and fragments of monoclonal antibodies such as Fab, F(ab')2 and Fv fragments, as well as any other agent capable of specifically binding to an NPC1 protein.

Substantially pure NPC1 protein suitable for use as an immunogen is isolated from the transfected or transformed cells as described above. Concentration of protein in the final preparation is adjusted, for example, by concentration on an Amicon filter device, to the level of a few micrograms per milliliter. Monoclonal or polyclonal antibody to the protein can then be prepared as follows.

b. Monoclonal Antibody Production by Hybridoma Fusion

Monoclonal antibody to epitopes of the NPC1 protein identified and isolated as described can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980), and derivative methods thereof. Selected positive clones can be expanded and their monoclonal antibody product harvested for use. Detailed procedures for monoclonal antibody production are described in Harlow and Lane (1988). In addition, protocols for producing humanized forms of monoclonal antibodies (for therapeutic applications) and fragments of monoclonal antibodies are known in the art.

c. Polyclonal Antibody Production by Immunization

Polyclonal antiserum containing antibodies to heterogenous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher (1980).

d. Antibodies Raised against Synthetic Peptides

A third approach to raising antibodies against the NPC1 protein is to use synthetic peptides synthesized on a commercially available peptide synthesizer based upon the predicted amino acid sequence of the NPC1 protein.

c. Antibodies Raised by Injection of NPC1 cDNA

Antibodies may be raised against the NPC1 protein by subcutaneous injection of a DNA vector which expresses the NPC1 protein into laboratory animals, such as mice. Delivery of the recombinant vector into the animals may be achieved using a hand-held form of the Biolistic system (Sanford et al., 1987) as described by Tang et al. (1992). Expression vectors suitable for this purpose may include those which express the NPC1 cDNA under the transcriptional control of either the human $\beta$-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

10. Use of NPC1 Nucleotide Sequences for Diagnosis of NP-C Carriers and Sufferers One major application of the hNPC1 cDNA sequence information presented herein is in the area of genetic testing, carrier detection and prenatal diagnosis for NP-C. Individuals carrying mutations in the hNPC1 gene (disease carrier or patients) may be detected at the DNA level with the use of a variety of techniques. For such a diagnostic procedure, a biological sample of the subject, containing either DNA or RNA derived from the subject, is assayed for the presence of a mutant hNPC1 gene. Suitable biological samples include samples containing genomic DNA or RNA obtained from body cells, such as those present in peripheral blood, urine, saliva, tissue biopsy, surgical specimen, amniocentesis samples and autopsy material. The detection of mutations in the hNPC1 gene may be detected using the SSCP analysis as described in Section 3(c). The detection in the biological sample of either a mutant hNPC1 gene or a mutant hNPC1 RNA may also be performed by a number of other methodologies known in the art, as outlined below.

One suitable detection techniques is the polymerase chain reaction amplification of reverse transcribed RNA (RT-PCR) of RNA isolated from lymphocytes followed by direct DNA sequence determination of the products. The presence of one or more nucleotide difference between the obtained sequence and the hNPC1 cDNA sequence presented herein, and especially, differences in the ORF portion of the nucleotide sequence are taken as indicative of a potential hNPC1 gene mutation. The effect of such nucleotide differences may be determined by engineering the nucleotide differences into the hNPC1 cDNA through standard mutagenesis techniques and then assaying the effect of this mutant cDNA by filipin staining when transiently inroduced into NP-C cells. If the cells show normal filipin staining (i.e., the same staining patterns as observed in non-NPOC cells) then the observed nucleotide differences are regarded as "neutral," and the patient is not classified as an NP-C carrier or sufferer on the basis of this nucleotide difference. On the other hand, if the altered cDNA does not restore normal filipin staining to the NP-C cells, the nucleotide difference is regarded as a mutation rather than a natural difference, the protein is an aberrant (or mutant) NPC1 gene product and the patient is classified as an NP-C sufferer or carrier.

Because of the diploid nature of the human genome, both copies of the hNPC1 gene need to be examined to distinguish between NP-C carriers and NP-C sufferers. If a single copy of the hNPC1 gene is found to be mutated and the other copy is "normal," then tie subject is classified as an NP-C carrier or heterozygote. If both copies of the hNPC1 gene are found to be mutated and do not restore normal filipin staining to NP-C cells when transiently expressed in those cells, then the subject is classified as an NP-C sufferer.

Alternatively, DNA extracted from lymphocytes or other cells may be used directly for amplification. The direct amplification from genomic DNA would be appropriate for analysis of the entire hNPC1 gene including regulatory sequences located upstream and downstream from the open reading frame. Reviews of direct DNA diagnosis have been presented by Caskey (1989) and by Landegren et al. (1989).

Further studies of hNPC1 genes isolated from NP-C patients may reveal particular mutations which occur at a high frequency within this population of individuals. In this case, rather than sequencing the entire hNPC1 gene, it may be possible to design DNA diagnostic methods to specifically detect the most common mutations.

The detection of specific DNA mutations may be achieved by methods such as hybridization using specific oligonucleotides (Wallace et al., 1986), direct DNA sequencing (Church and Gilbert, 1988), the use of restriction enzymes (Flavell et al., 1978; Geever et al., 1981), discrimination on the basis of electrophoretic mobility in gels with denaturing reagent (Myers and Maniatis, 1986), RNase protection (Myers et al., 1985), chemical cleavage (Cotton et al., 1985), and the ligase-mediated detection procedure (Landegren et al., 1988).

By way of example, oligonucleotides specific to normal or mutant sequences may be chemically synthesized using commercially available machines, labelled radioactively with isotopes (such as $^{32}$P) or non-radioactively (with tags such as biotin (Ward and Langer et al., 1981), and hybridized to individual DNA samples immobilized on membranes or other solid supports by dot-blot or transfer from gels after electrophoresis. The presence or absence of these specific sequences may then visualized by methods such as autoradiography or fluorometric (Landegren, et al., 1989) or colorimetric reactions (Gebeyehu et al., 1987).

Sequence differences between normal and mutant forms of that gene may also be revealed by the direct DNA sequencing method of Church and Gilbert (1988). Cloned DNA segments may be used as probes to detect specific DNA segments. The sensitivity of this method is greatly enhanced when combined with PCR (Wrichnik et al., 1987; Wong et al., 1987; Stoflet et al., 1988). In this approach, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent tags.

Sequence alterations may occasionally generate fortuitous restriction enzyme recognition sites or may eliminate existing restriction sites. Changes in restriction sites are revealed by the use of appropriate enzyme digestion followed by conventional gel-blot hybridization (Southern, 1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

Genetic testing based on DNA sequence differences may be achieved by detection of alteration in electrophoretic mobility of DNA fragments in gels with or without denaturing reagent. Small sequence deletions and insertions can be visualized by high-resolution gel electrophoresis. For example, a PCR product with small deletions is clearly distinguishable from a normal sequence on an 8% non-denaturing polyacrylamide gel (Nagamine et al., 1989). DNA fragments of different sequence compositions may be distinguished on denaturing formamide gradient gels in which the mobilities of different DNA fragments are retarded in the gel at different positions according to their specific "partial-melting" temperatures (Myers et al., 1985). Alternatively, a method of detecting a mutation comprising a single base substitution or other small change could be based on differential primer length in a PCR. For example, an invariant primer could be used in addition to a primer specific for a mutation. The PCR products of the normal and mutant genes can then be differentially detected in acrylamide gels.

In addition to conventional gel-electrophoresis and blot-hybridization methods, DNA fragments may also be visualized by methods where the individual DNA samples are not immobilized on membranes. The probe and target sequences may be both in solution, or the probe sequence may be immobilized (Saiki et al., 1989). A variety of detection methods, such as autoradiography involving radioisotopes, direct detection of radioactive decay (in the presence or absence of scintillant), spectrophotometry involving calorigenic reactions and fluorometry involved fluorogenic reactions, may be used to identify specific individual genotypes.

If more than one mutation is frequently encountered in the hNPC1 gene, a system capable of detecting such multiple mutations would be desirable. For example, a PCR with multiple, specific oligonucleotide primers and hybridization probes may be used to identify all possible mutations at the same time (Chamberlain et al., 1988). The procedure may involve immobilized sequence-specific oligonucleotides probes (Saiki et al., 1989).

One method that is expected to be particularly suitable for detecting mutations in the NPC1 gene is the use of high density oligonuceolotide arrays (also known as "DNA chips") as described by Hacia et al. (1996).

11. Quantitation of NPC1 Protein

An alternative method of diagnosing NP-C sufferers or NP-C carrier status may be to quantitate the level of NPC1 protein in the cells of an individual. This diagnostic tool would be useful for detecting reduced levels of the NPC1 protein which result from, for example, mutations in the promoter regions of the NPC1 gene or mutations within the coding region of the gene which produced truncated, non-functional polypeptides. The determination of reduced NPC1 protein levels would be an alternative or supplemental approach to the direct determination of NP-C status by nucleotide sequence determination outlined above. The availability of antibodies specific to the NPC1 protein would allow the quantitation of cellular NPC1 protein by one of a number of immunoassay methods which are well known in the art and are presented in Harlow and Lane (1988). Such assays permit both the detection of NPC1 protein in a biological sample and the quantitation of such protein. Typical methods involve combining the biological sample with an NPC1 specific binding agent, such as an anti-NPC1 protein antibody so that complexes form between the binding agent and the NPC1 protein present in the sample, and then detecting or quantitating such complexes.

In particular forms, these assays may be performed with the NPC1 specific binding agent immobilized on a support surface, such as in the wells of a microtiter plate or on a column. The biological sample is then introduced onto the support surface and allowed to interact with the specific binding agent so as to form complexes. Excess biological sample is then removed by washing, and the complexes are detected with a reagent, such as a second anti-NPC1 protein antibody that is conjugated with a detectable marker.

For the purposes of quantitating the NPC1 protein, a biological sample of the subject, which sample includes cellular proteins, is required. Such a biological sample may be obtained from body cells, such as those present in peripheral blood, urine, saliva, tissue biopsy, amniocentesis samples, surgical specimens and autopsy material. Quantitation of NPC1 protein would be made by immunoassay and compared to levels of the protein found in non-NP-C human cells. A significant (preferably 50% or greater) reduction in the amount of NPC1 protein in the cells of a subject compared to the amount of NPC1 protein found in non-NP-C human cells would be taken as an indication that the subject may be an NP-C sufferer or NP-C carrier.

Having illustrated and described the principles of isolating the human NP-C gene and its murine homolog, the proteins encoded by these genes and modes of use of these biological molecules, it should be apparent to one skilled in the art that the invention can be modified in arrangement and detail without departing from such principles. We claim all modifications coming within the spirit and scope of the claims presented herein.

REFERENCES

Ahmad et al. (1986). *J. Virol.* 57:267.
Alt et al. (1978). *J. Biol. Chem.* 253:1357.

Altschul & Gish. (1996). *Methods Enzymol.*, 266, 460–80.
Altschul et al. (1990). *J. Mol. Biol.,* 215, 403–10
Altschul et al. (1 994). *Nature Genet.,* 6, 119–29.
Amann and Brosius (1985). *Gene* 40:183.
Amsterdam et al. (1992) *J. Steroid Biochem. Mol. Biol.,* 43, 875–884.
Auerbach and Wolman (1978). *Nature* 271:69–70.
Ausubel et al. (1987). In *Current Protocols in Molecular Biology*, Greene Publishing Associates and Wiley-Intersciences.
Beaucage et al. (1981) *Tetrahedron Letts.* 22: 1859–1862.
Bernstein et al. (1985). *Gen. Engr'g* 7:235.
Better & Horowitz (1989). *Methods Enzymol.* 178: 476–496.
Blanchette-Mackie et al. (1988) *Proc. Natl. Acad. Sci U.S.A.* 85: 8022–8026.
Bolton and McCarthy (1962). *Proc. Natl. Acad Sci. USA* 48:1390.
Bonner et al. (1973). *J. Mol. Biol.* 81:123.
Brady et al. (1989) *Neurologic Clinics,* 7: 75–87.
Brash et al. (1987). *Mol. Cell Biol.* 7:2013.
Burke et al. (1987). *Science* 236:806–812.
Cadigan et al. (1990) *J. Cell Biol.,* 110, 295–308.
Carstea et al. (1994) *Am. J. Hum. Genet. Suppl.,* 55, A182.
Carstea et al.(1993) *Proc. Natl. Acad. Sci. USA,* 90, 2002–2004.
Caskey (1989). *Science* 236:1223–1228.
Chamberlain et al. (1988). *Nucl. Acids Res.* 16:1141–1155 (1988).
Church and Gilbert (1988). *Proc. Natl. Acad. Sci. USA* 81:1991–1995.
Colbere-Garapin et al.( 1986) *Gene* 50, 279–288.
Cooper et al. (1984) *J. Biol. Chem.* 259: 7835.
Corpet et al. (1988). *Nucleic Acids Research* 16, 10881–90.
Cotton et al. (1985). *Proc. Natl. Acad. Sci. USA* 85:4397–4401.
Cotton et al. (1985). *Proc. Natl. Acad. Sci. USA* 85:4397–4401.
Davison et al.(976) *Somatic Cell Genet.,* 3, 271–280.
Eisenberg (1984). *Annu. Rev. Biochem.* 53:595–623.
Engvall (1980). *Enzymol.* 70:419.
Felgner et al. (1987). *Proc. Natl. Acad. Sci. USA* 84:7413.
Fink et al. 1989) *Neurology* 39: 1040–1049.
Fisher (1980). *Manual of Clinical Immunology*, ch. 42.
Flavell et al. (1978). *Cell* 15:25.
Gasser and Fraley (1989). *Science* 244:1293.
Gebeyehu et al. (1987). *Nucleic Acids Res.* 15:4513–4534.
Geever et al. (1981). *Proc. Natl. Acad. Sci USA* 78:5081.
Gluzman (1981). *Cell* 23:175–182.
Gorman et al. (1982). *Proc. Natl. Acad. Sci USA* 78:6777–6781.
Graham and vander Eb (1973). *Virology* 52:466.
Gray et al. (1982). *Proc. Natl. Acad. Sci. USA* 79:6598.
Hacia et al. (1996). *Nature Genetics* 14(4): 441–447.
Harlow and Lane (1988). *Antibodies, A Laboratory Manual,* Cold Spring Harbor Laboratory, New York.
Higashi et al. (1991) In *Neuropathology in Brain Research,* ed. Ikuta, F. (Elsevier Science Publishers B. V), pp. 85–102.
Higgins and Sharp (1988). *Gene,* 73: 237–244.
Higgins and Sharp (1989). *CABIOS* 5: 151–153.
Huang, et al. (1992). *Computer Applications in the Biosciences* 8, 155–65.
Hoeijmakers et al. (1987) *Exp. Cell Res.* 169, 111–119.
Hunziker et al. (1994) *Cell* 69: 6622.
Huxley et al. (1991) *Genomics,* 9, 742–750.
Innis et al. (1990). *PCR Protocols, A Guide to Methods and Applications*, Innis et al. (eds.), Academic Press, Inc., San Diego, Calif.
Kawasaki et al. (1990). In *PCR Protocols, A Guide to Methods and Applications,* Innis et al. (eds.), 21–27, Academic Press, Inc., San Diego, Calif.
Klein et al. (1987). *Nature* 327:70.
Kohler and Milstein (1975). *Nature* 256:495.
Krizman et al. (1997) *Methods Mol. Biol.* 68: 167.
Kruth and Vaughan (1980) *J. Lipid Res.* 21, 123–130.
Kurimasa and Oshimura(1993) *Human Genetics*, (Springer-Verlag, Heidelberg, Germany).
Lambert et al. (1991) *Proc. Natl. Acad. Sci. USA,* 88, 5907–5911.
Landegren et al. (1988). *Science* 241:1077.
Landegren et al. (1989). *Science* 242:229–237.
Landschultz et al. (1988) *Science* 243: 1681.
Lee et al. (1982). *Nature* 294:228.
Lohrer et al. (1988) *Mol. Gen. Genet.* 212, 474–480.
Lowry et al.(1951) *J. Biol. Chem.,* 193, 265–275.
Mayne et al.(1988) *Gene* 66, 65–76.
McCuthan et al. (1968). *J. Natl Cancer Inst.* 41:351.
McKusick, V. A.(ed.) (1990) In *Mendelian Inheritance in Man,* 9th edition. (Johns Hopkins University Press, Baltimore), pp. clxvii.
Miyawaki et al.(1982) *J Hered.,* 73, 257–263.
Mogayzel et al.(1997) *Hum. Mol. Genet.,* 6, 59–68.
Morris et al. (1982) *Am. J. Pathol.,* 108, 140–149.
Mueller et al. (1978). *Cell* 15:579.
Mulligan et al. (1981). *Proc. Natl. Acad. Sci. USA* 78:1078–2076.
Mulligan and Berg (1981). *Proc. Natl. Acad. Sci. USA* 78:2072–2076.
Myers et al. (1985). *Science* 230:1242.
Myers and Maniatis (1986). *Cold Spring Harbor Symp. Quant. Biol.* 51:275–284.
Nagamine et al. (1989). *Am. J. Hum. Genet.* 45:337–339.
Needleman and Wunsch (1970). *J. Mol. Biol.* 48: 443.
Neumann et al. (1982). *EMBO J* 1:841.
Ohno et al.(1992) *Cell Structure & Function,* 17, 229–235.
Orgata et al. (1994). *J. Biol. Chem.* 269: 5210.
Ouchterlony et al. (1973). In *Handbook of Experimental Immunology*, Wier, D. (ed.) chapter 19. Blackwell.
Pearson et al. (1994). *Methods in Molecular Biology* 24, 307–31.
Pearson and Lipman (1988). *Proc. Natl. Acad Sci. USA* 85: 2444.
Pentchev et al. (1995) In Scriver C. R. (ed.) *The Metabolic & Molecular Bases of Inherited Disease.* (McGraw-Hill, Inc., New York), pp. 2625–2639.
Pentchev et al. (1985) *Proc. Natl. Acad. Sci. USA,* 82, 8247–8251.
Pentchev et al.(1987) *FASEB J,* 1, 40–45.
Pentchev et al. (1986) *J. Biol. Chem.,* 35, 16775–16780.
Pentchev et al.(1984) *J. Biol. Chem.,* 259, 5784–5791.
Pentchev et al.(1994) *BBA,* 1225, 235–243.
Pereira et al. (1991) *Genomics* 9, 8531–8539.
Perou et al.(1996) *Proc. Natl. Acad. Sci. USA,* 93, 5905–5910.
Pursel et al. (1989). *Science* 244:1281–1288.
Ruther and Muller-Hill (1983). *EMBO J.* 2:1791.
Saiki et al. (1989). *Proc. Nat. Acad. Sci. USA* 86:6230–6234.
Sakai et al.(1991) *Biochemical Genetics,* 29, 103–113.
Sakiyama et al. ( 1982) *J. Inherited Metab. Dis.,* 5, 239–240.
Sambrook et al. (1989). In *Molecular Cloning: A Laboratory Manual*, Cold Spring Harbor, N.Y.
Sanford et al. (1987). *Particulate Sci. Technol.* 5:27–37.
Sanger et al. (1977). *Proc. Natl. Acad. Sci. U.S.A.* 74:5463.
Sarver et al. (1981). *Mol. Cell Biol.* 1:486.
Schafner (1980). *Proc. Natl. Acad. Sci. USA* 77:2163–2167.

Schuler et al. (1996) *Science* 274: 540.
Shimatake and Rosenberg (1981). *Nature* (London) 292:128.
Smith and Waterman (1981). *Adv. Appl. Math.* 2: 482.
Sokol et al. (1988) *J. Biol. Chem.,* 263: 3411–3417.
Southern (1975). *J. Mol. Biol.* 98:503.
Southern and Berg (1982). *J. Mol. Appl. Genet* 1:327–341.
Spaete et al. (1982). *Cell* 30:295.
Srivastava and Schlessinger (1991) *Gene,* 103, 53–59.
Stanley and Luzio (1984). *EMBO J.* 3:1429.
Stoflet et al. (1988). *Science* 239:491–494.
Studiar and Moffatt (1986). *J. Mol. Biol.* 189:113
Sugden et al. (1985). *Mol. Cell Biol.* 5:410.
Summers and Smith (1985). In *Genetically Altered Viruses and the Environment*, Fields et al. (Eds.) 22:319–328, Cold Spring Harbor Laboratory Press, Cold Spring Harbor, N.Y.
Tang et al. (1992). *Nature* (London) 356:152–154.
Tijssen (1993). *Laboratory Techniques in Biochemistry and Molecular Biology— Hybridization with Nucleic Acid Probes* Part I, Chapter 2 "Overview of principles of hybridization and the strategy of nucleic acid probe assays", Elsevier, N.Y.
Timberlake and Marshall (1989). *Science* 244:1313–1317.
Trezise and Buchwald (1991). *Nature* 353:434–437.
Vaitukaitis et al. (1971). *J. Clin. Endocrinol. Metab.* 33:988–991.
Wallace et al. (1986). *Cold Spring Harbor Symp. Quant. Biol.* 51:257–261.
Ward and Langer et al. (1981). *Proc. Natl. Acad. Sci. USA* 78:6633–6657.
Wong et al. (1987). *Nature* 330:384–386.
Wrichnik et al. (1987). *Nucleic Acids Res.* 15:529–542.
Yamamoto et al. (1994) *No-To-Hattatsu,* 26, 318.

What is claimed is:

1. A purified protein comprising an amino acid sequence selected from the group consisting of:
   (a) the amino acid sequence shown in SEQ ID NO: 2;
   (b) the amino acid sequence shown in SEQ ID NO: 4; and
   (c) amino acid sequences having at least 95% sequence identity to the sequences specified in (a) or (b),
   wherein the protein has NPC1 protein biological activity.

2. A nucleic acid molecule encoding a protein according to claim 1.

3. A nucleic acid molecule encoding a protein having an amino acid sequence selected from the group consisting of:
   (a) the amino acid sequence shown in SEQ ID NO: 2; and
   (b) the amino acid sequence shown in SEQ ID NO: 4.

4. A nucleic acid molecule according to claim 3 wherein the nucleic acid molecule comprises a nucleotide sequence selected from the group consisting of:
   (a) the nucleotide sequence shown in SEQ ID NO: 1; and
   (b) the nucleotide sequence shown in SEQ ID NO: 3.

5. An isolated nucleic acid molecule which, when introduced into human NPC-1 fibroblast cells in vitro, reduces the accumulation of lysosomal cholesterol in said cells, wherein the molecule hybridizes under conditions of very high stringency to a nucleic acid molecule having a nucleotide sequence selected from the group consisting of:
   (a) SEQ ID NO: 1; and
   (b) SEQ ID NO: 3.

6. A recombinant vector including a nucleic acid molecule according to claim 5.

7. A purified peptide encoded by a nucleic acid molecule according to claim 5.

8. A purified human or mouse NPC1 protein, which protein comprises a sequence that shares at least 95% sequence identity to the sequence shown in SEQ ID NO. 2 or SEQ ID NO. 4, and has NPC1 protein biological activity.

9. An isolated nucleic acid molecule comprising a nucleotide sequence selected from the group consisting of the sequences shown in:
   (a) SEQ ID NO: 1 or its complementary strand;
   (b) SEQ ID NO: 3 or its complementary strand; and
   (c) sequences which hybridize under conditions of very high stringency to a sequence defined in (a) or (b),
   wherein the nucleic acid molecule encodes a protein that has NPC1 protein biological activity.

10. An isolated nucleic acid molecule that encodes a protein having at least 95% amino acid sequence identity to a sequence selected from the group consisting of:
    (a) SEQ ID NO: 2; and
    (b) SEQ ID NO: 4, and which protein has NPC1 protein biological activity.

11. An isolated oligonucleotide for detecting mutations in the human NPC1 gene wherein the oligonucleotide comprises at least 16 consecutive nucleotides of the sequence shown in residues 1–2275 of SEQ ID NO: 1.

12. An oligonucleotide according to claim 11 wherein the oligonucleotide comprises at least 20 consecutive nucleotides of the sequence shown in SEQ ID NO: 1.

13. A nucleic acid molecule encoding a protein having an amino acid sequence selected from the group consisting of:
    (a) the amino acid sequence shown in SEQ ID NO: 2; and
    (b) the amino acid sequence shown in SEQ ID NO: 4.

* * * * *

UNITED STATES PATENT AND TRADEMARK OFFICE
CERTIFICATE OF CORRECTION

PATENT NO.    : 6,426,198 B1
DATED         : June 30, 2002
INVENTOR(S)   : Carstea et al.

It is certified that error appears in the above-identified patent and that said Letters Patent is hereby corrected as shown below:

Title page,
Item [56], References Cited, OTHER PUBLICATIONS, "Vanier et al.," reference, "Genetic Hererogeneity" should read -- "Genetic Heterogeneity" --.

Column 1,
Line 2, "This application claims benefit of Provisional No. 60/051,682 filed Jul. 3, 1997" should read -- "This is a U.S. National Stage of International Application No. PCT/US98/13862, filed July 2, 1998, which was published in English under PCT Article 21(2), which in turn claims the benefit of U.S. Provisional Application No. 60/051,682, filed July 3, 1997. Both applications are incorporated herein in their entirety --.
Line 44, "iysosomes" should read -- lysosomes --.

Column 3,
Line 20, "subclones" should read -- sub-clones --.
Line 37, "Lpal Ip" should read -- Lpal l p --.

Column 5,
Line 65, "a-target" should read -- a target --.

Column 9,
Line 1, "HNPC1" should read -- h$NPCI$ --.

Column 10,
Line 20, "NRNDS" should read -- NINDS --.
Line 21, "fibrobfasts" should read -- fibroblasts --.
Line 33, "Fiippin" should read -- Filipin --.
Line 39, "Perimmune" should read -- Perlmmune --.

Column 11,
Line 27, "HAT$^5$" should read -- HAT$^S$ --.

Column 12,
Line 7, "fusiori" should read -- fusion --.
Line 56, "clones;" should read -- clones, --.

Column 13,
Line 16, "VACs" should read -- YACs --.

Column 14,
Line 4, "300400" should read -- 300-400 --.
Line 66, "extraced" should read -- extracted --.

UNITED STATES PATENT AND TRADEMARK OFFICE
CERTIFICATE OF CORRECTION

PATENT NO. : 6,426,198 B1
DATED : June 30, 2002
INVENTOR(S) : Carstea et al.

It is certified that error appears in the above-identified patent and that said Letters Patent is hereby corrected as shown below:

Column 15,
Line 9, "8-1" should read -- 8-11 --.
Line 54, "1.6+/-1-1.0%" should read -- 1.6+/-1.0% --.

Column 17,
Line 25, "mNpcl'" should read -- m$Npcl$) --.
Line 28, "examined. a vast" should read -- examined, a vast --.
Line 63, "npc$_{nih}$" should read -- npc$^{nih}$ --.

Column 19,
Line 16, "iysosomal" should read -- lysosomal --.

Column 22,
Line 38, "MNPCI" should read -- m$NPCI$ --.

Column 27,
Line 31, "α-globin. Antibody to α-globin" should read -- ß-globin. Antibody to ß-globin --.
Line 33, "α-globin" should read -- ß-globin --.

Column 30,
Line 37 "tie" should read -- the --.

Column 33,
Line 35, remove "Cotton et al. (1985). *Proc. Natl. Acad. Sci. USA* 85:4397-4401, reference.
Line 37, "(976)" should read -- (1976) --.

Signed and Sealed this

Eighteenth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,426,198 B1
DATED : July 30, 2002
INVENTOR(S) : Carstea et al.

It is certified that error appears in the above-identified patent and that said Letters Patent is hereby corrected as shown below:

<u>Title page,</u>
Item [45], "DATED: June 30, 2002" (both occurrences) should read -- "DATED July 30, 2002" --

Signed and Sealed this

Second Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,426,198 B1
DATED : July 30, 2002
INVENTOR(S) : Carstea et al.

It is certified that error appears in the above-identified patent and that said Letters Patent is hereby corrected as shown below:

Title page,
Item [56], References Cited, OTHER PUBLICATIONS, "Vanier et al.," reference, "Genetic Hererogeneity" should read -- "Genetic Heterogeneity" --.

Column 1,
Line 2, "This application claims benefit of Provisional No. 60/051,682 filed Jul. 3, 1997" should read -- "This is a U.S. National Stage of International Application No. PCT/US98/13862, filed July 2, 1998, which was published in English under PCT Article 21(2), which in turn claims the benefit of U.S. Provisional Application No. 60/051,682, filed July 3, 1997. Both applications are incorporated herein in their entirety --.
Line 44, "iysosomes" should read -- lysosomes --.

Column 3,
Line 20, "subclones" should read -- sub-clones --.
Line 37, "Lpal Ip" should read -- Lpal l p --.

Column 5,
Line 65, "a-target" should read -- a target --.

Column 9,
Line 1, "HNPC1" should read -- h*NPCI* --.

Column 10,
Line 20, "NRNDS" should read -- NINDS --.
Line 21, "fibrobfasts" should read -- fibroblasts --.
Line 33, "Fiippin" should read -- Filipin --.
Line 39, "Perimmune" should read -- Perlmmune --.

Column 11,
Line 27, "$HAT^5$" should read -- $HAT^S$ --.

Column 12,
Line 7, "fusiori" should read -- fusion --.
Line 56, "clones;" should read -- clones, --.

Column 13,
Line 16, "VACs" should read -- YACs --.

Column 14,
Line 4, "300400" should read -- 300-400 --.
Line 66, "extraced" should read -- extracted --.

UNITED STATES PATENT AND TRADEMARK OFFICE
CERTIFICATE OF CORRECTION

PATENT NO. : 6,426,198 B1
DATED : July 30, 2002
INVENTOR(S) : Carstea et al.

It is certified that error appears in the above-identified patent and that said Letters Patent is hereby corrected as shown below:

Column 15,
Line 9, "8-1" should read -- 8-11 --.
Line 54, "1.6+/-1-1.0%" should read -- 1.6+/-1.0%" --.

Column 17,
Line 25, "mNpcl'" should read -- m*Npcl*) --.
Line 28, "examined. a vast" should read -- examined, a vast --.
Line 63, "npc$_{nih}$" should read -- npc$^{nih}$ --.

Column 19,
Line 16, "iysosomal" should read -- lysosomal --.

Column 22,
Line 38, "MNPCI" should read -- m*NPCI* --.

Column 27,
Line 31, "α-globin. Antibody to α-globin" should read -- ß-globin. Antibody to ß-globin --.
Line 33, "α-globin" should read -- ß-globin --.

Column 30,
Line 37 "tie" should read -- the --.

Column 33,
Line 35, remove "Cotton et al. (1985). *Proc. Natl. Acad. Sci. USA* 85:4397-4401, reference.
Line 37, "(976)" should read -- (1976) --.

This certificate supersedes Certificate of Correction issued November 2, 2004.

Signed and Sealed this

Twenty-ninth Day of March, 2005

JON W. DUDAS
*Director of the United States Patent and Trademark Office*

SEQUENCE LISTING

```
<160> NUMBER OF SEQ ID NOS:  13

<210> SEQ ID NO 1
<211> LENGTH: 4550
<212> TYPE: DNA
<213> ORGANISM: Homo sapiens
<220> FEATURE:
<221> NAME/KEY: CDS
<222> LOCATION: (1)..(3837)

<400> SEQUENCE: 1 atg acc gct cgc ggc ctg gcc ctt ggc ctc ctc ctg ctg cta ctg tgt         48
Met Thr Ala Arg Gly Leu Ala Leu Gly Leu Leu Leu Leu Leu Leu Cys
  1               5                  10                  15 cca gcg cag gtg ttt tca cag tcc tgt gtt tgg tat gga gag tgt gga         96
Pro Ala Gln Val Phe Ser Gln Ser Cys Val Trp Tyr Gly Glu Cys Gly
             20                  25                  30 att gca tat ggg gac aag agg tac aat tgc gaa tat tct ggc cca cca        144
Ile Ala Tyr Gly Asp Lys Arg Tyr Asn Cys Glu Tyr Ser Gly Pro Pro
         35                  40                  45 aaa cca ttg cca aag gat gga tat gac tta gtg cag gaa ctc tgt cca        192
Lys Pro Leu Pro Lys Asp Gly Tyr Asp Leu Val Gln Glu Leu Cys Pro
     50                  55                  60 gga ttc ttc ttt ggc aat gtc agt ctc tgt tgt gat gtt cgg cag ctt        240
Gly Phe Phe Phe Gly Asn Val Ser Leu Cys Cys Asp Val Arg Gln Leu
 65                  70                  75                  80 cag aca cta aaa gac aac ctg cag ctg cct cta cag ttt ctg tcc aga        288
Gln Thr Leu Lys Asp Asn Leu Gln Leu Pro Leu Gln Phe Leu Ser Arg
                 85                  90                  95 tgt cca tcc tgt ttt tat aac cta ctg aac ctg ttt tgt gag ctg aca        336
Cys Pro Ser Cys Phe Tyr Asn Leu Leu Asn Leu Phe Cys Glu Leu Thr
            100                 105                 110 tgt agc cct cga cag agt cag ttt ttg aat gtt aca gct act gaa gat        384
Cys Ser Pro Arg Gln Ser Gln Phe Leu Asn Val Thr Ala Thr Glu Asp
        115                 120                 125 tat gtt gat cct gtt aca aac cag acg aaa aca aat gtg aaa gag tta        432
Tyr Val Asp Pro Val Thr Asn Gln Thr Lys Thr Asn Val Lys Glu Leu
    130                 135                 140 caa tac tac gtc gga cag agt ttt gcc aat gca atg tac aat gcc tgc        480
Gln Tyr Tyr Val Gly Gln Ser Phe Ala Asn Ala Met Tyr Asn Ala Cys
145                 150                 155                 160 cgg gat gtg gag gcc ccc tca agt aat gac aag gcc ctg gga ctc ctg        528
Arg Asp Val Glu Ala Pro Ser Ser Asn Asp Lys Ala Leu Gly Leu Leu
```

```
                        165                 170                 175
tgt ggg aag gac gct gac gcc tgt aat gcc acc aac tgg att gaa tac    576
Cys Gly Lys Asp Ala Asp Ala Cys Asn Ala Thr Asn Trp Ile Glu Tyr
            180                 185                 190 atg ttc aat aag gac aat gga cag gca cct ttt acc atc act cct gtg    624
Met Phe Asn Lys Asp Asn Gly Gln Ala Pro Phe Thr Ile Thr Pro Val
            195                 200                 205 ttt tca gat ttt cca gtc cat ggg atg gag ccc atg aac aat gcc acc    672
Phe Ser Asp Phe Pro Val His Gly Met Glu Pro Met Asn Asn Ala Thr
            210                 215                 220 aaa ggc tgt gac gag tct gtg gat gag gtc aca gca cca tgt agc tgc    720
Lys Gly Cys Asp Glu Ser Val Asp Glu Val Thr Ala Pro Cys Ser Cys
225                 230                 235                 240 caa gac tgc tct att gtc tgt ggc ccc aag ccc cag ccc cca cct cct    768
Gln Asp Cys Ser Ile Val Cys Gly Pro Lys Pro Gln Pro Pro Pro Pro
            245                 250                 255 cct gct ccc tgg acg atc ctt ggc ttg gac gcc atg tat gtc atc atg    816
Pro Ala Pro Trp Thr Ile Leu Gly Leu Asp Ala Met Tyr Val Ile Met
            260                 265                 270 tgg atc acc tac atg gcg ttt ttg ctt gtg ttt ttt gga gca ttt ttt    864
Trp Ile Thr Tyr Met Ala Phe Leu Leu Val Phe Phe Gly Ala Phe Phe
            275                 280                 285 gca gtg tgg tgc tac aga aaa cgg tat ttt gtc tcc gag tac act ccc    912
Ala Val Trp Cys Tyr Arg Lys Arg Tyr Phe Val Ser Glu Tyr Thr Pro
290                 295                 300 atc gat agc aat ata gct ttt tct gtt aat gca agt gac aaa gga gag    960
Ile Asp Ser Asn Ile Ala Phe Ser Val Asn Ala Ser Asp Lys Gly Glu
305                 310                 315                 320 gcg tcc tgc tgt gac cct gtc agc gca gca ttt gag ggc tgc ttg agg   1008
Ala Ser Cys Cys Asp Pro Val Ser Ala Ala Phe Glu Gly Cys Leu Arg
            325                 330                 335 cgg ctg ttc aca cgc tgg ggg tct ttc tgc gtc cga aac cct ggc tgt   1056
Arg Leu Phe Thr Arg Trp Gly Ser Phe Cys Val Arg Asn Pro Gly Cys
            340                 345                 350 gtc att ttc ttc tcg ctg gtc ttc att act gcg tgt tcg tca ggc ctg   1104
Val Ile Phe Phe Ser Leu Val Phe Ile Thr Ala Cys Ser Ser Gly Leu
            355                 360                 365 gtg ttt gtc cgg gtc aca acc aat cca gtt gac ctc tgg tca gcc ccc   1152
Val Phe Val Arg Val Thr Thr Asn Pro Val Asp Leu Trp Ser Ala Pro
            370                 375                 380 agc agc cag gct cgc ctg gaa aaa gag tac ttt gac cag cac ttt ggg   1200
Ser Ser Gln Ala Arg Leu Glu Lys Glu Tyr Phe Asp Gln His Phe Gly
385                 390                 395                 400 cct ttc ttc cgg acg gag cag ctc atc atc cgg gcc cct ctc act gac   1248
Pro Phe Phe Arg Thr Glu Gln Leu Ile Ile Arg Ala Pro Leu Thr Asp
            405                 410                 415 aaa cac att tac cag cca tac cct tcg gga gct gat gta ccc ttt gga   1296
Lys His Ile Tyr Gln Pro Tyr Pro Ser Gly Ala Asp Val Pro Phe Gly
            420                 425                 430 cct ccg ctt gac ata cag ata ctg cac cag gtt ctt gac tta caa ata   1344
Pro Pro Leu Asp Ile Gln Ile Leu His Gln Val Leu Asp Leu Gln Ile
            435                 440                 445 gcc atc gaa aac att act gcc tct tat gac aat gag act gtg aca ctt   1392
Ala Ile Glu Asn Ile Thr Ala Ser Tyr Asp Asn Glu Thr Val Thr Leu
            450                 455                 460 caa gac atc tgc ttg gcc cct ctt tca ccg tat aac acg aac tgc acc   1440
Gln Asp Ile Cys Leu Ala Pro Leu Ser Pro Tyr Asn Thr Asn Cys Thr
465                 470                 475                 480 att ttg agt gtg tta aat tac ttc cag aac agc cat tcc gtg ctg gac   1488
```

```
                                                           -continued

Ile Leu Ser Val Leu Asn Tyr Phe Gln Asn Ser His Ser Val Leu Asp
            485                 490                 495 cac aag aaa ggg gac gac ttc ttt gtg tat gcc gat tac cac acg cac     1536
His Lys Lys Gly Asp Asp Phe Phe Val Tyr Ala Asp Tyr His Thr His
        500                 505                 510 ttt ctg tac tgc gta cgg gct cct gcc tct ctg aat gat aca agt ttg     1584
Phe Leu Tyr Cys Val Arg Ala Pro Ala Ser Leu Asn Asp Thr Ser Leu
            515                 520                 525 ctc cat gac cct tgt ctg ggt acg ttt ggt gga cca gtg ttc ccg tgg     1632
Leu His Asp Pro Cys Leu Gly Thr Phe Gly Gly Pro Val Phe Pro Trp
        530                 535                 540 ctt gtg ttg gga ggc tat gat gat caa aac tac aat aac gcc act gcc     1680
Leu Val Leu Gly Gly Tyr Asp Asp Gln Asn Tyr Asn Asn Ala Thr Ala
545                 550                 555                 560 ctt gtg att acc ttc cct gtc aat aat tac tat aat gat aca gag aag     1728
Leu Val Ile Thr Phe Pro Val Asn Asn Tyr Tyr Asn Asp Thr Glu Lys
            565                 570                 575 ctc cag agg gcc cag gcc tgg gaa aaa gag ttt att aat ttt gtg aaa     1776
Leu Gln Arg Ala Gln Ala Trp Glu Lys Glu Phe Ile Asn Phe Val Lys
        580                 585                 590 aac tac aag aat ccc aat ctg acc att tcc ttc act gct gaa cga agt     1824
Asn Tyr Lys Asn Pro Asn Leu Thr Ile Ser Phe Thr Ala Glu Arg Ser
            595                 600                 605 att gaa gat gaa cta aat cgt gaa agt gac agt gat gtc ttc acc gtt     1872
Ile Glu Asp Glu Leu Asn Arg Glu Ser Asp Ser Asp Val Phe Thr Val
        610                 615                 620 gta att agc tat gcc atc atg ttt cta tat att tcc cta gcc ttg ggg     1920
Val Ile Ser Tyr Ala Ile Met Phe Leu Tyr Ile Ser Leu Ala Leu Gly
625                 630                 635                 640 cac atc aaa agc tgt cgc agg ctt ctg gtg gat tcg aag gtc tca cta     1968
His Ile Lys Ser Cys Arg Arg Leu Leu Val Asp Ser Lys Val Ser Leu
            645                 650                 655 ggc atc gcg ggc atc ttg atc gtg ctg agc tcg gtg gct tgc tcc ttg     2016
Gly Ile Ala Gly Ile Leu Ile Val Leu Ser Ser Val Ala Cys Ser Leu
        660                 665                 670 ggt gtc ttc agc tac att ggg ttg ccc ttg acc ctc att gtg att gaa     2064
Gly Val Phe Ser Tyr Ile Gly Leu Pro Leu Thr Leu Ile Val Ile Glu
            675                 680                 685 gtc atc ccg ttc ctg gtg ctg gct gtt gga gtg gac aac atc ttc att     2112
Val Ile Pro Phe Leu Val Leu Ala Val Gly Val Asp Asn Ile Phe Ile
        690                 695                 700 ctg gtg cag gcc tac cag aga gat gaa cgt ctt caa ggg gaa acc ctg     2160
Leu Val Gln Ala Tyr Gln Arg Asp Glu Arg Leu Gln Gly Glu Thr Leu
705                 710                 715                 720 gat cag cag ctg ggc agg gtc cta gga gaa gtg gct ccc agt atg ttc     2208
Asp Gln Gln Leu Gly Arg Val Leu Gly Glu Val Ala Pro Ser Met Phe
            725                 730                 735 ctg tca tcc ttt tct gag act gta gca ttt ttc tta gga gca ttg tcc     2256
Leu Ser Ser Phe Ser Glu Thr Val Ala Phe Phe Leu Gly Ala Leu Ser
        740                 745                 750 gtg atg cca gcc gtg cac acc ttc tct ctc ttt gcg gga ttg gca gtc     2304
Val Met Pro Ala Val His Thr Phe Ser Leu Phe Ala Gly Leu Ala Val
            755                 760                 765 ttc att gac ttt ctt ctg cag att acc tgt ttc gtg agt ctc ttg ggg     2352
Phe Ile Asp Phe Leu Leu Gln Ile Thr Cys Phe Val Ser Leu Leu Gly
        770                 775                 780 tta gac att aaa cgt caa gag aaa aat cgg cta gac atc ttt tgc tgt     2400
Leu Asp Ile Lys Arg Gln Glu Lys Asn Arg Leu Asp Ile Phe Cys Cys
785                 790                 795                 800
```

-continued

| | |
|---|---|
| gtc aga ggt gct gaa gat gga aca agc gtc cag gcc tca gag agc tgt<br>Val Arg Gly Ala Glu Asp Gly Thr Ser Val Gln Ala Ser Glu Ser Cys<br>                805                810                815 | 2448 |
| ttg ttt cgc ttc ttc aaa aac tcc tat tct cca ctt ctg cta aag gac<br>Leu Phe Arg Phe Phe Lys Asn Ser Tyr Ser Pro Leu Leu Leu Lys Asp<br>                820                825                830 | 2496 |
| tgg atg aga cca att gtg ata gca ata ttt gtg ggt gtt ctg tca ttc<br>Trp Met Arg Pro Ile Val Ile Ala Ile Phe Val Gly Val Leu Ser Phe<br>                835                840                845 | 2544 |
| agc atc gca gtc ctg aac aaa gta gat att gga ttg gat cag tct ctt<br>Ser Ile Ala Val Leu Asn Lys Val Asp Ile Gly Leu Asp Gln Ser Leu<br>850                  855                860 | 2592 |
| tcg atg cca gat gac tcc tac atg gtg gat tat ttc aaa tcc atc agt<br>Ser Met Pro Asp Asp Ser Tyr Met Val Asp Tyr Phe Lys Ser Ile Ser<br>865                  870                875                880 | 2640 |
| cag tac ctg cat gcg ggt ccg cct gtg tac ttt gtc ctg gag gaa ggg<br>Gln Tyr Leu His Ala Gly Pro Pro Val Tyr Phe Val Leu Glu Glu Gly<br>                885                890                895 | 2688 |
| cac gac tac act tct tcc aag ggg cag aac atg gtg tgc ggc ggc atg<br>His Asp Tyr Thr Ser Ser Lys Gly Gln Asn Met Val Cys Gly Gly Met<br>            900                905                910 | 2736 |
| ggc tgc aac aat gat tcc ctg gtg cag cag ata ttt aac gcg gcg cag<br>Gly Cys Asn Asn Asp Ser Leu Val Gln Gln Ile Phe Asn Ala Ala Gln<br>                915                920                925 | 2784 |
| ctg gac aac tat acc cga ata ggc ttc gcc ccc tcg tcc tgg atc gac<br>Leu Asp Asn Tyr Thr Arg Ile Gly Phe Ala Pro Ser Ser Trp Ile Asp<br>930                  935                940 | 2832 |
| gat tat ttc gac tgg gtg aag cca cag tcg tct tgc tgt cga gtg gac<br>Asp Tyr Phe Asp Trp Val Lys Pro Gln Ser Ser Cys Cys Arg Val Asp<br>945                  950                955                960 | 2880 |
| aat atc act gac cag ttc tgc aat gct tca gtg gtt gac cct gcc tgc<br>Asn Ile Thr Asp Gln Phe Cys Asn Ala Ser Val Val Asp Pro Ala Cys<br>                965                970                975 | 2928 |
| gtt cgc tgc agg cct ctg act ccg gaa ggc aaa cag agg cct cag ggg<br>Val Arg Cys Arg Pro Leu Thr Pro Glu Gly Lys Gln Arg Pro Gln Gly<br>            980                985                990 | 2976 |
| gga gac ttc atg aga ttc ctg ccc atg ttc ctt tcg gat aac cct aac<br>Gly Asp Phe Met Arg Phe Leu Pro Met Phe Leu Ser Asp Asn Pro Asn<br>                995                1000              1005 | 3024 |
| ccc aag tgt ggc aaa ggg gga cat gct gcc tat agt tct gca gtt aac<br>Pro Lys Cys Gly Lys Gly Gly His Ala Ala Tyr Ser Ser Ala Val Asn<br>    1010                  1015                1020 | 3072 |
| atc ctc ctt ggc cat ggc acc agg gtc gga gcc acg tac ttc atg acc<br>Ile Leu Leu Gly His Gly Thr Arg Val Gly Ala Thr Tyr Phe Met Thr<br>1025                  1030                1035                1040 | 3120 |
| tac cac acc gtg ctg cag acc tct gct gac ttt att gac gct ctg aag<br>Tyr His Thr Val Leu Gln Thr Ser Ala Asp Phe Ile Asp Ala Leu Lys<br>                1045                1050                1055 | 3168 |
| aaa gcc cga ctt ata gcc agt aat gtc acc gaa acc atg ggc att aac<br>Lys Ala Arg Leu Ile Ala Ser Asn Val Thr Glu Thr Met Gly Ile Asn<br>            1060                1065                1070 | 3216 |
| ggc agt gcc tac cga gta ttt cct tac agt gtg ttt tat gtc ttc tac<br>Gly Ser Ala Tyr Arg Val Phe Pro Tyr Ser Val Phe Tyr Val Phe Tyr<br>1075                  1080                1085 | 3264 |
| gaa cag tac ctg acc atc att gac gac act atc ttc aac ctc ggt gtg<br>Glu Gln Tyr Leu Thr Ile Ile Asp Asp Thr Ile Phe Asn Leu Gly Val<br>            1090                1095                1100 | 3312 |
| tcc ctg ggc gcg ata ttt ctg gtg acc atg gtc ctc ctg ggc tgt gag<br>Ser Leu Gly Ala Ile Phe Leu Val Thr Met Val Leu Leu Gly Cys Glu<br>1105                  1110                1115                1120 | 3360 |

-continued

| | |
|---|---|
| ctc tgg tct gca gtc atc atg tgt gcc acc atc gcc atg gtc ttg gtc<br>Leu Trp Ser Ala Val Ile Met Cys Ala Thr Ile Ala Met Val Leu Val<br>                1125                  1130                1135 | 3408 |
| aac atg ttt gga gtt atg tgg ctc tgg ggc atc agt ctg aac gct gta<br>Asn Met Phe Gly Val Met Trp Leu Trp Gly Ile Ser Leu Asn Ala Val<br>      1140                  1145                  1150 | 3456 |
| tcc ttg gtc aac ctg gtg atg agc tgt ggc atc tcc gtg gag ttc tgc<br>Ser Leu Val Asn Leu Val Met Ser Cys Gly Ile Ser Val Glu Phe Cys<br>           1155                  1160                  1165 | 3504 |
| agc cac ata acc aga gcg ttc acg gtg agc atg aaa ggc agc cgc gtg<br>Ser His Ile Thr Arg Ala Phe Thr Val Ser Met Lys Gly Ser Arg Val<br>      1170                  1175                  1180 | 3552 |
| gag cgc gcg gaa gag gca ctt gcc cac atg ggc agc tcc gtg ttc agt<br>Glu Arg Ala Glu Glu Ala Leu Ala His Met Gly Ser Ser Val Phe Ser<br>1185                  1190                  1195                  1200 | 3600 |
| gga atc aca ctt aca aaa ttt gga ggg att gtg gtg ttg gct ttt gcc<br>Gly Ile Thr Leu Thr Lys Phe Gly Gly Ile Val Val Leu Ala Phe Ala<br>           1205                  1210                  1215 | 3648 |
| aaa tct caa att ttc cag ata ttc tac ttc agg atg tat ttg gcc atg<br>Lys Ser Gln Ile Phe Gln Ile Phe Tyr Phe Arg Met Tyr Leu Ala Met<br>      1220                  1225                  1230 | 3696 |
| gtc tta ctg gga gcc act cac gga tta ata ttt ctc cct gtc tta ctc<br>Val Leu Leu Gly Ala Thr His Gly Leu Ile Phe Leu Pro Val Leu Leu<br>           1235                  1240                  1245 | 3744 |
| agt tac ata ggg cca tca gta aat aaa gcc aaa agt tgt gcc act gaa<br>Ser Tyr Ile Gly Pro Ser Val Asn Lys Ala Lys Ser Cys Ala Thr Glu<br>      1250                  1255                  1260 | 3792 |
| gag cga tac aaa gga aca gag cgc gaa cgg ctt cta aat ttc tag<br>Glu Arg Tyr Lys Gly Thr Glu Arg Glu Arg Leu Leu Asn Phe<br>1265                  1270                  1275 | 3837 |
| ccctctcgca gggcatcctg actgaactgt gtctaagggt cggtcggttt accactggac | 3897 |
| gggtgctgca tcggcaaggc caagttgaac accggatggt gccaaccatc ggttgtttgg | 3957 |
| cagcagcttt gaacgtagcg cctgtgaact caggaatgca cagttgactt gggaagcagt | 4017 |
| attactagat ctggaggcaa ccacaggaca ctaaacttct cccagcctct tcaggaaaga | 4077 |
| aacctcattc tttggcaagc aggaggtgac actagatggc tgtgaatgtg atccgctcac | 4137 |
| tgacactctg taaaggccaa tcaatgcact gtctgtcctc tccttttag gagtaagcca | 4197 |
| tcccacaagt tctataccat attttagtg acagttgagg ttgtagatac actttataac | 4257 |
| atttatagt ttaaagagct ttattaatgc aataaattaa ctttgtacac attttatat | 4317 |
| aaaaaaacag caagtgattt cagaatgttg taggcctcat tagagcttgg tctccaaaaa | 4377 |
| tctgtttgaa aaaagcaaca tgttcttcac agtgttcccc tagaaaggaa gagatttaat | 4437 |
| tgccagttag atgtggcatg aaatgaggga caaagaaagc atctcgtagg tgtgtctact | 4497 |
| gggttttaac ttatttttct ttaataaaat acattgtttt cctaaaaaaa aaa | 4550 |

<210> SEQ ID NO 2
<211> LENGTH: 1278
<212> TYPE: PRT
<213> ORGANISM: Homo sapiens

<400> SEQUENCE: 2

Met Thr Ala Arg Gly Leu Ala Leu Gly Leu Leu Leu Leu Leu Leu Cys
1                 5                    10                  15

Pro Ala Gln Val Phe Ser Gln Ser Cys Val Trp Tyr Gly Glu Cys Gly
           20                   25                   30

```
Ile Ala Tyr Gly Asp Lys Arg Tyr Asn Cys Glu Tyr Ser Gly Pro Pro
         35                  40                  45

Lys Pro Leu Pro Lys Asp Gly Tyr Asp Leu Val Gln Glu Leu Cys Pro
     50                  55                  60

Gly Phe Phe Gly Asn Val Ser Leu Cys Cys Asp Val Arg Gln Leu
 65                  70                  75                  80

Gln Thr Leu Lys Asp Asn Leu Gln Leu Pro Leu Gln Phe Leu Ser Arg
                 85                  90                  95

Cys Pro Ser Cys Phe Tyr Asn Leu Leu Asn Leu Phe Cys Glu Leu Thr
             100                 105                 110

Cys Ser Pro Arg Gln Ser Gln Phe Leu Asn Val Thr Ala Thr Glu Asp
         115                 120                 125

Tyr Val Asp Pro Val Thr Asn Gln Thr Lys Thr Asn Val Lys Glu Leu
     130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                 165                 170                 175

Cys Gly Lys Asp Ala Asp Ala Cys Asn Ala Thr Asn Trp Ile Glu Tyr
             180                 185                 190

Met Phe Asn Lys Asp Asn Gly Gln Ala Pro Phe Thr Ile Thr Pro Val
             195                 200                 205

Phe Ser Asp Phe Pro Val His Gly Met Glu Pro Met Asn Asn Ala Thr
     210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                 245                 250                 255

Pro Ala Pro Trp Thr Ile Leu Gly Leu Asp Ala Met Tyr Val Ile Met
             260                 265                 270

Trp Ile Thr Tyr Met Ala Phe Leu Leu Val Phe Phe Gly Ala Phe Phe
         275                 280                 285

Ala Val Trp Cys Tyr Arg Lys Arg Tyr Phe Val Ser Glu Tyr Thr Pro
     290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
             325                 330                 335

Arg Leu Phe Thr Arg Trp Gly Ser Phe Cys Val Arg Asn Pro Gly Cys
         340                 345                 350

Val Ile Phe Phe Ser Leu Val Phe Ile Thr Ala Cys Ser Ser Gly Leu
     355                 360                 365

Val Phe Val Arg Val Thr Thr Asn Pro Val Asp Leu Trp Ser Ala Pro
     370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
             405                 410                 415

Lys His Ile Tyr Gln Pro Tyr Pro Ser Gly Ala Asp Val Pro Phe Gly
             420                 425                 430

Pro Pro Leu Asp Ile Gln Ile Leu His Gln Val Leu Asp Leu Gln Ile
         435                 440                 445

Ala Ile Glu Asn Ile Thr Ala Ser Tyr Asp Asn Glu Thr Val Thr Leu
```

-continued

```
            450                 455                 460
Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
            500                 505                 510

Phe Leu Tyr Cys Val Arg Ala Pro Ala Ser Leu Asn Asp Thr Ser Leu
            515                 520                 525

Leu His Asp Pro Cys Leu Gly Thr Phe Gly Gly Pro Val Phe Pro Trp
530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
                580                 585                 590

Asn Tyr Lys Asn Pro Asn Leu Thr Ile Ser Phe Thr Ala Glu Arg Ser
                595                 600                 605

Ile Glu Asp Glu Leu Asn Arg Glu Ser Asp Ser Asp Val Phe Thr Val
610                 615                 620

Val Ile Ser Tyr Ala Ile Met Phe Leu Tyr Ile Ser Leu Ala Leu Gly
625                 630                 635                 640

His Ile Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
                660                 665                 670

Gly Val Phe Ser Tyr Ile Gly Leu Pro Leu Thr Leu Ile Val Ile Glu
                675                 680                 685

Val Ile Pro Phe Leu Val Leu Ala Val Gly Val Asp Asn Ile Phe Ile
690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
                740                 745                 750

Val Met Pro Ala Val His Thr Phe Ser Leu Phe Ala Gly Leu Ala Val
                755                 760                 765

Phe Ile Asp Phe Leu Leu Gln Ile Thr Cys Phe Val Ser Leu Leu Gly
                770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
                820                 825                 830

Trp Met Arg Pro Ile Val Ile Ala Ile Phe Val Gly Val Leu Ser Phe
                835                 840                 845

Ser Ile Ala Val Leu Asn Lys Val Asp Ile Gly Leu Asp Gln Ser Leu
                850                 855                 860

Ser Met Pro Asp Asp Ser Tyr Met Val Asp Tyr Phe Lys Ser Ile Ser
865                 870                 875                 880
```

```
Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
                900                 905                 910

Gly Cys Asn Asn Asp Ser Leu Val Gln Gln Ile Phe Asn Ala Ala Gln
                915                 920                 925

Leu Asp Asn Tyr Thr Arg Ile Gly Phe Ala Pro Ser Ser Trp Ile Asp
        930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
                980                 985                 990

Gly Asp Phe Met Arg Phe Leu Pro Met Phe Leu Ser Asp Asn Pro Asn
                995                 1000                1005

Pro Lys Cys Gly Lys Gly Gly His Ala Ala Tyr Ser Ser Ala Val Asn
        1010                1015                1020

Ile Leu Leu Gly His Gly Thr Arg Val Gly Ala Thr Tyr Phe Met Thr
1025                1030                1035                1040

Tyr His Thr Val Leu Gln Thr Ser Ala Asp Phe Ile Asp Ala Leu Lys
                1045                1050                1055

Lys Ala Arg Leu Ile Ala Ser Asn Val Thr Glu Thr Met Gly Ile Asn
                1060                1065                1070

Gly Ser Ala Tyr Arg Val Phe Pro Tyr Ser Val Phe Tyr Val Phe Tyr
                1075                1080                1085

Glu Gln Tyr Leu Thr Ile Ile Asp Asp Thr Ile Phe Asn Leu Gly Val
                1090                1095                1100

Ser Leu Gly Ala Ile Phe Leu Val Thr Met Val Leu Gly Cys Glu
1105                1110                1115                1120

Leu Trp Ser Ala Val Ile Met Cys Ala Thr Ile Ala Met Val Leu Val
                1125                1130                1135

Asn Met Phe Gly Val Met Trp Leu Trp Gly Ile Ser Leu Asn Ala Val
                1140                1145                1150

Ser Leu Val Asn Leu Val Met Ser Cys Gly Ile Ser Val Glu Phe Cys
                1155                1160                1165

Ser His Ile Thr Arg Ala Phe Thr Val Ser Met Lys Gly Ser Arg Val
                1170                1175                1180

Glu Arg Ala Glu Glu Ala Leu Ala His Met Gly Ser Ser Val Phe Ser
1185                1190                1195                1200

Gly Ile Thr Leu Thr Lys Phe Gly Gly Ile Val Val Leu Ala Phe Ala
                1205                1210                1215

Lys Ser Gln Ile Phe Gln Ile Phe Tyr Phe Arg Met Tyr Leu Ala Met
                1220                1225                1230

Val Leu Leu Gly Ala Thr His Gly Leu Ile Phe Leu Pro Val Leu Leu
                1235                1240                1245

Ser Tyr Ile Gly Pro Ser Val Asn Lys Ala Lys Ser Cys Ala Thr Glu
                1250                1255                1260

Glu Arg Tyr Lys Gly Thr Glu Arg Glu Arg Leu Leu Asn Phe
1265                1270                1275

<210> SEQ ID NO 3
<211> LENGTH: 5029
```

```
<212> TYPE: DNA
<213> ORGANISM: Mus sp.
<220> FEATURE:
<221> NAME/KEY: CDS
<222> LOCATION: (1)..(3960)

<400> SEQUENCE: 3
```

| | | | | | | | | | | | | | | | | |
|---|---|---|---|---|---|---|---|---|---|---|---|---|---|---|---|---|
| gtc | tgc | tct | tgc | ccc | ctc | ctt | ggt | cag | gcg | ccg | gtt | ccg | aaa | cct | tgc | 48 |
| Val | Cys | Ser | Cys | Pro | Leu | Leu | Gly | Gln | Ala | Pro | Val | Pro | Lys | Pro | Cys | |
| 1 | | | | 5 | | | | | 10 | | | | | 15 | | |
| ccg | cca | gtg | ccg | cga | cgc | tcg | ggt | cgc | ggt | gct | ccg | cga | gcc | gaa | ctg | 96 |
| Pro | Pro | Val | Pro | Arg | Arg | Ser | Gly | Arg | Gly | Ala | Pro | Arg | Ala | Glu | Leu | |
| | | 20 | | | | | 25 | | | | | 30 | | | | |
| aga | gct | gta | gcc | ccg | cgc | ggc | gac | agc | atg | ggt | gcg | cac | cac | ccg | gcc | 144 |
| Arg | Ala | Val | Ala | Pro | Arg | Gly | Asp | Ser | Met | Gly | Ala | His | His | Pro | Ala | |
| | | 35 | | | | | 40 | | | | | 45 | | | | |
| ctc | ggc | ctg | ctg | ctg | ctg | ctg | ctg | tgc | cct | gcg | cag | gtg | ttt | tcg | | 192 |
| Leu | Gly | Leu | Leu | Leu | Leu | Leu | Leu | Cys | Pro | Ala | Gln | Val | Phe | Ser | | |
| | 50 | | | | | 55 | | | | | 60 | | | | | |
| caa | tcc | tgt | gtt | tgg | tat | gga | gag | tgt | gga | att | gcg | act | gga | gat | aag | 240 |
| Gln | Ser | Cys | Val | Trp | Tyr | Gly | Glu | Cys | Gly | Ile | Ala | Thr | Gly | Asp | Lys | |
| 65 | | | | 70 | | | | | 75 | | | | | 80 | | |
| agg | tac | aac | tgt | aaa | tat | tct | ggc | cca | cca | aaa | ccc | ctc | cca | aag | gac | 288 |
| Arg | Tyr | Asn | Cys | Lys | Tyr | Ser | Gly | Pro | Pro | Lys | Pro | Leu | Pro | Lys | Asp | |
| | | | 85 | | | | | 90 | | | | | 95 | | | |
| ggc | tat | gac | tta | gtg | cag | gaa | ctc | tgt | cca | gga | ctc | ttc | ttt | gac | aat | 336 |
| Gly | Tyr | Asp | Leu | Val | Gln | Glu | Leu | Cys | Pro | Gly | Leu | Phe | Phe | Asp | Asn | |
| | | 100 | | | | | 105 | | | | | 110 | | | | |
| gtc | agt | ctc | tgc | tgt | gac | att | caa | cag | ctt | cag | acg | ctg | aag | agt | aac | 384 |
| Val | Ser | Leu | Cys | Cys | Asp | Ile | Gln | Gln | Leu | Gln | Thr | Leu | Lys | Ser | Asn | |
| | | 115 | | | | | 120 | | | | | 125 | | | | |
| ctg | cag | ctg | ccc | ctg | cag | ttc | ctg | tcc | aga | tgt | ccg | tca | tgt | ttt | tat | 432 |
| Leu | Gln | Leu | Pro | Leu | Gln | Phe | Leu | Ser | Arg | Cys | Pro | Ser | Cys | Phe | Tyr | |
| 130 | | | | | 135 | | | | | 140 | | | | | | |
| aac | cta | atg | acc | ctg | ttt | tgt | gag | cta | aca | tgt | agc | cca | cac | cag | agt | 480 |
| Asn | Leu | Met | Thr | Leu | Phe | Cys | Glu | Leu | Thr | Cys | Ser | Pro | His | Gln | Ser | |
| 145 | | | | 150 | | | | | 155 | | | | | 160 | | |
| cag | ttt | ctg | aat | gtg | aca | gca | act | gaa | gat | tat | ttt | gat | cct | aag | aca | 528 |
| Gln | Phe | Leu | Asn | Val | Thr | Ala | Thr | Glu | Asp | Tyr | Phe | Asp | Pro | Lys | Thr | |
| | | | | 165 | | | | | 170 | | | | | 175 | | |
| ccg | gag | aat | aaa | aca | aat | gta | aag | gaa | tta | gag | tac | tat | gtc | gga | cag | 576 |
| Pro | Glu | Asn | Lys | Thr | Asn | Val | Lys | Glu | Leu | Glu | Tyr | Tyr | Val | Gly | Gln | |
| | | | 180 | | | | | 185 | | | | | 190 | | | |
| agc | ttc | gcg | aat | gcg | atg | tac | aat | gcc | tgc | cgt | gat | gtg | gag | gcg | cct | 624 |
| Ser | Phe | Ala | Asn | Ala | Met | Tyr | Asn | Ala | Cys | Arg | Asp | Val | Glu | Ala | Pro | |
| | | 195 | | | | | 200 | | | | | 205 | | | | |
| tcc | agt | aac | gag | aag | gcc | tta | gga | ctc | ttg | tgt | ggg | agg | gat | gcc | cgt | 672 |
| Ser | Ser | Asn | Glu | Lys | Ala | Leu | Gly | Leu | Leu | Cys | Gly | Arg | Asp | Ala | Arg | |
| | 210 | | | | | 215 | | | | | 220 | | | | | |
| gcc | tgc | aat | gcc | acc | aac | tgg | att | gag | tac | atg | ttc | aat | aaa | gac | aac | 720 |
| Ala | Cys | Asn | Ala | Thr | Asn | Trp | Ile | Glu | Tyr | Met | Phe | Asn | Lys | Asp | Asn | |
| 225 | | | | 230 | | | | | 235 | | | | | 240 | | |
| gga | caa | gcg | cca | ttt | acc | atc | att | cct | gtg | ttt | tca | gat | ctt | tca | atc | 768 |
| Gly | Gln | Ala | Pro | Phe | Thr | Ile | Ile | Pro | Val | Phe | Ser | Asp | Leu | Ser | Ile | |
| | | | | 245 | | | | | 250 | | | | | 255 | | |
| ctt | ggg | atg | gag | ccc | atg | aga | aat | gcc | acc | aaa | ggc | tgc | aat | gag | tct | 816 |
| Leu | Gly | Met | Glu | Pro | Met | Arg | Asn | Ala | Thr | Lys | Gly | Cys | Asn | Glu | Ser | |
| | | 260 | | | | | 265 | | | | | 270 | | | | |
| gta | gat | gag | gtc | acg | ggg | cca | tgt | agc | tgc | cag | gac | tgc | tcc | atc | gtc | 864 |
| Val | Asp | Glu | Val | Thr | Gly | Pro | Cys | Ser | Cys | Gln | Asp | Cys | Ser | Ile | Val | |
| | | 275 | | | | | 280 | | | | | 285 | | | | |

```
tgc ggc ccc aag ccc cag atc ctt cag ggc ata gga ggg ggt ggg ggc      912
Cys Gly Pro Lys Pro Gln Ile Leu Gln Gly Ile Gly Gly Gly Gly Gly
    290                 295                 300 tgg ggc ttg gat gcc atg tat gtc atc atg tgg gtc acc tac gtg gca      960
Trp Gly Leu Asp Ala Met Tyr Val Ile Met Trp Val Thr Tyr Val Ala
305                 310                 315                 320 ttt ctg ttt gtg ttt ttt gga gca ctg ttg gca gtg tgg tgc cac aga     1008
Phe Leu Phe Val Phe Phe Gly Ala Leu Leu Ala Val Trp Cys His Arg
                325                 330                 335 agg cgg tac ttt gtg tct gag tac act ccc att gac agt aac atc gcc     1056
Arg Arg Tyr Phe Val Ser Glu Tyr Thr Pro Ile Asp Ser Asn Ile Ala
            340                 345                 350 ttt tct gtg aat agc agt gac aaa ggg gaa gcc tca tgc tgt gac cca     1104
Phe Ser Val Asn Ser Ser Asp Lys Gly Glu Ala Ser Cys Cys Asp Pro
        355                 360                 365 ctt ggt gca gca ttt gat gac tgt ctg agg cgc atg ttc aca aag tgg     1152
Leu Gly Ala Ala Phe Asp Asp Cys Leu Arg Arg Met Phe Thr Lys Trp
    370                 375                 380 ggg gct ttc tgt gtc cga aat ccc acc tgc atc att ttc ttc tca ttg     1200
Gly Ala Phe Cys Val Arg Asn Pro Thr Cys Ile Ile Phe Phe Ser Leu
385                 390                 395                 400 gcc ttc atc act gtg tgc tct tct ggc ctg gta ttt gtc cag gtc acc     1248
Ala Phe Ile Thr Val Cys Ser Ser Gly Leu Val Phe Val Gln Val Thr
                405                 410                 415 acc aat cct gta gag ctc tgg tca gcc cct cac agt cag gcc cgc ttg     1296
Thr Asn Pro Val Glu Leu Trp Ser Ala Pro His Ser Gln Ala Arg Leu
            420                 425                 430 gaa aag gag tac ttt gac aag cac ttt ggg cct ttc ttt cgc acg gag     1344
Glu Lys Glu Tyr Phe Asp Lys His Phe Gly Pro Phe Phe Arg Thr Glu
        435                 440                 445 cag ctt atc atc caa gcc ccc aac acc agt gtt cat atc tac gaa ccg     1392
Gln Leu Ile Ile Gln Ala Pro Asn Thr Ser Val His Ile Tyr Glu Pro
    450                 455                 460 tac ccc gca gga gcc gat gtg ccc ttc ggg cct cca ttg aac aaa gag     1440
Tyr Pro Ala Gly Ala Asp Val Pro Phe Gly Pro Pro Leu Asn Lys Glu
465                 470                 475                 480 att ctg cac cag gtt ctg aac tta cag atc gcc att gaa agc atc acc     1488
Ile Leu His Gln Val Leu Asn Leu Gln Ile Ala Ile Glu Ser Ile Thr
                485                 490                 495 gca tct tac aac aat gaa acc gtg aca ctg cag gac atc tgt gtg gcc     1536
Ala Ser Tyr Asn Asn Glu Thr Val Thr Leu Gln Asp Ile Cys Val Ala
            500                 505                 510 ccc ctc tct ccc tac aac aag aac tgc acc att atg agt gtg tta aat     1584
Pro Leu Ser Pro Tyr Asn Lys Asn Cys Thr Ile Met Ser Val Leu Asn
        515                 520                 525 tac ttc cag aac agc cat gcg gtg ctg gac agc caa gta ggc gac gac     1632
Tyr Phe Gln Asn Ser His Ala Val Leu Asp Ser Gln Val Gly Asp Asp
    530                 535                 540 ttc tat atc tac gct gat tac cac aca cac ttt ctg tac tgt gta cgg     1680
Phe Tyr Ile Tyr Ala Asp Tyr His Thr His Phe Leu Tyr Cys Val Arg
545                 550                 555                 560 gct ccc gcc tcc ttg aat gat acg agt ttg ctc cac ggt cct tgc ctg     1728
Ala Pro Ala Ser Leu Asn Asp Thr Ser Leu Leu His Gly Pro Cys Leu
                565                 570                 575 ggt aca ttt gga gga ccg gtg ttc ccg tgg ctt gtg ttg ggt ggc tat     1776
Gly Thr Phe Gly Gly Pro Val Phe Pro Trp Leu Val Leu Gly Gly Tyr
            580                 585                 590 gat gat cag aac tac aac aat gcc acc gcg ctt gtg atc acc ttc ccc     1824
Asp Asp Gln Asn Tyr Asn Asn Ala Thr Ala Leu Val Ile Thr Phe Pro
```

```
                595                 600                 605
gtg aat aat tac tac aat gac aca gag agg ctc cag agg gcc tgg gcc    1872
Val Asn Asn Tyr Tyr Asn Asp Thr Glu Arg Leu Gln Arg Ala Trp Ala
        610                 615                 620 tgg gag aaa gag ttt att agt ttt gtg aaa aac tac aag aat cca aat    1920
Trp Glu Lys Glu Phe Ile Ser Phe Val Lys Asn Tyr Lys Asn Pro Asn
625                 630                 635                 640 ctg acc att tct ttc act gct gag cga agc atc gaa gat gag ctc aat    1968
Leu Thr Ile Ser Phe Thr Ala Glu Arg Ser Ile Glu Asp Glu Leu Asn
                645                 650                 655 cgg gaa agt aac agt gac gtg ttc acc gtc atc atc agc tac gtc gtg    2016
Arg Glu Ser Asn Ser Asp Val Phe Thr Val Ile Ile Ser Tyr Val Val
            660                 665                 670 atg ttt ctg tac att tcc ctc gcc ctg ggt cac atc cag agc tgc agc    2064
Met Phe Leu Tyr Ile Ser Leu Ala Leu Gly His Ile Gln Ser Cys Ser
        675                 680                 685 agg ctc ctg gtg gat tct aag atc tcg ctg ggc att gcg ggg atc ctg    2112
Arg Leu Leu Val Asp Ser Lys Ile Ser Leu Gly Ile Ala Gly Ile Leu
    690                 695                 700 atc gtg cta agc tcg gtg gcc tgc tct ctg ggc atc ttc agc tac atg    2160
Ile Val Leu Ser Ser Val Ala Cys Ser Leu Gly Ile Phe Ser Tyr Met
705                 710                 715                 720 ggg atg ccg ctg acc ctc atc gtc att gag gtc atc cca ttc ctg gtg    2208
Gly Met Pro Leu Thr Leu Ile Val Ile Glu Val Ile Pro Phe Leu Val
                725                 730                 735 ctg gct gtc ggg gtg gac aac atc ttc att cta gtg cag acc tac cag    2256
Leu Ala Val Gly Val Asp Asn Ile Phe Ile Leu Val Gln Thr Tyr Gln
            740                 745                 750 aga gat gag cgt ctt cag gag gaa acg ctg gat cag cag ctg ggc agg    2304
Arg Asp Glu Arg Leu Gln Glu Glu Thr Leu Asp Gln Gln Leu Gly Arg
        755                 760                 765 atc ctt gga gaa gtg gcc ccg acc atg ttc ctt tca tcc ttt tct gag    2352
Ile Leu Gly Glu Val Ala Pro Thr Met Phe Leu Ser Ser Phe Ser Glu
    770                 775                 780 acc tca gca ttt ttc ttt ggg gcg ctg tcc tcg atg cca gct gtg cac    2400
Thr Ser Ala Phe Phe Phe Gly Ala Leu Ser Ser Met Pro Ala Val His
785                 790                 795                 800 acc ttc tct ctg ttt gcg gga atg gcc gtc ctc att gac ttc ctc ctt    2448
Thr Phe Ser Leu Phe Ala Gly Met Ala Val Leu Ile Asp Phe Leu Leu
                805                 810                 815 cag att acc tgc ttt gtg agc ctg ttg ggg tta gat att aag agg caa    2496
Gln Ile Thr Cys Phe Val Ser Leu Leu Gly Leu Asp Ile Lys Arg Gln
            820                 825                 830 gag aaa aac cat ctg gac atc ctg tgc tgt gtc aga ggc gct gac gac    2544
Glu Lys Asn His Leu Asp Ile Leu Cys Cys Val Arg Gly Ala Asp Asp
        835                 840                 845 gga caa ggt agc cac gcc tcc gaa agc tac ctg ttt cgc ttc ttc aaa    2592
Gly Gln Gly Ser His Ala Ser Glu Ser Tyr Leu Phe Arg Phe Phe Lys
    850                 855                 860 aac tac ttt gcc ccc ctt ctg ctg aag gac tgg ctg agg cca att gtg    2640
Asn Tyr Phe Ala Pro Leu Leu Leu Lys Asp Trp Leu Arg Pro Ile Val
865                 870                 875                 880 gta gcg gtg ttt gtg ggc gtt ctg tca ttc agt gtt gcg gtg gtg aac    2688
Val Ala Val Phe Val Gly Val Leu Ser Phe Ser Val Ala Val Val Asn
                885                 890                 895 aaa gta gac atc ggg ttg gat cag tct ctc tca atg cca aac gat tcg    2736
Lys Val Asp Ile Gly Leu Asp Gln Ser Leu Ser Met Pro Asn Asp Ser
            900                 905                 910 tat gtg att gct aat ttc aaa tca ctc gct cag tac ctg cac tcg ggc    2784
```

```
Tyr Val Ile Ala Asn Phe Lys Ser Leu Ala Gln Tyr Leu His Ser Gly
        915                 920                 925 cca ccc gtg tac ttt gtc ctg gag gaa ggc tat aac tac agt tca cgc      2832
Pro Pro Val Tyr Phe Val Leu Glu Glu Gly Tyr Asn Tyr Ser Ser Arg
    930                 935                 940 aaa ggg cag aac atg gtg tgc ggc ggc atg ggc tgt gac aat gac tcc      2880
Lys Gly Gln Asn Met Val Cys Gly Gly Met Gly Cys Asp Asn Asp Ser
945                 950                 955                 960 ctg gtg cag cag ata ttt aac gca gct gag ctg gac acc tac acc cga      2928
Leu Val Gln Gln Ile Phe Asn Ala Ala Glu Leu Asp Thr Tyr Thr Arg
                965                 970                 975 gta ggc ttc gcc ccc tcg tcc tgg atc gat gac tac ttt gac tgg gtc      2976
Val Gly Phe Ala Pro Ser Ser Trp Ile Asp Asp Tyr Phe Asp Trp Val
            980                 985                 990 tcg cca cag tcg tcc tgc tgc aga ctc tac aac gtc act cac cag ttc      3024
Ser Pro Gln Ser Ser Cys Cys Arg Leu Tyr Asn Val Thr His Gln Phe
        995                 1000                1005 tgc aat gct tct gtg atg gac cca acc tgt gtc cgc tgc aga cct ctg      3072
Cys Asn Ala Ser Val Met Asp Pro Thr Cys Val Arg Cys Arg Pro Leu
    1010                1015                1020 act cca gag ggt aaa cag agg cct cag ggg aaa gaa ttc atg aaa ttc      3120
Thr Pro Glu Gly Lys Gln Arg Pro Gln Gly Lys Glu Phe Met Lys Phe
1025                1030                1035                1040 ctg ccc atg ttc ctt tct gat aac ccc aac ccc aag tgc ggc aaa ggg      3168
Leu Pro Met Phe Leu Ser Asp Asn Pro Asn Pro Lys Cys Gly Lys Gly
                1045                1050                1055 gga cat gct gct tac ggt tca gct gtt aac att gtg gga gat gac act      3216
Gly His Ala Ala Tyr Gly Ser Ala Val Asn Ile Val Gly Asp Asp Thr
            1060                1065                1070 tac att ggg gcc act tac ttc atg acc tac cac acc ata ctt aag acc      3264
Tyr Ile Gly Ala Thr Tyr Phe Met Thr Tyr His Thr Ile Leu Lys Thr
        1075                1080                1085 tcc gct gac tat act gat gcc atg aag aaa gct cgg cta ata gcc agt      3312
Ser Ala Asp Tyr Thr Asp Ala Met Lys Lys Ala Arg Leu Ile Ala Ser
    1090                1095                1100 aac atc acg gaa acc atg cgt tct aag ggg agt gac tac cgc gta ttc      3360
Asn Ile Thr Glu Thr Met Arg Ser Lys Gly Ser Asp Tyr Arg Val Phe
1105                1110                1115                1120 cct tac agt gtg ttc tac gtc ttc tat gaa cag tac ctg acc att att      3408
Pro Tyr Ser Val Phe Tyr Val Phe Tyr Glu Gln Tyr Leu Thr Ile Ile
                1125                1130                1135 gat gac acc atc ttt aac ctc agt gtg tct ctg ggc tcc ata ttt ctg      3456
Asp Asp Thr Ile Phe Asn Leu Ser Val Ser Leu Gly Ser Ile Phe Leu
            1140                1145                1150 gtg acc ttg gtg gtt ctg ggc tgt gag ctg tgg tct gcg gtc atc atg      3504
Val Thr Leu Val Val Leu Gly Cys Glu Leu Trp Ser Ala Val Ile Met
        1155                1160                1165 tgt atc acc ata gcc atg atc ctg gtc aac atg ttc ggt gtc atg tgg      3552
Cys Ile Thr Ile Ala Met Ile Leu Val Asn Met Phe Gly Val Met Trp
    1170                1175                1180 ctg tgg ggc atc agt ctg aat gcg gtc tcc ttg gtc aac ttg gtg atg      3600
Leu Trp Gly Ile Ser Leu Asn Ala Val Ser Leu Val Asn Leu Val Met
1185                1190                1195                1200 agc tgt ggc att tct gtg gag ttc tgc agc cat ata acg aga gca ttc      3648
Ser Cys Gly Ile Ser Val Glu Phe Cys Ser His Ile Thr Arg Ala Phe
                1205                1210                1215 acc atg agt acc aaa gga agc cga gtg agc cgg gcg gaa gag gca ctg      3696
Thr Met Ser Thr Lys Gly Ser Arg Val Ser Arg Ala Glu Glu Ala Leu
            1220                1225                1230
```

| | | |
|---|---|---|
| gcc cac atg ggt agt tct gta ttc agt gga atc aca ctt acg aaa ttt<br>Ala His Met Gly Ser Ser Val Phe Ser Gly Ile Thr Leu Thr Lys Phe<br>       1235                 1240                1245 | | 3744 |
| gga ggg atc gtg gtg tta gcc ttt gcc aaa tct caa att ttt gag ata<br>Gly Gly Ile Val Val Leu Ala Phe Ala Lys Ser Gln Ile Phe Glu Ile<br>1250                 1255                 1260 | | 3792 |
| ttt tac ttc agg atg tac tta gcc atg gtc tta ctt gga gcc act cat<br>Phe Tyr Phe Arg Met Tyr Leu Ala Met Val Leu Leu Gly Ala Thr His<br>1265                 1270                 1275                 1280 | | 3840 |
| gga cta ata ttt ctt ccc gtc tta ctc agt tac ata ggg ccg tcg gtg<br>Gly Leu Ile Phe Leu Pro Val Leu Leu Ser Tyr Ile Gly Pro Ser Val<br>       1285                 1290                 1295 | | 3888 |
| aat aaa gct aaa aga cac acc aca tac gag cgc tac aga ggg aca gag<br>Asn Lys Ala Lys Arg His Thr Thr Tyr Glu Arg Tyr Arg Gly Thr Glu<br>       1300                 1305                 1310 | | 3936 |
| aga gaa cga ctc ctc aat ttt tag ccttgtagca ggctttggtg actgtgttta<br>Arg Glu Arg Leu Leu Asn Phe<br>       1315                 1320 | | 3990 |
| tggataggtc aagtttactg caagacagct gtgctgtcaa gactgagctg gcttcaggct | | 4050 |
| gtgtccgagc tgtgtcacat gcagctctac ccacgctttt aaactcagga atgcacacct | | 4110 |
| aacttgtgaa gcagtattaa tggatctgaa agcaacaatc gccagcccct actgtcgtac | | 4170 |
| cagtagaaac ctcatcttgg gtacaaggaa ggatagttct gtcactttaa cttgtttcaa | | 4230 |
| tgcctacttt taatggaggt tattaaacac tttaacctcc cttctagccc accaccaacc | | 4290 |
| agagatagtg ggaaagaaag gatacagggg aagtggacct gtttagaaat ggttctttgg | | 4350 |
| agcagatcct gtctgcatta tcaggaaacc agcaattcag ttcacgggtc agcagtggca | | 4410 |
| gctcgaccca ctcgcaaaca tttcacggat acaccagcag tgttgggata ggagcagcca | | 4470 |
| ggcctcagca ggagggacca gggccgacag gaacaccaga ggttcttggc tgttcctcta | | 4530 |
| tcagcgaaga ctggagacca acaaacatta cacagctagc tctatattct ctctgtggag | | 4590 |
| tcccaacaca tggagctcaa ctacacaata taaggcagac caaccaatac atgcctgtca | | 4650 |
| ttcacgtgtc ctttcatgtg cttgctttag ggaaacagtc cttcacaagt ctgccttttca | | 4710 |
| cctgtgtctg cttcagcaaa atgttctttc acatttgccc cagcaaaacc ccatctaaca | | 4770 |
| caactgactt tccaaagaac ccttaagttt ccatttccca gtggcaataa ctgtgacctg | | 4830 |
| atccctagcc cacatgctgt ctcctttttct gggagttagc aacatttgag gatgttgtag | | 4890 |
| gtactttatt acatttttt gtagtttaaa gagcttatt aatgcaataa attaactttg | | 4950 |
| tacattttta tattaaaaaa aaaaagact attaagggac ttcagaatgt tgtaggcctc | | 5010 |
| attaggcttg tctcagccg | | 5029 |

<210> SEQ ID NO 4
<211> LENGTH: 1319
<212> TYPE: PRT
<213> ORGANISM: Mus sp.

<400> SEQUENCE: 4

Val Cys Ser Cys Pro Leu Leu Gly Gln Ala Pro Val Pro Lys Pro Cys
 1               5                  10                  15

Pro Pro Val Pro Arg Arg Ser Gly Arg Gly Ala Pro Arg Ala Glu Leu
            20                  25                  30

Arg Ala Val Ala Pro Arg Gly Asp Ser Met Gly Ala His His Pro Ala
        35                  40                  45

Leu Gly Leu Leu Leu Leu Leu Leu Cys Pro Ala Gln Val Phe Ser
    50                  55                  60

```
Gln Ser Cys Val Trp Tyr Gly Glu Cys Gly Ile Ala Thr Gly Asp Lys
 65                  70                  75                  80

Arg Tyr Asn Cys Lys Tyr Ser Gly Pro Pro Lys Pro Leu Pro Lys Asp
                 85                  90                  95

Gly Tyr Asp Leu Val Gln Glu Leu Cys Pro Gly Leu Phe Phe Asp Asn
            100                 105                 110

Val Ser Leu Cys Cys Asp Ile Gln Gln Leu Gln Thr Leu Lys Ser Asn
            115                 120                 125

Leu Gln Leu Pro Leu Gln Phe Leu Ser Arg Cys Pro Ser Cys Phe Tyr
    130                 135                 140

Asn Leu Met Thr Leu Phe Cys Glu Leu Thr Cys Ser Pro His Gln Ser
145                 150                 155                 160

Gln Phe Leu Asn Val Thr Ala Thr Glu Asp Tyr Phe Asp Pro Lys Thr
                165                 170                 175

Pro Glu Asn Lys Thr Asn Val Lys Glu Leu Glu Tyr Tyr Val Gly Gln
            180                 185                 190

Ser Phe Ala Asn Ala Met Tyr Asn Ala Cys Arg Asp Val Glu Ala Pro
            195                 200                 205

Ser Ser Asn Glu Lys Ala Leu Gly Leu Leu Cys Gly Arg Asp Ala Arg
    210                 215                 220

Ala Cys Asn Ala Thr Asn Trp Ile Glu Tyr Met Phe Asn Lys Asp Asn
225                 230                 235                 240

Gly Gln Ala Pro Phe Thr Ile Ile Pro Val Phe Ser Asp Leu Ser Ile
                245                 250                 255

Leu Gly Met Glu Pro Met Arg Asn Ala Thr Lys Gly Cys Asn Glu Ser
            260                 265                 270

Val Asp Glu Val Thr Gly Pro Cys Ser Cys Gln Asp Cys Ser Ile Val
            275                 280                 285

Cys Gly Pro Lys Pro Gln Ile Leu Gln Gly Ile Gly Gly Gly Gly Gly
    290                 295                 300

Trp Gly Leu Asp Ala Met Tyr Val Ile Met Trp Val Thr Tyr Val Ala
305                 310                 315                 320

Phe Leu Phe Val Phe Phe Gly Ala Leu Leu Ala Val Trp Cys His Arg
                325                 330                 335

Arg Arg Tyr Phe Val Ser Glu Tyr Thr Pro Ile Asp Ser Asn Ile Ala
            340                 345                 350

Phe Ser Val Asn Ser Ser Asp Lys Gly Glu Ala Ser Cys Cys Asp Pro
            355                 360                 365

Leu Gly Ala Ala Phe Asp Asp Cys Leu Arg Arg Met Phe Thr Lys Trp
    370                 375                 380

Gly Ala Phe Cys Val Arg Asn Pro Thr Cys Ile Ile Phe Phe Ser Leu
385                 390                 395                 400

Ala Phe Ile Thr Val Cys Ser Ser Gly Leu Val Phe Val Gln Val Thr
                405                 410                 415

Thr Asn Pro Val Glu Leu Trp Ser Ala Pro His Ser Gln Ala Arg Leu
            420                 425                 430

Glu Lys Glu Tyr Phe Asp Lys His Phe Gly Pro Phe Phe Arg Thr Glu
            435                 440                 445

Gln Leu Ile Ile Gln Ala Pro Asn Thr Ser Val His Ile Tyr Glu Pro
    450                 455                 460

Tyr Pro Ala Gly Ala Asp Val Pro Phe Gly Pro Pro Leu Asn Lys Glu
465                 470                 475                 480
```

-continued

```
Ile Leu His Gln Val Leu Asn Leu Gln Ile Ala Ile Glu Ser Ile Thr
                485                 490                 495
Ala Ser Tyr Asn Asn Glu Thr Val Thr Leu Gln Asp Ile Cys Val Ala
            500                 505                 510
Pro Leu Ser Pro Tyr Asn Lys Asn Cys Thr Ile Met Ser Val Leu Asn
        515                 520                 525
Tyr Phe Gln Asn Ser His Ala Val Leu Asp Ser Gln Val Gly Asp Asp
    530                 535                 540
Phe Tyr Ile Tyr Ala Asp Tyr His Thr His Phe Leu Tyr Cys Val Arg
545                 550                 555                 560
Ala Pro Ala Ser Leu Asn Asp Thr Ser Leu Leu His Gly Pro Cys Leu
                565                 570                 575
Gly Thr Phe Gly Gly Pro Val Phe Pro Trp Leu Val Leu Gly Gly Tyr
            580                 585                 590
Asp Asp Gln Asn Tyr Asn Asn Ala Thr Ala Leu Val Ile Thr Phe Pro
        595                 600                 605
Val Asn Asn Tyr Tyr Asn Asp Thr Glu Arg Leu Gln Arg Ala Trp Ala
    610                 615                 620
Trp Glu Lys Glu Phe Ile Ser Phe Val Lys Asn Tyr Lys Asn Pro Asn
625                 630                 635                 640
Leu Thr Ile Ser Phe Thr Ala Glu Arg Ser Ile Glu Asp Glu Leu Asn
                645                 650                 655
Arg Glu Ser Asn Ser Asp Val Phe Thr Val Ile Ser Tyr Val Val
            660                 665                 670
Met Phe Leu Tyr Ile Ser Leu Ala Leu Gly His Ile Gln Ser Cys Ser
        675                 680                 685
Arg Leu Leu Val Asp Ser Lys Ile Ser Leu Gly Ile Ala Gly Ile Leu
    690                 695                 700
Ile Val Leu Ser Ser Val Ala Cys Ser Leu Gly Ile Phe Ser Tyr Met
705                 710                 715                 720
Gly Met Pro Leu Thr Leu Ile Val Ile Glu Val Ile Pro Phe Leu Val
                725                 730                 735
Leu Ala Val Gly Val Asp Asn Ile Phe Ile Leu Val Gln Thr Tyr Gln
            740                 745                 750
Arg Asp Glu Arg Leu Gln Glu Glu Thr Leu Asp Gln Gln Leu Gly Arg
        755                 760                 765
Ile Leu Gly Glu Val Ala Pro Thr Met Phe Leu Ser Ser Phe Ser Glu
    770                 775                 780
Thr Ser Ala Phe Phe Phe Gly Ala Leu Ser Ser Met Pro Ala Val His
785                 790                 795                 800
Thr Phe Ser Leu Phe Ala Gly Met Ala Val Leu Ile Asp Phe Leu Leu
                805                 810                 815
Gln Ile Thr Cys Phe Val Ser Leu Leu Gly Leu Asp Ile Lys Arg Gln
            820                 825                 830
Glu Lys Asn His Leu Asp Ile Leu Cys Cys Val Arg Gly Ala Asp Asp
        835                 840                 845
Gly Gln Gly Ser His Ala Ser Glu Ser Tyr Leu Phe Arg Phe Phe Lys
    850                 855                 860
Asn Tyr Phe Ala Pro Leu Leu Leu Lys Asp Trp Leu Arg Pro Ile Val
865                 870                 875                 880
Val Ala Val Phe Val Gly Val Leu Ser Phe Ser Val Ala Val Val Asn
                885                 890                 895
Lys Val Asp Ile Gly Leu Asp Gln Ser Leu Ser Met Pro Asn Asp Ser
```

-continued

```
                900             905             910
Tyr Val Ile Ala Asn Phe Lys Ser Leu Ala Gln Tyr Leu His Ser Gly
            915                 920             925

Pro Pro Val Tyr Phe Val Leu Glu Glu Gly Tyr Asn Tyr Ser Ser Arg
        930                 935             940

Lys Gly Gln Asn Met Val Cys Gly Gly Met Gly Cys Asp Asn Asp Ser
945                 950             955                 960

Leu Val Gln Gln Ile Phe Asn Ala Ala Glu Leu Asp Thr Tyr Thr Arg
                965                 970             975

Val Gly Phe Ala Pro Ser Ser Trp Ile Asp Asp Tyr Phe Asp Trp Val
            980                 985             990

Ser Pro Gln Ser Ser Cys Cys Arg Leu Tyr Asn Val Thr His Gln Phe
        995                 1000            1005

Cys Asn Ala Ser Val Met Asp Pro Thr Cys Val Arg Cys Arg Pro Leu
    1010                1015            1020

Thr Pro Glu Gly Lys Gln Arg Pro Gln Gly Lys Glu Phe Met Lys Phe
1025                1030            1035            1040

Leu Pro Met Phe Leu Ser Asp Asn Pro Asn Pro Lys Cys Gly Lys Gly
            1045                1050            1055

Gly His Ala Ala Tyr Gly Ser Ala Val Asn Ile Val Gly Asp Asp Thr
            1060                1065            1070

Tyr Ile Gly Ala Thr Tyr Phe Met Thr Tyr His Thr Ile Leu Lys Thr
            1075                1080            1085

Ser Ala Asp Tyr Thr Asp Ala Met Lys Lys Ala Arg Leu Ile Ala Ser
    1090                1095            1100

Asn Ile Thr Glu Thr Met Arg Ser Lys Gly Ser Asp Tyr Arg Val Phe
1105                1110            1115            1120

Pro Tyr Ser Val Phe Tyr Val Phe Tyr Glu Gln Tyr Leu Thr Ile Ile
            1125                1130            1135

Asp Asp Thr Ile Phe Asn Leu Ser Val Ser Leu Gly Ser Ile Phe Leu
            1140                1145            1150

Val Thr Leu Val Val Leu Gly Cys Glu Leu Trp Ser Ala Val Ile Met
            1155                1160            1165

Cys Ile Thr Ile Ala Met Ile Leu Val Asn Met Phe Gly Val Met Trp
    1170                1175            1180

Leu Trp Gly Ile Ser Leu Asn Ala Val Ser Leu Val Asn Leu Val Met
1185                1190            1195            1200

Ser Cys Gly Ile Ser Val Glu Phe Cys Ser His Ile Thr Arg Ala Phe
            1205                1210            1215

Thr Met Ser Thr Lys Gly Ser Arg Val Ser Arg Ala Glu Glu Ala Leu
            1220                1225            1230

Ala His Met Gly Ser Ser Val Phe Ser Gly Ile Thr Leu Thr Lys Phe
    1235                1240            1245

Gly Gly Ile Val Val Leu Ala Phe Ala Lys Ser Gln Ile Phe Glu Ile
    1250                1255            1260

Phe Tyr Phe Arg Met Tyr Leu Ala Met Val Leu Leu Gly Ala Thr His
1265                1270            1275            1280

Gly Leu Ile Phe Leu Pro Val Leu Leu Ser Tyr Ile Gly Pro Ser Val
            1285                1290            1295

Asn Lys Ala Lys Arg His Thr Thr Tyr Glu Arg Tyr Arg Gly Thr Glu
            1300                1305            1310

Arg Glu Arg Leu Leu Asn Phe
            1315
```

<210> SEQ ID NO 5
<211> LENGTH: 3540
<212> TYPE: DNA
<213> ORGANISM: Saccharomyces cerevisiae
<220> FEATURE:
<221> NAME/KEY: CDS
<222> LOCATION: (1)..(3513)

<400> SEQUENCE: 5

| | | |
|---|---|---|
| atg aat gtg cta tgg att ata gca cta gtt ggc cag ctg atg cgg ctc<br>Met Asn Val Leu Trp Ile Ile Ala Leu Val Gly Gln Leu Met Arg Leu<br>1                   5                      10                  15 | | 48 |
| gtt cag gga aca gct acc tgt gcc atg tat ggg aac tgt ggg aaa aag<br>Val Gln Gly Thr Ala Thr Cys Ala Met Tyr Gly Asn Cys Gly Lys Lys<br>                   20                      25                      30 | | 96 |
| tca gta ttt gga aac gaa tta cct tgc cct gtg cca cgt agt ttt gaa<br>Ser Val Phe Gly Asn Glu Leu Pro Cys Pro Val Pro Arg Ser Phe Glu<br>               35                      40                      45 | | 144 |
| cct cct gtt ctt tca gat gaa aca agc aaa ctt ttg gtt gaa gtt tgt<br>Pro Pro Val Leu Ser Asp Glu Thr Ser Lys Leu Leu Val Glu Val Cys<br>50                       55                      60 | | 192 |
| ggt gaa gag tgg aaa gag gtc cgt tat gcc tgc tgt act aaa gat caa<br>Gly Glu Glu Trp Lys Glu Val Arg Tyr Ala Cys Cys Thr Lys Asp Gln<br>65                       70                      75                      80 | | 240 |
| gtg gta gca ctg aga gat aac cta caa aag gct caa cct tta att tcc<br>Val Val Ala Leu Arg Asp Asn Leu Gln Lys Ala Gln Pro Leu Ile Ser<br>                   85                      90                      95 | | 288 |
| tca tgc cca gca tgc ctc aag aat ttt aat aac ctg ttc tgt cac ttc<br>Ser Cys Pro Ala Cys Leu Lys Asn Phe Asn Asn Leu Phe Cys His Phe<br>                 100                    105                 110 | | 336 |
| act tgc gct gct gac caa gga agg ttt gtc aat att acc aag gta gaa<br>Thr Cys Ala Ala Asp Gln Gly Arg Phe Val Asn Ile Thr Lys Val Glu<br>               115                   120                   125 | | 384 |
| aag tca aaa gaa gat aaa gat att gtt gcg gaa tta gac gtt ttc atg<br>Lys Ser Lys Glu Asp Lys Asp Ile Val Ala Glu Leu Asp Val Phe Met<br>130                 135                 140 | | 432 |
| aat tcg tct tgg gca tct gaa ttt tat gac tca tgt aag aat att aaa<br>Asn Ser Ser Trp Ala Ser Glu Phe Tyr Asp Ser Cys Lys Asn Ile Lys<br>145                 150                 155                 160 | | 480 |
| ttt tct gct acc aac ggt tat gcg atg gac cta atc gga ggt ggt gct<br>Phe Ser Ala Thr Asn Gly Tyr Ala Met Asp Leu Ile Gly Gly Gly Ala<br>                 165                    170                 175 | | 528 |
| aaa aat tac agt caa ttc ttg aag ttt ttg ggg gat gct aaa cct atg<br>Lys Asn Tyr Ser Gln Phe Leu Lys Phe Leu Gly Asp Ala Lys Pro Met<br>                 180                    185                 190 | | 576 |
| ctt ggt gga tcc ccc ttt cag att aat tac aag tat gat tta gca aat<br>Leu Gly Gly Ser Pro Phe Gln Ile Asn Tyr Lys Tyr Asp Leu Ala Asn<br>               195                   200                   205 | | 624 |
| gaa gaa aaa gaa tgg cag gaa ttt aat gat gag gtt tat gct tgc gat<br>Glu Glu Lys Glu Trp Gln Glu Phe Asn Asp Glu Val Tyr Ala Cys Asp<br>210                 215                 220 | | 672 |
| gat gct caa tat aaa tgt gcg tgt tct gat tgt caa gag tct tgc ccc<br>Asp Ala Gln Tyr Lys Cys Ala Cys Ser Asp Cys Gln Glu Ser Cys Pro<br>225                 230                 235                 240 | | 720 |
| cat tta aaa cct tta aaa gat ggc gtg tgt aaa gtt ggc cct ctg cca<br>His Leu Lys Pro Leu Lys Asp Gly Val Cys Lys Val Gly Pro Leu Pro<br>                 245                    250                 255 | | 768 |
| tgt ttt tcc ctt tct gtt ctg atc ttt tac aca atc tgt gca ctt ttt<br>Cys Phe Ser Leu Ser Val Leu Ile Phe Tyr Thr Ile Cys Ala Leu Phe<br>                 260                    265                 270 | | 816 |

-continued

| | | |
|---|---|---|
| gca ttt atg tgg tat tat ctc tgt aaa aga aaa aaa aac ggg gca atg<br>Ala Phe Met Trp Tyr Tyr Leu Cys Lys Arg Lys Lys Asn Gly Ala Met<br>275 280 285 | 864 | |
| att gtg gac gac gat att gtt cca gaa tca ggt tcc tta gat gaa tca<br>Ile Val Asp Asp Asp Ile Val Pro Glu Ser Gly Ser Leu Asp Glu Ser<br>290 295 300 | 912 | |
| gag acg aat gta ttc gaa agt ttc aat aat gaa act aac ttt ttt aat<br>Glu Thr Asn Val Phe Glu Ser Phe Asn Asn Glu Thr Asn Phe Phe Asn<br>305 310 315 320 | 960 | |
| ggt aaa ctc gct aac cta ttt acg aaa gtg gga caa ttt tcc gtt gaa<br>Gly Lys Leu Ala Asn Leu Phe Thr Lys Val Gly Gln Phe Ser Val Glu<br>325 330 335 | 1008 | |
| aac ccc tac aag ata tta ata acc act gtt ttt agt atc ttt gta ttc<br>Asn Pro Tyr Lys Ile Leu Ile Thr Thr Val Phe Ser Ile Phe Val Phe<br>340 345 350 | 1056 | |
| agt ttc atc ata ttt cag tac gct act ctt gaa aca gat cca att aat<br>Ser Phe Ile Ile Phe Gln Tyr Ala Thr Leu Glu Thr Asp Pro Ile Asn<br>355 360 365 | 1104 | |
| ttg tgg gtg agt aaa aat tct gaa aaa ttc aaa gaa aaa gag tac ttc<br>Leu Trp Val Ser Lys Asn Ser Glu Lys Phe Lys Glu Lys Glu Tyr Phe<br>370 375 380 | 1152 | |
| gat gat aat ttt ggg cca ttt tac agg aca gag caa ata ttt gtt gtg<br>Asp Asp Asn Phe Gly Pro Phe Tyr Arg Thr Glu Gln Ile Phe Val Val<br>385 390 395 400 | 1200 | |
| aat gag aca ggc cct gtg tta tca tat gag aca ctt cac tgg tgg ttt<br>Asn Glu Thr Gly Pro Val Leu Ser Tyr Glu Thr Leu His Trp Trp Phe<br>405 410 415 | 1248 | |
| gac gtt gaa aat ttt att acg gaa gag cta caa tcg tca gaa aat att<br>Asp Val Glu Asn Phe Ile Thr Glu Glu Leu Gln Ser Ser Glu Asn Ile<br>420 425 430 | 1296 | |
| gga tac caa gat ctc tgc ttc aga cca aca gaa gat tct aca tgc gta<br>Gly Tyr Gln Asp Leu Cys Phe Arg Pro Thr Glu Asp Ser Thr Cys Val<br>435 440 445 | 1344 | |
| ata gag tct ttt act cag tat ttt cag ggg gcc tta cca aac aag gat<br>Ile Glu Ser Phe Thr Gln Tyr Phe Gln Gly Ala Leu Pro Asn Lys Asp<br>450 455 460 | 1392 | |
| agc tgg aaa agg gaa ctg cag gaa tgt ggg aaa ttt cct gta aac tgt<br>Ser Trp Lys Arg Glu Leu Gln Glu Cys Gly Lys Phe Pro Val Asn Cys<br>465 470 475 480 | 1440 | |
| cta cct act ttc cag caa cct cta aaa act aat ctt ctt ttc agt gac<br>Leu Pro Thr Phe Gln Gln Pro Leu Lys Thr Asn Leu Leu Phe Ser Asp<br>485 490 495 | 1488 | |
| gat gat att ctc aat gcg cat gcg ttt gtt gta aca ctt cta ttg acc<br>Asp Asp Ile Leu Asn Ala His Ala Phe Val Val Thr Leu Leu Leu Thr<br>500 505 510 | 1536 | |
| aac cac act caa tca gct aat cgc tgg gaa gaa aga ttg gaa gag tat<br>Asn His Thr Gln Ser Ala Asn Arg Trp Glu Glu Arg Leu Glu Glu Tyr<br>515 520 525 | 1584 | |
| tta ttg gat tta aag gtc ccc gag ggc ctg agg atc agt ttt aat acc<br>Leu Leu Asp Leu Lys Val Pro Glu Gly Leu Arg Ile Ser Phe Asn Thr<br>530 535 540 | 1632 | |
| gaa ata tcc ttg gaa aaa gag ctt aat aat aat aat gat atc tcg acc<br>Glu Ile Ser Leu Glu Lys Glu Leu Asn Asn Asn Asn Asp Ile Ser Thr<br>545 550 555 560 | 1680 | |
| gtt gca ata tca tac ctg atg atg ttt tta tat gct aca tgg gcc ttg<br>Val Ala Ile Ser Tyr Leu Met Met Phe Leu Tyr Ala Thr Trp Ala Leu<br>565 570 575 | 1728 | |
| agg aga aag gat ggg aaa act agg ttg tta ctt gga ata tct ggt tta<br>Arg Arg Lys Asp Gly Lys Thr Arg Leu Leu Leu Gly Ile Ser Gly Leu | 1776 | |

-continued

| | | | | | | | | | | | | | | | |
|---|---|---|---|---|---|---|---|---|---|---|---|---|---|---|---|
| | | | 580 | | | | | 585 | | | | | 590 | | |
| ctc | ata | gtt | ttg | gct | tct | att | gtt | tgt | gca | gcc | gga | ttt | tta | act | ctt | 1824 |
| Leu | Ile | Val | Leu | Ala | Ser | Ile | Val | Cys | Ala | Ala | Gly | Phe | Leu | Thr | Leu |
| | | | 595 | | | | | 600 | | | | | 605 | | |
| ttt | ggt | ttg | aag | tcg | aca | ttg | atc | ata | gca | gaa | gta | ata | ccg | ttt | cta | 1872 |
| Phe | Gly | Leu | Lys | Ser | Thr | Leu | Ile | Ile | Ala | Glu | Val | Ile | Pro | Phe | Leu |
| | | | 610 | | | | | 615 | | | | | 620 | | |
| att | tta | gca | ata | gga | ata | gat | aat | att | ttc | ttg | att | aca | cat | gag | tat | 1920 |
| Ile | Leu | Ala | Ile | Gly | Ile | Asp | Asn | Ile | Phe | Leu | Ile | Thr | His | Glu | Tyr |
| 625 | | | | | 630 | | | | | 635 | | | | | 640 |
| gat | aga | aat | tgc | gag | caa | aaa | ccg | gag | tat | tca | att | gat | caa | aaa | ata | 1968 |
| Asp | Arg | Asn | Cys | Glu | Gln | Lys | Pro | Glu | Tyr | Ser | Ile | Asp | Gln | Lys | Ile |
| | | | | 645 | | | | | 650 | | | | | 655 | |
| ata | agc | gct | atc | ggg | aga | atg | tct | cct | tcc | att | tta | atg | tca | ttg | cta | 2016 |
| Ile | Ser | Ala | Ile | Gly | Arg | Met | Ser | Pro | Ser | Ile | Leu | Met | Ser | Leu | Leu |
| | | | | 660 | | | | | 665 | | | | | 670 | |
| tgt | caa | acc | gga | tgc | ttc | ttg | ata | gct | gca | ttt | gtt | aca | atg | cca | gct | 2064 |
| Cys | Gln | Thr | Gly | Cys | Phe | Leu | Ile | Ala | Ala | Phe | Val | Thr | Met | Pro | Ala |
| | | | 675 | | | | | 680 | | | | | 685 | | |
| gtc | cat | aat | ttt | gct | ata | tat | tcc | aca | gtt | tct | gtt | ata | ttc | aac | gga | 2112 |
| Val | His | Asn | Phe | Ala | Ile | Tyr | Ser | Thr | Val | Ser | Val | Ile | Phe | Asn | Gly |
| | | | 690 | | | | | 695 | | | | | 700 | | |
| gta | tta | cag | cta | aca | gcg | tat | gtg | tcc | att | ttg | tct | ctc | tac | gaa | aag | 2160 |
| Val | Leu | Gln | Leu | Thr | Ala | Tyr | Val | Ser | Ile | Leu | Ser | Leu | Tyr | Glu | Lys |
| 705 | | | | | 710 | | | | | 715 | | | | | 720 |
| aga | tcc | aat | tat | aaa | caa | att | acc | gga | aat | gaa | gaa | act | aag | gaa | tca | 2208 |
| Arg | Ser | Asn | Tyr | Lys | Gln | Ile | Thr | Gly | Asn | Glu | Glu | Thr | Lys | Glu | Ser |
| | | | | 725 | | | | | 730 | | | | | 735 | |
| ttt | ttg | aaa | acg | ttt | tat | ttt | aag | atg | tta | acg | caa | aag | agg | ctc | ata | 2256 |
| Phe | Leu | Lys | Thr | Phe | Tyr | Phe | Lys | Met | Leu | Thr | Gln | Lys | Arg | Leu | Ile |
| | | | 740 | | | | | 745 | | | | | 750 | | |
| atc | att | atc | ttc | tcg | gct | tgg | ttt | ttc | aca | tct | ctg | gtt | ttc | tta | cca | 2304 |
| Ile | Ile | Ile | Phe | Ser | Ala | Trp | Phe | Phe | Thr | Ser | Leu | Val | Phe | Leu | Pro |
| | | | 755 | | | | | 760 | | | | | 765 | | |
| gaa | att | caa | ttt | ggg | cta | gat | caa | aca | ttg | gct | gtt | cca | cag | gat | tcc | 2352 |
| Glu | Ile | Gln | Phe | Gly | Leu | Asp | Gln | Thr | Leu | Ala | Val | Pro | Gln | Asp | Ser |
| | 770 | | | | | 775 | | | | | 780 | | | | |
| tac | ctg | gtt | gac | tat | ttt | aag | gat | gtt | tat | agc | ttc | cta | aac | gta | gga | 2400 |
| Tyr | Leu | Val | Asp | Tyr | Phe | Lys | Asp | Val | Tyr | Ser | Phe | Leu | Asn | Val | Gly |
| 785 | | | | | 790 | | | | | 795 | | | | | 800 |
| cca | ccg | gtt | tac | atg | gtc | gtg | aag | aat | tta | gat | ttg | act | aaa | aga | caa | 2448 |
| Pro | Pro | Val | Tyr | Met | Val | Val | Lys | Asn | Leu | Asp | Leu | Thr | Lys | Arg | Gln |
| | | | | 805 | | | | | 810 | | | | | 815 | |
| aac | caa | cag | aaa | ata | tgt | ggt | aaa | ttt | aca | act | tgc | gaa | aga | gac | tca | 2496 |
| Asn | Gln | Gln | Lys | Ile | Cys | Gly | Lys | Phe | Thr | Thr | Cys | Glu | Arg | Asp | Ser |
| | | | 820 | | | | | 825 | | | | | 830 | | |
| tta | gct | aat | gta | ctg | gag | caa | gaa | aga | cac | agg | tca | aca | att | acg | gag | 2544 |
| Leu | Ala | Asn | Val | Leu | Glu | Gln | Glu | Arg | His | Arg | Ser | Thr | Ile | Thr | Glu |
| | | | 835 | | | | | 840 | | | | | 845 | | |
| cca | ttg | gct | aat | tgg | ctg | gac | gat | tat | ttc | atg | ttt | tta | aat | cct | caa | 2592 |
| Pro | Leu | Ala | Asn | Trp | Leu | Asp | Asp | Tyr | Phe | Met | Phe | Leu | Asn | Pro | Gln |
| | 850 | | | | | 855 | | | | | 860 | | | | |
| aac | gac | cag | tgt | tgt | aga | tta | aag | aag | gga | aca | gat | gag | gtt | tgt | cct | 2640 |
| Asn | Asp | Gln | Cys | Cys | Arg | Leu | Lys | Lys | Gly | Thr | Asp | Glu | Val | Cys | Pro |
| 865 | | | | | 870 | | | | | 875 | | | | | 880 |
| ccc | tct | ttt | cca | agt | aga | cgt | tgt | gaa | act | tgt | ttc | cag | cag | ggt | tct | 2688 |
| Pro | Ser | Phe | Pro | Ser | Arg | Arg | Cys | Glu | Thr | Cys | Phe | Gln | Gln | Gly | Ser |
| | | | | 885 | | | | | 890 | | | | | 895 | |
| tgg | aat | tac | aac | atg | tca | ggg | ttt | cct | gag | ggc | aag | gac | ttc | atg | gaa | 2736 |

-continued

```
Trp Asn Tyr Asn Met Ser Gly Phe Pro Glu Gly Lys Asp Phe Met Glu
        900                 905                 910
tac cta agc ata tgg att aat gcg cct agt gac ccc tgc cct cta ggt      2784
Tyr Leu Ser Ile Trp Ile Asn Ala Pro Ser Asp Pro Cys Pro Leu Gly
915                 920                 925
ggt cgt gcg cca tat tcg act gcg tta gtt tat aat gaa acg agt gtg      2832
Gly Arg Ala Pro Tyr Ser Thr Ala Leu Val Tyr Asn Glu Thr Ser Val
        930                 935                 940
tct gcg tca gtt ttc aga aca gct cat cat cct ttg aga tcc caa aag      2880
Ser Ala Ser Val Phe Arg Thr Ala His His Pro Leu Arg Ser Gln Lys
945                 950                 955                 960
gac ttt atc cag gcg tat agt gat gga gtt agg ata tca agt tct ttc      2928
Asp Phe Ile Gln Ala Tyr Ser Asp Gly Val Arg Ile Ser Ser Ser Phe
                965                 970                 975
ccc gaa cta gat atg ttt gca tac tcg ccg ttt tac att ttt ttt gtt      2976
Pro Glu Leu Asp Met Phe Ala Tyr Ser Pro Phe Tyr Ile Phe Phe Val
            980                 985                 990
caa tat caa act ttg gga cca ttg acg ttg aag cta ata ggg agt gcc      3024
Gln Tyr Gln Thr Leu Gly Pro Leu Thr Leu Lys Leu Ile Gly Ser Ala
        995                 1000                1005
att atc cta att ttt ttc att tca tct gtt ttc ttg cag aat ata cgc      3072
Ile Ile Leu Ile Phe Phe Ile Ser Ser Val Phe Leu Gln Asn Ile Arg
    1010                1015                1020
agc tca ttc tta ctg gct ttg gtc gtt acc atg att atc gta gat att      3120
Ser Ser Phe Leu Leu Ala Leu Val Val Thr Met Ile Ile Val Asp Ile
1025                1030                1035                1040
ggt gct ttg atg gcc cta cta ggt atc tca ctc aac gct gtc agt tta      3168
Gly Ala Leu Met Ala Leu Leu Gly Ile Ser Leu Asn Ala Val Ser Leu
                1045                1050                1055
gtc aat tta att att tgt gtc ggt ttg ggt gtc gag ttt tgt gtt cat      3216
Val Asn Leu Ile Ile Cys Val Gly Leu Gly Val Glu Phe Cys Val His
            1060                1065                1070
att gtt aga tca ttt aca gtg gtc ccc agt gaa acc aag aaa gac gca      3264
Ile Val Arg Ser Phe Thr Val Val Pro Ser Glu Thr Lys Lys Asp Ala
        1075                1080                1085
aac tca aga gtt ctc tat tcc ttg aat acc ata ggt gag tcc gtc atc      3312
Asn Ser Arg Val Leu Tyr Ser Leu Asn Thr Ile Gly Glu Ser Val Ile
    1090                1095                1100
aaa ggt ata act cta acc aaa ttc att gga gtt tgt gta ctt gca ttc      3360
Lys Gly Ile Thr Leu Thr Lys Phe Ile Gly Val Cys Val Leu Ala Phe
1105                1110                1115                1120
gcc caa tcg aaa ata ttt gat gta ttt tac ttt aga atg tgg ttt aca      3408
Ala Gln Ser Lys Ile Phe Asp Val Phe Tyr Phe Arg Met Trp Phe Thr
                1125                1130                1135
cta atc att gta gca gca ttg cat gct ctc cta ttt tta cct gct tta      3456
Leu Ile Ile Val Ala Ala Leu His Ala Leu Leu Phe Leu Pro Ala Leu
            1140                1145                1150
ctt tca ttg ttt ggt ggt gaa agc tat agg gac gat tcc atc gaa gca      3504
Leu Ser Leu Phe Gly Gly Glu Ser Tyr Arg Asp Asp Ser Ile Glu Ala
        1155                1160                1165
gaa gat tag ccatagcaga ttatactata ttttacg                            3540
Glu Asp
1170

<210> SEQ ID NO 6
<211> LENGTH: 1170
<212> TYPE: PRT
<213> ORGANISM: Saccharomyces cerevisiae

<400> SEQUENCE: 6
```

-continued

```
Met Asn Val Leu Trp Ile Ile Ala Leu Val Gly Gln Leu Met Arg Leu
 1               5                  10                  15

Val Gln Gly Thr Ala Thr Cys Ala Met Tyr Gly Asn Cys Gly Lys Lys
                 20                  25                  30

Ser Val Phe Gly Asn Glu Leu Pro Cys Pro Val Pro Arg Ser Phe Glu
             35                  40                  45

Pro Pro Val Leu Ser Asp Glu Thr Ser Lys Leu Leu Val Glu Val Cys
         50                  55                  60

Gly Glu Glu Trp Lys Glu Val Arg Tyr Ala Cys Cys Thr Lys Asp Gln
 65                  70                  75                  80

Val Val Ala Leu Arg Asp Asn Leu Gln Lys Ala Gln Pro Leu Ile Ser
                 85                  90                  95

Ser Cys Pro Ala Cys Leu Lys Asn Phe Asn Asn Leu Phe Cys His Phe
             100                 105                 110

Thr Cys Ala Ala Asp Gln Gly Arg Phe Val Asn Ile Thr Lys Val Glu
             115                 120                 125

Lys Ser Lys Glu Asp Lys Asp Ile Val Ala Glu Leu Asp Val Phe Met
 130                 135                 140

Asn Ser Ser Trp Ala Ser Glu Phe Tyr Asp Ser Cys Lys Asn Ile Lys
145                 150                 155                 160

Phe Ser Ala Thr Asn Gly Tyr Ala Met Asp Leu Ile Gly Gly Gly Ala
                 165                 170                 175

Lys Asn Tyr Ser Gln Phe Leu Lys Phe Leu Gly Asp Ala Lys Pro Met
             180                 185                 190

Leu Gly Gly Ser Pro Phe Gln Ile Asn Tyr Lys Tyr Asp Leu Ala Asn
             195                 200                 205

Glu Glu Lys Glu Trp Gln Glu Phe Asn Asp Glu Val Tyr Ala Cys Asp
 210                 215                 220

Asp Ala Gln Tyr Lys Cys Ala Cys Ser Asp Cys Gln Glu Ser Cys Pro
225                 230                 235                 240

His Leu Lys Pro Leu Lys Asp Gly Val Cys Lys Val Gly Pro Leu Pro
                 245                 250                 255

Cys Phe Ser Leu Ser Val Leu Ile Phe Tyr Thr Ile Cys Ala Leu Phe
             260                 265                 270

Ala Phe Met Trp Tyr Tyr Leu Cys Lys Arg Lys Lys Asn Gly Ala Met
             275                 280                 285

Ile Val Asp Asp Asp Ile Val Pro Glu Ser Gly Ser Leu Asp Glu Ser
 290                 295                 300

Glu Thr Asn Val Phe Glu Ser Phe Asn Asn Glu Thr Asn Phe Phe Asn
305                 310                 315                 320

Gly Lys Leu Ala Asn Leu Phe Thr Lys Val Gly Gln Phe Ser Val Glu
                 325                 330                 335

Asn Pro Tyr Lys Ile Leu Ile Thr Thr Val Phe Ser Ile Phe Val Phe
             340                 345                 350

Ser Phe Ile Ile Phe Gln Tyr Ala Thr Leu Glu Thr Asp Pro Ile Asn
             355                 360                 365

Leu Trp Val Ser Lys Asn Ser Glu Lys Phe Lys Glu Lys Glu Tyr Phe
 370                 375                 380

Asp Asp Asn Phe Gly Pro Phe Tyr Arg Thr Glu Gln Ile Phe Val Val
385                 390                 395                 400

Asn Glu Thr Gly Pro Val Leu Ser Tyr Glu Thr Leu His Trp Trp Phe
                 405                 410                 415

Asp Val Glu Asn Phe Ile Thr Glu Glu Leu Gln Ser Ser Glu Asn Ile
```

-continued

```
                    420               425               430
Gly Tyr Gln Asp Leu Cys Phe Arg Pro Thr Glu Asp Ser Thr Cys Val
                435               440               445
Ile Glu Ser Phe Thr Gln Tyr Phe Gln Gly Ala Leu Pro Asn Lys Asp
450               455               460
Ser Trp Lys Arg Glu Leu Gln Glu Cys Gly Lys Phe Pro Val Asn Cys
465               470               475               480
Leu Pro Thr Phe Gln Gln Pro Leu Lys Thr Asn Leu Leu Phe Ser Asp
                485               490               495
Asp Asp Ile Leu Asn Ala His Ala Phe Val Val Thr Leu Leu Leu Thr
                500               505               510
Asn His Thr Gln Ser Ala Asn Arg Trp Glu Glu Arg Leu Glu Glu Tyr
                515               520               525
Leu Leu Asp Leu Lys Val Pro Glu Gly Leu Arg Ile Ser Phe Asn Thr
                530               535               540
Glu Ile Ser Leu Glu Lys Glu Leu Asn Asn Asn Asn Asp Ile Ser Thr
545               550               555               560
Val Ala Ile Ser Tyr Leu Met Met Phe Leu Tyr Ala Thr Trp Ala Leu
                565               570               575
Arg Arg Lys Asp Gly Lys Thr Arg Leu Leu Leu Gly Ile Ser Gly Leu
                580               585               590
Leu Ile Val Leu Ala Ser Ile Val Cys Ala Ala Gly Phe Leu Thr Leu
                595               600               605
Phe Gly Leu Lys Ser Thr Leu Ile Ile Ala Glu Val Ile Pro Phe Leu
                610               615               620
Ile Leu Ala Ile Gly Ile Asp Asn Ile Phe Leu Ile Thr His Glu Tyr
625               630               635               640
Asp Arg Asn Cys Glu Gln Lys Pro Glu Tyr Ser Ile Asp Gln Lys Ile
                645               650               655
Ile Ser Ala Ile Gly Arg Met Ser Pro Ser Ile Leu Met Ser Leu Leu
                660               665               670
Cys Gln Thr Gly Cys Phe Leu Ile Ala Ala Phe Val Thr Met Pro Ala
                675               680               685
Val His Asn Phe Ala Ile Tyr Ser Thr Val Ser Val Ile Phe Asn Gly
                690               695               700
Val Leu Gln Leu Thr Ala Tyr Val Ser Ile Leu Ser Leu Tyr Glu Lys
705               710               715               720
Arg Ser Asn Tyr Lys Gln Ile Thr Gly Asn Glu Thr Lys Glu Ser
                725               730               735
Phe Leu Lys Thr Phe Tyr Phe Lys Met Leu Thr Gln Lys Arg Leu Ile
                740               745               750
Ile Ile Ile Phe Ser Ala Trp Phe Phe Thr Ser Leu Val Phe Leu Pro
                755               760               765
Glu Ile Gln Phe Gly Leu Asp Gln Thr Leu Ala Val Pro Gln Asp Ser
770               775               780
Tyr Leu Val Asp Tyr Phe Lys Asp Val Tyr Ser Phe Leu Asn Val Gly
785               790               795               800
Pro Pro Val Tyr Met Val Val Lys Asn Leu Asp Leu Thr Lys Arg Gln
                805               810               815
Asn Gln Gln Lys Ile Cys Gly Lys Phe Thr Thr Cys Glu Arg Asp Ser
                820               825               830
Leu Ala Asn Val Leu Glu Gln Glu Arg His Arg Ser Thr Ile Thr Glu
                835               840               845
```

```
Pro Leu Ala Asn Trp Leu Asp Asp Tyr Phe Met Phe Leu Asn Pro Gln
    850                 855                 860
Asn Asp Gln Cys Cys Arg Leu Lys Lys Gly Thr Asp Glu Val Cys Pro
865                 870                 875                 880
Pro Ser Phe Pro Ser Arg Arg Cys Glu Thr Cys Phe Gln Gln Gly Ser
                885                 890                 895
Trp Asn Tyr Asn Met Ser Gly Phe Pro Glu Gly Lys Asp Phe Met Glu
            900                 905                 910
Tyr Leu Ser Ile Trp Ile Asn Ala Pro Ser Asp Pro Cys Pro Leu Gly
        915                 920                 925
Gly Arg Ala Pro Tyr Ser Thr Ala Leu Val Tyr Asn Glu Thr Ser Val
    930                 935                 940
Ser Ala Ser Val Phe Arg Thr Ala His His Pro Leu Arg Ser Gln Lys
945                 950                 955                 960
Asp Phe Ile Gln Ala Tyr Ser Asp Gly Val Arg Ile Ser Ser Ser Phe
                965                 970                 975
Pro Glu Leu Asp Met Phe Ala Tyr Ser Pro Phe Tyr Ile Phe Phe Val
            980                 985                 990
Gln Tyr Gln Thr Leu Gly Pro Leu Thr Leu Lys Leu Ile Gly Ser Ala
        995                 1000                1005
Ile Ile Leu Ile Phe Phe Ile Ser Ser Val Phe Leu Gln Asn Ile Arg
    1010                1015                1020
Ser Ser Phe Leu Leu Ala Leu Val Val Thr Met Ile Ile Val Asp Ile
1025                1030                1035                1040
Gly Ala Leu Met Ala Leu Leu Gly Ile Ser Leu Asn Ala Val Ser Leu
                1045                1050                1055
Val Asn Leu Ile Ile Cys Val Gly Leu Gly Val Glu Phe Cys Val His
            1060                1065                1070
Ile Val Arg Ser Phe Thr Val Val Pro Ser Glu Thr Lys Lys Asp Ala
        1075                1080                1085
Asn Ser Arg Val Leu Tyr Ser Leu Asn Thr Ile Gly Glu Ser Val Ile
    1090                1095                1100
Lys Gly Ile Thr Leu Thr Lys Phe Ile Gly Val Cys Val Leu Ala Phe
1105                1110                1115                1120
Ala Gln Ser Lys Ile Phe Asp Val Phe Tyr Phe Arg Met Trp Phe Thr
                1125                1130                1135
Leu Ile Ile Val Ala Ala Leu His Ala Leu Leu Phe Leu Pro Ala Leu
            1140                1145                1150
Leu Ser Leu Phe Gly Gly Glu Ser Tyr Arg Asp Asp Ser Ile Glu Ala
        1155                1160                1165
Glu Asp
    1170

<210> SEQ ID NO 7
<211> LENGTH: 11459
<212> TYPE: DNA
<213> ORGANISM: Caenorhabditis elegans

<400> SEQUENCE: 7
tcagagaaaa gaaaacttat gacaaaatac cattaaattg cttttaaaat cccgtattta      60
gaaagttatc actacgttag cttaccacag ggaagttgag agtaatgaaa atatgataaa     120
gttttaatga gtggatgaga agtgtatgag aagtgacaaa aaacaacaag agtacctatt     180
gttgccgcat aaatgtacaa tacatggcat ttgataaatg acacggaaat aacaaagtga     240
```

```
atgtatggaa tagaataagt gaagagtaaa tcggtatcta caaagatcgg agatccggtt    300
ctatatgagc tcttggcatt cgggaggtac atggcagtga agatggcgta gatgggtaag    360
agcgatcgat tgttatgata tctaaaataa aaacgatttg aaaataatt atatagtgcc     420
ggccaatact ctttcgtcta cgggttttcg gaaattcgtt tgagttgttc aaacaagaaa    480
aacttaaaaa ctatgatagt caggtaaaca ttttccacta aaaattaatt tttaaaatt     540
ttttagaaga tgacactcgg cggatccgtt tttgactgaa atttctaaat gagccacaat    600
gtgtgtactc aaaatcagaa ccgtcggatg ccagatgctg taacttttc gaataagcgt     660
tatataactc tgacattaac aataatttag aaaaaactgg gaatactttg taagtagaaa    720
atagtttgct aactaccgaa actttatcaa acttgttgtt ttggccgcgt ttataagttt    780
atatatttct aactataagt atcatcaaat ctacttgaaa tccctaccaa ttgctttatc    840
aatcccacct tccgctttaa gaagcggatc gagaatgtgg ctggcgtcca gtaaagaagg    900
acggttaagg attccttctt ccacgtttga aatatgactt tccgcggttg gcgacctaaa    960
atttcacatg taactttctg tttaaatccc gatttacaac ttacaaaacg cacgcgtcat   1020
gttgctcgtc attgtcattc gtgctagtct ctgaacttcc atggcctctc gatcctccga   1080
aggcaagcaa aataggcaat atgatgagag catggacagc actgctgaca atagtgatga   1140
ggaacaattt gaaaaagtag acctgaaggg gttgatttaa attacgatta acaaattgtt   1200
taagttaccg ttataatctg aagatgagcc cccgagagaa acattgtaga tccagccata   1260
gtgacaactg ggccggagag aatgattggt ccaatacttc caaccgtaga ctctgcgcga   1320
tcttttgctc gctggcgaag tgagcaggcg tatcctttga gaacatttac agaaaactcg   1380
attagaattc cagacgactg aaaactcaaa ttaatgtttt tcaatcgttc cacatataat   1440
tgaacctacc attacaagat tgttgcaga caaggcattg acggggatat taaagatata   1500
cataaatgcc acaatatgga agtagttgga cacttgacaa attacagcgc aagccgctcc   1560
tttcacatca atcccaagag taacacaaat gatgccgaag acgccaacaa cagtgataaa   1620
aagttgggta gtgagaattg gcatgatagt agagtactgt tcgtagaatg gaaaattt     1680
gctgtatgcg aagacgtgag ctgtatcgtc aattgatctt tcaaggcgac gggataccat   1740
tcgagcagtg tccattgcct tgatgaaatc actggagttg ctaattgaca gcttttttgtg  1800
gaaagtcatg aattgagatg cttgaatacg tcctctagat gtgaagctga ttgcatcttt   1860
gaatgaagca cggccactga aatttaggtt aacttgaaaa aatagacatt aacaataaaa   1920
aatttaaatt cctacccgaa aacgcattca gaatttggag tgtcttctaa aaagtgtctc   1980
agatgacggt agaaaacttc gattgacgga cgatggtaca tgattgagct tttcgggtac   2040
gagttggcca cgtaatcaaa gtccatgcaa gttctacatg ccttatcgtc taacgcactc   2100
ttgttccggt ttgtcgagca gaatgtgttg gggtcgtgca cataaacttt acaacatggg   2160
cttttttcttg aaatccattc cagatagttg tcaatccagt tatacatttc accggacaag   2220
tacgtctgct ccgtgtgtcc aactgcgtaa ttcataatgt ttccaaacga agtgtcgcta   2280
cacccaggaa atgtacaaaa cttgttctga acatctggtc tgtgccaatc aagttctccg   2340
tcaacagtga aaaacactgg cggtcccacg tcaaaaaatt tgtcgagata tcgaaagtgc   2400
gtgctgatgt agcttttctg taatagtaag ttttttttca ggacaaggtg attaagttta   2460
cctctgtgaa agccatactc tggtcgaatc caacgctgat cttacttgag aggatcactg   2520
ttgtaatgaa agaagcaatg aagattattc cctgaaaata ttaaaaataa ttaataacta   2580
```

-continued

```
cgtatcgcac tacgcaatgc agatctgggc ttcagataca ctgctcagtg atgctcccac    2640
tagggtttac atcaagccac gtccaagccg tggactatgg ccggtaatcc attcgcggaa    2700
tatttcgttt cttaattgaa actgtgtgaa cctagtgggg aggcagggcg tgaacttgtg    2760
atttcgttat tgctagcggc aatcactacc tgctgagcta ttcccgctta gtttaattca    2820
acttactgtg ataatacgag tcattctgtg catcaggaac ggagctactt gaaagtggaa    2880
gaattgtgtc ataaaagtgt ctgtcgccct ctgacgacca ataaggtaag cacccaaaag    2940
atccttgatt tgatatggga aaagaactc tggttttcca ttgagctccc tttgagtgtc     3000
ccatacgaaa agtgcaagga aaattgtgca atgtaagacc acatcaataa gaacagcaag    3060
accggcgtag agacaaaatg ttcggattgc aggcaaatct gtgaatccac ctgtaaacca    3120
agattttaaa tttggtacga tattttaaca tttttatatt tcttaccaat gaaaaagctg    3180
aaagcacatc ccaacgagct actgaacata gctggcatag ttccagccat gaccattccc    3240
acgatctctg gacattggtc gggggacatg taaggcatgg agactctttg ttgagcgtag    3300
tacttaacaa ccatgaatgt acgacagacg cctagcaacg tcacaacgaa gaattgtacg    3360
accaacgcat ttttgaccgg atggattcca aacatggaga aaattcccca cgagcagaac    3420
gaactgagca agtttatgat gacgctcagc attccaagac agattcgaga atgtaccaga    3480
attgaccaaa gctgattctc acacacaaag taacgcccga gagagaatgt aacataaccg    3540
atgagaaaag ccagagcaat cacaacagtc acaatttcat cctttgcgtc gttttcaatc    3600
tcatcagtga tcgacctttc tgccataaac gagaaaatca ctttcggaga cttttctctg    3660
tactctttgc agaacttcaa aaactccttc tcccaaagtt ctgcttttg aatctccggc     3720
tcagttctct gtgtgaccag gatagtcatc atgatcgagt tggcagcttg atgattcgta    3780
ctattttgc cgaagaccat gttaggagca gatggtccac cgtatgttcc catgcagctc     3840
aggccggact ttgttttttg ggacattggt tgactgtaat agatatgaat aataattatt    3900
gttattctat ttttatgttc attttttcttt ttgaaaacat tgtttcacta actctataca   3960
tgctgccatg tgattcatcc attcatctgt tgttgcttcc gatgagaaat aatcaaacgc    4020
gtcatcatct tcggaaaccg tttcttcttt gttcgatttc atatccagat gctctttgtt    4080
cccctgtaaa atgaacaact ttgcactcaa caagactaca gtatagttaa acatacttga    4140
aaatagttcg ttggagacat aatcaaacaa tcatatcctg gtcccatagg tcgataacat    4200
acatcatcaa gtgtgattgt ccgaccatca gagtcttgcg ttgatatatt tttgatggca    4260
tttaaaatat cgaaaagctc ctcaaaaatg tccttgtgga atactggtcc ataaagcttc    4320
ccgctcgatt ggaaatcgcg gtgacttagc aacataattt gctgatatct ctgtgggcgt    4380
ctaaatttat attacagttt ttagtacgaa gttgaaggta gatgtcgtgg tgctaaaacg    4440
acaaaaatat catagttaaa cttttcaaaa ttgtttgaaa aattttaatt gaaaatcaaa    4500
aagtggtcat tttaacacca cagcagtggt ttataacaac ttcaaaactg gtgctactga    4560
aaagcttacc caaagttggc attgaaaacc atctcttctt gtcgagccct ggatctcgga    4620
gaagaccaca tatcaacaac atttgtcgac tctttgtgat aaatcattcc tggcaagcag    4680
aaaatcagaa cggcacatcc tatgaaaaag tgagactttg gattgcgtcc cgccatcatt    4740
ccaatatctc gagcattgtt ctccatgaag ttgtgaatcc aggcaccggt ccgtttgatt    4800
ctgttccgtt tcggggattc ttctccagat tgtgtttgcc tcaagttctg aaatatgcct    4860
ttttactttt ttttttcaag tattgatttt tcaatgtcca accgtgtagt cttcgtcata    4920
tgatgtgaat acaaatccaa cacaaagaag cacggcaagt gagccgatga aggcgagcat    4980
```

```
gacaaaaatg ttcaggcagg cgatgccatg aacattgcaa gtttgctgaa attgaaattt   5040 tttttttctca attttctagg tggcgagact caaaaacttt attaaaacat cacgatgttt   5100
ctcaattatt tcaaatccaa ataattcttg tgtttattct gtgttatttg ttgttgactt   5160
tctgtttcgc cgactctgtt ttttccccag caaccattct ctgaccatta tccgtcccac   5220
acaataccta cattgcccta cgcatcaacg tcatgttaac tccattttgc acaaaagaga   5280
gtccacaaat gagtaacaaa accaatttgc gaaacgatca aacattttct atgagctaag   5340
taacagaaaa ctgttttaaa tgaactatga ccaaaaacct ggaatgtgtg ttgccgtgaa   5400
gcaccgacaa acaagttatt gcaacagtaa agttactgtt caagcacctt ttctatttac   5460
actggtttat tgattattgg aaactacgat tattgagact atatttgagg ttatagtcat   5520
agccatcatt ttttaatctt gttttattat atttgcacaa gacatgggaa cggagtttgt   5580
gcttgttttt acaaactatg gaaatacgaa ctttgagaat aacttttcaa ttttttaaga   5640
tcttagatcc cttaccccag aagttttttcc atcgtccagg tcgatcaagt ttgcgtactc   5700
ttccttgttg cactctgacg ttgaacaagc cggccagccg actcgagctg atttgtcgca   5760
cccagtaaag ttgacattca tgtacgttga acgatccgat ggaggtgtct gaatgagtca   5820
gggtttttac gaaaaattga agtagtacta ataccttgat agggtcatag agaaggaact   5880
tgtgtggatt ggaatattga gatctagatt ttgagttcca ataaattcca accaatttgt   5940
caaagtacac ggagtagaag tacacatgac tcgtaatgca ggctgccctc caaaagttac   6000
atctttacaa gacgagaaca ttccctcagc aaaatcagta gacaatctgt actcgactgt   6060
attcacgtat gcctcagctg gttggtactc tggggtgaat ccctctttct tctcgattgg   6120
tttcatttcg gagatctgaa aaaaactat tcattttttt tccaaaaaat catatttgcg   6180
tatgtattca tgacgttatc agcgtgagtt gtctactgac tcacacatgc atagttagag   6240
gtcgcttatc agaaacgata taatatgcgt acttcaacgt ttctattgtc gccctattaa   6300
tcagtaatca gctcaaacgt tgcaaaaatg aaacagtcag aaaaaaatca ttaaaaaatg   6360
gataaattat taacagaaca cactgaccga tacaaaatcc tgttgattcg ggctgcacgt   6420
aaattcgcac cacaatttgg caaagttgtc gaagcacgac ggacatcgtc ccagaatatg   6480
tcgggcttgt gcaatttgct tagtcagtcc ttccgcttgc gatggcgtac agcagagttt   6540
gttgtcacct gaaaagtgtt ccattgatat cacacaactt tcgctttttt cgattagaga   6600
gggagcaatg agtcacaata atttcggaag cgttttgacg gatgtgtaag ctacgatgtt   6660
tttttttgta gtgcgcttgt ttccggatta tttgcgttgc tttagtggtt attttcggta   6720
cagaaaaagt gtaaaaattt aaaaactagt cggattatga aaattggaaa attttagttt   6780
gaaaatagcg aaataaaaat tttataaaat gttttaacca gtttttacaa caaaataagg   6840 ccgaattttca ttttcagaaa aaagttctca atacatattt aaattttgaa taactctact   6900
aaattttgct taaattttc attttttaact tgcttgtgtt gcaagagctg cttttttcac   6960
aaattcatta ttacctttttt tacattttcg ggatttttata tactttccag agataggtta   7020
ccaaatttgg aataaaccat ccattggcat ttaaaggtgg agtatggcca gttggaaatt   7080
tttgaaaagc ctttgtaaaa ttttaaaacg gctaaatatc ataaaaaaat cttttcaaac   7140
attttaaaaa taattttttat ttcgagtgaa aatgtggtaa aatctgagtt tgagagatct   7200
aaaattgttt ttttgatcga ccacttccaa aaaattgaca aaatctgaaa cttcatcgct   7260
ttttggtttg aaatgaaaaa ttttccaaaa tcttttcaaa atgtttatta tgatatttgg   7320
```

```
ttatttttag cgccatggaa attttcattt ttttaaaatc atttcccaac tgaacacaca    7380
cctattaaaa cagcaaagtc aaaaacttac cagttagcaa atgggggcaa aactcgacca    7440
ttttctcata tgccggatga gttttgtcaa aagctgtggg ctccacatta gtatcgttgg    7500
taacacatgg tccatatgca ttttcagtat gcttctggca caatcctcgc atgatacatc    7560
ccgcgtcgcc atgatggaat atagacccaa atagcaagca aaaatgagt agttgtttca     7620
tttcttgtgc atcgactgaa acatacgggg tatgtaagaa tgtaaaacag actgttggcg    7680
agggcggcgg cactttggct ccgcctcttc gaacacaagc acacggttca atgaaactac    7740
tgaattattg accgggaggt tagacgtagg gcgagagaga gagaaagaaa ataaatcgag    7800
aggtcgagaa aaagcatcag gatggtcaca cgttttctga ctcatcccca gtcagaaaac    7860
gtgcaaatgt ggtctgtaca aaagtaaact tctagaagga gaaacgctac tttatttcaa    7920
acgagaaaca cataaaaaaa ccagtgtttg tcatggagct ccattgaaaa tgtttgcgca    7980
tgaactcgag tcagagagag tctatctcaa atttttcac atctgtgatt ttagaaatgt     8040
gtcatatttt agtagtttaa aaatatatt cattaattga aaacaggaaa aaacctctag     8100
aagtacataa aagttggatg caaaacacaa aaaccaagct gtgggtcgag cctatttcga    8160
taatttttat tcttggctgt gctagtttag atttgaatac tgcgctgata ttccaaaaca    8220
ggcaccaaaa tttttaatga tcagaatttt ttaacttttt gaatagtgag cagttaaaca    8280
ctaatttaca ttggagatat aaccactgct gccaaaatga cgtggcaaaa aattgaattt    8340
taaaaacaaa acaccaaatg tgacttccat atgactgctg tattcatatt gtgaaacttt    8400
gattttagg agttgatttc tctcactcgt aaactatttt tttctgtgtg aagaagctgc     8460
tgatgtaagg cattttagc tggttgttgg ctaattttt tcagccttat cagtgcactg      8520
ataaaaatca aaatgaagt ggaatatcag gttgtccaaa ttagtctatt gtttctgttt     8580
ctgtttcaaa cacggaaaac gaaacgtgt gataatgaag caaactgaaa aaagaacaac     8640
gatcgtaaaa cgttttggtc atttttttta aaagaattta tgaatcatga tatattcaat    8700
ttttacactt tttagcacct cgttattctt ttttttgttt tgagtcacaa taaaaaatcg    8760
tttggaaaat agaaataatg aaaaacggca ggaaatgaa acaaaagtg aagcttgagg      8820
gtccttatga gcaaaatatg taagcgtctc caatttccct gacgacggag ccacgtgaaa    8880
ctattggaaa tttagcttct agaaatttca aaatgggtta gtgagtgact ggacttgtta    8940
aattggtagg gctagtaggg ggcgagtaaa gggcgactgg gggcgacatc ggacaacatc    9000
tgggggagag gtaggaataa tgaacacccg ctacttgtcc ggtgttgtcc catattgccc    9060
gcagtcgcct actacatgta cgctctttc cagttgtccc ttactctttg ttgtttcagg     9120
ccagtatctg actttactct cagaaatatt gttttaacc tgtacaagaa accaaaaaga    9180
ccgactagca aaattacaat caagaacgt cttcaaaatt gataagattg caagaattct     9240
catctatttt tcattttgac cgtgagaatg aatgtgtttt gaattacaac tacgcaaaat    9300
tcttgaaaaa aagaaaattg gcaggaacag atttaaatat tggaaaatat ggcacaaaaa    9360
gacaaaaaaa aacgaggtga gagggaaatg gcatgacaac gggacttggc agcgatgctt    9420
tccggaaaga acaaagctag aaatgtcatc acttcacaac gagtacaaag tccaaaagtg    9480
taggtgtact ggaattgctg aagaggtgaa atgtataggt gtacaataag aatattgggt    9540
tgcaccctat gctcattttt ccaattttc aagtgacaca caaatggaaa tgtatattaa     9600
ccggatatgg aacggactgt caagccggat attagacttc ctatagactt ccgaaaaagg    9660
ccaaacaaat tgttggaaac tgaatggtca gaataattag aatgaataat gaatattggt    9720
```

-continued

```
tagttgcatc caacccacgg acttttagaa aattagtcaa aaagtcacaa aacaataaat    9780
tagaacaggt gatcgtgtga aacacgatga gaaaattgaa gatggaatga agttttgtga    9840
gcacaaggaa caataaactc taactgcata ctttcatgag tgaaaaggtc taaaatattt    9900
attaaaaacc gtatttcttc aggagagtgg gaaaaaattg ttttatcagt ttccctctaa    9960
ttaaacaaaa aacttctaat ttaaacataa atcaagtgca ttctgatttc taaaaactga    10020
atatcaaaag atatattccc cctgctaaaa aaaacaaaa caaatgaaa aaagcaatat    10080 cgtcaagttg aaataaaaca gaatgtctca aaaaagaaa acgaaaaatt gagccaaatg    10140
acgtgtttac tatatttcaa tttacacgtc agactacagt atctagagta ttcaattaac    10200
tgtctatgtt ttttttctag aatttccgac tgtattattt tgattttctt tgtgaatgaa    10260
cttagacgta gtaaactaga aaaaaatagt aaactagagc acgctatgag ggacacagtc    10320
catttcgtac aatatatgtt atgttaaaca tatatgttaa aaaatatgta tataaattgt    10380
gcaccatgaa aaataactag gaaagtaata gaacatcgcc gtgctcatta aatttgagct    10440
ctaaagaatg aaatagggct tcttgcaaag gcttcaaaga tttttaattt taaaagctat    10500
ctttgagcaa taacaaaata taccaattac aaataaaaaa caaaacaact tctcaaaaac    10560
cggcgtgttt ttaggatgct cactatctta atgcactact agttgtttta tacaacgcgc    10620
tcaaaactcg ctgcagaaaa aaagtgctcg gatttgtggt gcgtgaaacc ataaaaatac    10680
acttgcaggt cgttttcatg agaagactgc gagacgagag aatagggca attgaacggc    10740 gtcatacgaa aatcaggtca aaatttggtt gactctcaca aaagaaattc tttactgcat    10800
tgttccaatg ttttcatga tacacttttg tcgagaccta cggttttgca aaactttgat    10860
ttttattcag agaattttt ctagagtttg aaaaatgttt aaaaaaaggt acctagaaaa    10920
ataaaatata attattcata taaatcgaaa taataatagt agtttagaat ttgttgacaa    10980
aaagccattt ttaaagtttc tcaaaacttt tttaaattat atgttttgga aaaggttaat    11040
atcacgtttt tcaagtgtaa ctaacaaagg aagtgtttta gattttttt ctggaatatt    11100 ccaaaaaaac ctatcatttg aaaaataacc gttgcaatag gtgacggcaa aagtagctgt    11160
ggaagagaat ttcgtactag gagcaaacct atccaagatc atttcattgc atttttcatt    11220
tctttcgagg tttgtataaa attattccaa agatgttttt tgcgaataaa aaaatgtttt    11280
caagagtata tagggtgtaga attagtttcg atgcttttg gtaagttatg tattcattta    11340
ttaaattttg taaagatcag aagattttc acccaactca atacaacatt ttccagattt    11400
tgctttctga ataaactaat tttctaaaaa agcttccaga atgtctaaaa acattaaaa    11459
```

<210> SEQ ID NO 8
<211> LENGTH: 4371
<212> TYPE: DNA
<213> ORGANISM: Caenorhabditis elegans
<220> FEATURE:
<221> NAME/KEY: CDS
<222> LOCATION: (1)..(3891)

<400> SEQUENCE: 8

```
atg aaa caa cta ctc att ttt tgc ttg cta ttt ggg tct ata ttc cat      48
Met Lys Gln Leu Leu Ile Phe Cys Leu Leu Phe Gly Ser Ile Phe His
  1               5                  10                  15 cat ggc gac gcg gga tgt atc atg cga gga ttg tgc cag aag cat act      96
His Gly Asp Ala Gly Cys Ile Met Arg Gly Leu Cys Gln Lys His Thr
             20                  25                  30 gaa aat gca tat gga cca tgt gtt acc aac gat act aat gtg gag ccc     144
```

```
Glu Asn Ala Tyr Gly Pro Cys Val Thr Asn Asp Thr Asn Val Glu Pro
         35                  40                  45 aca gct ttt gac aaa act cat ccg gca tat gag aaa atg gtc gag ttt      192
Thr Ala Phe Asp Lys Thr His Pro Ala Tyr Glu Lys Met Val Glu Phe
 50                  55                  60 tgc ccc cat ttg cta act ggt gac aac aaa ctc tgc tgt acg cca tcg      240
Cys Pro His Leu Leu Thr Gly Asp Asn Lys Leu Cys Cys Thr Pro Ser
 65                  70                  75                  80 caa gcg gaa gga ctg act aag caa att gca caa gcc cga cat att ctg      288
Gln Ala Glu Gly Leu Thr Lys Gln Ile Ala Gln Ala Arg His Ile Leu
                 85                  90                  95 gga cga tgt ccg tcg tgc ttc gac aac ttt gcc aaa ttg tgg tgc gaa      336
Gly Arg Cys Pro Ser Cys Phe Asp Asn Phe Ala Lys Leu Trp Cys Glu
                100                 105                 110 ttt acg tgc agc ccg aat caa cag gat ttt gta tcg atc tcc gaa atg      384
Phe Thr Cys Ser Pro Asn Gln Gln Asp Phe Val Ser Ile Ser Glu Met
            115                 120                 125 aaa cca atc gag aag aaa gag gga ttc acc cca gag tac caa cca gct      432
Lys Pro Ile Glu Lys Lys Glu Gly Phe Thr Pro Glu Tyr Gln Pro Ala
130                 135                 140 gag gca tac gtg aat aca gtc gag tac aga ttg tct act gat ttt gct      480
Glu Ala Tyr Val Asn Thr Val Glu Tyr Arg Leu Ser Thr Asp Phe Ala
145                 150                 155                 160 gag gga atg ttc tcg tct tgt aaa gat gta act ttt gga ggg cag cct      528
Glu Gly Met Phe Ser Ser Cys Lys Asp Val Thr Phe Gly Gly Gln Pro
                165                 170                 175 gca tta cga gtc atg tgt act tct act ccg tgt act ttg aca aat tgg      576
Ala Leu Arg Val Met Cys Thr Ser Thr Pro Cys Thr Leu Thr Asn Trp
                180                 185                 190 ttg gaa ttt att gga act caa aat cta gat ctc aat att cca atc cac      624
Leu Glu Phe Ile Gly Thr Gln Asn Leu Asp Leu Asn Ile Pro Ile His
            195                 200                 205 aca aag ttc ctt ctc tat gac cct atc aag aca cct cca tcg gat cgt      672
Thr Lys Phe Leu Leu Tyr Asp Pro Ile Lys Thr Pro Pro Ser Asp Arg
210                 215                 220 tca acg tac atg aat gtc aac ttt act ggg tgc gac aaa tca gct cga      720
Ser Thr Tyr Met Asn Val Asn Phe Thr Gly Cys Asp Lys Ser Ala Arg
225                 230                 235                 240 gtc ggc tgg ccg gct tgt tca acg tca gag tgc aac aag gaa gag tac      768
Val Gly Trp Pro Ala Cys Ser Thr Ser Glu Cys Asn Lys Glu Glu Tyr
                245                 250                 255 gca aac ttg atc gac ctg gac gat gga aaa act tct ggg caa act tgc      816
Ala Asn Leu Ile Asp Leu Asp Asp Gly Lys Thr Ser Gly Gln Thr Cys
                260                 265                 270 aat gtt cat ggc atc gcc tgc ctg aac att ttt gtc atg ctc gcc ttc      864
Asn Val His Gly Ile Ala Cys Leu Asn Ile Phe Val Met Leu Ala Phe
            275                 280                 285 atc ggc tca ctt gcc gtg ctt ctt tgt gtt gga ttt gta ttc aca tca      912
Ile Gly Ser Leu Ala Val Leu Leu Cys Val Gly Phe Val Phe Thr Ser
290                 295                 300 tat gac gaa gac tac acg aac ttg agg caa aca caa tct gga gaa gaa      960
Tyr Asp Glu Asp Tyr Thr Asn Leu Arg Gln Thr Gln Ser Gly Glu Glu
305                 310                 315                 320 tcc ccg aaa cgg aac aga atc aaa cgg acc ggt gcc tgg att cac aac     1008
Ser Pro Lys Arg Asn Arg Ile Lys Arg Thr Gly Ala Trp Ile His Asn
                325                 330                 335 ttc atg gag aac aat gct cga gat att gga atg atg gcg gga cgc aat     1056
Phe Met Glu Asn Asn Ala Arg Asp Ile Gly Met Met Ala Gly Arg Asn
            340                 345                 350
```

```
cca aag tct cac ttt ttc ata gga tgt gcc gtt ctg att ttc tgc ttg    1104
Pro Lys Ser His Phe Phe Ile Gly Cys Ala Val Leu Ile Phe Cys Leu
        355                 360                 365 cca gga atg att tat cac aaa gag tcg aca aat gtt gtt gat atg tgg    1152
Pro Gly Met Ile Tyr His Lys Glu Ser Thr Asn Val Val Asp Met Trp
370                 375                 380 tct tct ccg aga tcc agg gct cga caa gaa gag atg gtt ttc aat gcc    1200
Ser Ser Pro Arg Ser Arg Ala Arg Gln Glu Glu Met Val Phe Asn Ala
385                 390                 395                 400 aac ttt gga cgc cca cag aga tat cag caa att atg ttg cta agt cac    1248
Asn Phe Gly Arg Pro Gln Arg Tyr Gln Gln Ile Met Leu Leu Ser His
            405                 410                 415 cgc gat ttc caa tcg agc ggg aag ctt tat gga cca gta ttc cac aag    1296
Arg Asp Phe Gln Ser Ser Gly Lys Leu Tyr Gly Pro Val Phe His Lys
        420                 425                 430 gac att ttt gag gag ctt ttc gat att tta aat gcc atc aaa aat ata    1344
Asp Ile Phe Glu Glu Leu Phe Asp Ile Leu Asn Ala Ile Lys Asn Ile
    435                 440                 445 tca acg caa gac tct gat ggt cgg aca atc aca ctt gat gat gta tgt    1392
Ser Thr Gln Asp Ser Asp Gly Arg Thr Ile Thr Leu Asp Asp Val Cys
450                 455                 460 tat cga cct atg gga cca gga tat gat tgt ttg att atg tct cca acg    1440
Tyr Arg Pro Met Gly Pro Gly Tyr Asp Cys Leu Ile Met Ser Pro Thr
465                 470                 475                 480 aac tat ttt caa ggg aac aaa gag cat ctg gat atg aaa tcg aac aaa    1488
Asn Tyr Phe Gln Gly Asn Lys Glu His Leu Asp Met Lys Ser Asn Lys
            485                 490                 495 gaa gaa acg gtt tcc gaa gat gat gac gcg ttt gat tat ttc tca tcg    1536
Glu Glu Thr Val Ser Glu Asp Asp Asp Ala Phe Asp Tyr Phe Ser Ser
        500                 505                 510 gaa gca aca aca gat gaa tgg atg aat cac atg gca gca tgt ata gat    1584
Glu Ala Thr Thr Asp Glu Trp Met Asn His Met Ala Ala Cys Ile Asp
    515                 520                 525 caa cca atg tcc caa aaa aca aag tcc ggc ctg agc tgc atg gga aca    1632
Gln Pro Met Ser Gln Lys Thr Lys Ser Gly Leu Ser Cys Met Gly Thr
530                 535                 540 tac ggt gga cca tct gct cct aac atg gtc ttc ggc aaa aat agt acg    1680
Tyr Gly Gly Pro Ser Ala Pro Asn Met Val Phe Gly Lys Asn Ser Thr
545                 550                 555                 560 aat cat caa gct gcc aac tcg atc atg atg act atc ctg gtc aca cag    1728
Asn His Gln Ala Ala Asn Ser Ile Met Met Thr Ile Leu Val Thr Gln
            565                 570                 575 aga act gag ccg gag att caa aaa gca gaa ctt tgg gag aag gag ttt    1776
Arg Thr Glu Pro Glu Ile Gln Lys Ala Glu Leu Trp Glu Lys Glu Phe
        580                 585                 590 ttg aag ttc tgc aaa gag tac aga gaa aag tct ccg aaa gtg att ttc    1824
Leu Lys Phe Cys Lys Glu Tyr Arg Glu Lys Ser Pro Lys Val Ile Phe
    595                 600                 605 tcg ttt atg gca gaa agg tcg atc act gat gag att gaa aac gac gca    1872
Ser Phe Met Ala Glu Arg Ser Ile Thr Asp Glu Ile Glu Asn Asp Ala
610                 615                 620 aag gat gaa att gtg act gtt gtg att gct ctg gct ttt ctc atc ggt    1920
Lys Asp Glu Ile Val Thr Val Val Ile Ala Leu Ala Phe Leu Ile Gly
625                 630                 635                 640 tat gtt aca ttc tct ctc ggg cgt tac ttt gtg tgt gag aat cag ctt    1968
Tyr Val Thr Phe Ser Leu Gly Arg Tyr Phe Val Cys Glu Asn Gln Leu
            645                 650                 655 tgg tca att ctg gta cat tct cgt gga ttc aca gat ttg cct gca atc    2016
Trp Ser Ile Leu Val His Ser Arg Gly Phe Thr Asp Leu Pro Ala Ile
        660                 665                 670
```

```
cga aca ttt tgt ctc tac gcc ggt ctt gct gtt ctt att gat gtg gtc    2064
Arg Thr Phe Cys Leu Tyr Ala Gly Leu Ala Val Leu Ile Asp Val Val
        675                 680                 685 tta cat tgc aca att ttc ctt gca ctt ttc gta tgg gac act caa agg    2112
Leu His Cys Thr Ile Phe Leu Ala Leu Phe Val Trp Asp Thr Gln Arg
        690                 695                 700 gag ctc aat gga aaa cca gag ttc ttt ttc cca tat caa atc aag gat    2160
Glu Leu Asn Gly Lys Pro Glu Phe Phe Phe Pro Tyr Gln Ile Lys Asp
705                 710                 715                 720 ctt ttg ggt gct tac ctt att ggt cgt cag agg gcg aca gac act ttt    2208
Leu Leu Gly Ala Tyr Leu Ile Gly Arg Gln Arg Ala Thr Asp Thr Phe
                725                 730                 735 atg aca caa ttc ttc cac ttt caa gta gct ccg ttc ctg atg cac aga    2256
Met Thr Gln Phe Phe His Phe Gln Val Ala Pro Phe Leu Met His Arg
        740                 745                 750 atg act cgt att atc aca gga ata atc ttc att gct tct ttc att aca    2304
Met Thr Arg Ile Ile Thr Gly Ile Ile Phe Ile Ala Ser Phe Ile Thr
        755                 760                 765 aca gtg atc ctc tca agt aag atc agc gtt gga ttc gac cag agt atg    2352
Thr Val Ile Leu Ser Ser Lys Ile Ser Val Gly Phe Asp Gln Ser Met
    770                 775                 780 gct ttc aca gag aaa agc tac atc agc acg cac ttt cga tat ctc gac    2400
Ala Phe Thr Glu Lys Ser Tyr Ile Ser Thr His Phe Arg Tyr Leu Asp
785                 790                 795                 800 aaa ttt ttt gac gtg gga ccg cca gtg ttt ttc act gtt gac gga gaa    2448
Lys Phe Phe Asp Val Gly Pro Pro Val Phe Phe Thr Val Asp Gly Glu
                805                 810                 815 ctt gat tgg cac aga cca gat gtt cag aac aag ttt tgt aca ttt cct    2496
Leu Asp Trp His Arg Pro Asp Val Gln Asn Lys Phe Cys Thr Phe Pro
        820                 825                 830 ggg tgt agc gac act tcg ttt gga aac att atg aat tac gca gtt gga    2544
Gly Cys Ser Asp Thr Ser Phe Gly Asn Ile Met Asn Tyr Ala Val Gly
        835                 840                 845 cac acg gag cag acg tac ttg tcc ggt gaa atg tat aac tgg att gac    2592
His Thr Glu Gln Thr Tyr Leu Ser Gly Glu Met Tyr Asn Trp Ile Asp
    850                 855                 860 aac tat ctg gaa tgg att tca aga aaa agc cca tgt tgt aaa gtt tat    2640
Asn Tyr Leu Glu Trp Ile Ser Arg Lys Ser Pro Cys Cys Lys Val Tyr
865                 870                 875                 880 gtg cac gac ccc aac aca ttc tgc tcg aca aac cgg aac aag agt gcg    2688
Val His Asp Pro Asn Thr Phe Cys Ser Thr Asn Arg Asn Lys Ser Ala
                885                 890                 895 tta gac gat aag gca tgt aga act tgc atg gac ttt gat ggc cgt gct    2736
Leu Asp Asp Lys Ala Cys Arg Thr Cys Met Asp Phe Asp Gly Arg Ala
        900                 905                 910 tca ttc aaa gat gca atc agc ttc aca tct aga gga cgt att caa gca    2784
Ser Phe Lys Asp Ala Ile Ser Phe Thr Ser Arg Gly Arg Ile Gln Ala
        915                 920                 925 tct caa ttc atg act ttc cac aaa aag ctg tca att agc aac tcc agt    2832
Ser Gln Phe Met Thr Phe His Lys Lys Leu Ser Ile Ser Asn Ser Ser
    930                 935                 940 gat ttc atc aag gca atg gac act gct cga atg gta tcc cgt cgc ctt    2880
Asp Phe Ile Lys Ala Met Asp Thr Ala Arg Met Val Ser Arg Arg Leu
945                 950                 955                 960 gaa aga tca att gac gat aca gct cac gtc ttc gca tac agc aaa att    2928
Glu Arg Ser Ile Asp Asp Thr Ala His Val Phe Ala Tyr Ser Lys Ile
                965                 970                 975 ttc cca ttc tac gaa cag tac tct act atc atg cca att ctc act acc    2976
Phe Pro Phe Tyr Glu Gln Tyr Ser Thr Ile Met Pro Ile Leu Thr Thr
```

```
                    980                 985                 990
caa ctt ttt atc act gtt gtt ggc gtc ttc ggc atc att tgt gtt act      3024
Gln Leu Phe Ile Thr Val Val Gly Val Phe Gly Ile Ile Cys Val Thr
        995                 1000                1005 ctt ggg att gat gtg aaa gga gcg gct tgc gct gta att tgt caa gtg      3072
Leu Gly Ile Asp Val Lys Gly Ala Ala Cys Ala Val Ile Cys Gln Val
    1010                1015                1020 tcc aac tac ttc cat att gtg tcg tct gga att cta atc gag ttt tct      3120
Ser Asn Tyr Phe His Ile Val Ser Ser Gly Ile Leu Ile Glu Phe Ser
1025                1030                1035                1040 gta aat gtt ctc aaa gga tac gcc tgc tca ctt cgc cag cga gca aaa      3168
Val Asn Val Leu Lys Gly Tyr Ala Cys Ser Leu Arg Gln Arg Ala Lys
                1045                1050                1055 gat cgc gca gag tct acg gtt gga agt att gga cca atc att ctc tcc      3216
Asp Arg Ala Glu Ser Thr Val Gly Ser Ile Gly Pro Ile Ile Leu Ser
            1060                1065                1070 ggc cca gtt gtc act atg gct gga tct aca atg ttt ctc tcg ggg gct      3264
Gly Pro Val Val Thr Met Ala Gly Ser Thr Met Phe Leu Ser Gly Ala
        1075                1080                1085 cat ctt cag att ata acg gtc tac ttt ttc aaa ttg ttc ctc atc act      3312
His Leu Gln Ile Ile Thr Val Tyr Phe Phe Lys Leu Phe Leu Ile Thr
    1090                1095                1100 att gtc agc agt gct gtc cat gct ctc atc ata ttg cct att ttg ctt      3360
Ile Val Ser Ser Ala Val His Ala Leu Ile Ile Leu Pro Ile Leu Leu
1105                1110                1115                1120 gcc ttc gga gga tcg aga ggc cat gga agt tca gag act agc acg aat      3408
Ala Phe Gly Gly Ser Arg Gly His Gly Ser Ser Glu Thr Ser Thr Asn
                1125                1130                1135 gac aat gac gag caa cat gac gcg tgc gtt ttg tcg cca acc gcg gaa      3456
Asp Asn Asp Glu Gln His Asp Ala Cys Val Leu Ser Pro Thr Ala Glu
            1140                1145                1150 agt cat att tca aac gtg gaa gaa gga atc ctt aac cgt cct tct tta      3504
Ser His Ile Ser Asn Val Glu Glu Gly Ile Leu Asn Arg Pro Ser Leu
        1155                1160                1165 ctg gac gcc agc cac att ctc gat ccg ctt ctt aaa gcg gaa ggt ggg      3552
Leu Asp Ala Ser His Ile Leu Asp Pro Leu Leu Lys Ala Glu Gly Gly
    1170                1175                1180 att gat aaa gca att ggt agg gat ttc aaa tat cat aac aat cga tcg      3600
Ile Asp Lys Ala Ile Gly Arg Asp Phe Lys Tyr His Asn Asn Arg Ser
1185                1190                1195                1200 ctc tta ccc atc tac gcc atc ttc act gcc atg tac ctc ccg aat gcc      3648
Leu Leu Pro Ile Tyr Ala Ile Phe Thr Ala Met Tyr Leu Pro Asn Ala
                1205                1210                1215 aag agc tca tat aga acc gga tct ccg atc ttt gta gat acc gat tta      3696
Lys Ser Ser Tyr Arg Thr Gly Ser Pro Ile Phe Val Asp Thr Asp Leu
            1220                1225                1230 ctc ttc act tat tct att cca tac att cac ttt gtt att tcc gtg tca      3744
Leu Phe Thr Tyr Ser Ile Pro Tyr Ile His Phe Val Ile Ser Val Ser
        1235                1240                1245 ttt atc aaa tgc cat gta ttg tac att tat gcg gca aca ata ggt act      3792
Phe Ile Lys Cys His Val Leu Tyr Ile Tyr Ala Ala Thr Ile Gly Thr
    1250                1255                1260 ctt gtt gtt ttt tgt cac ttc tca tac act tct cat cca ctc att aaa      3840
Leu Val Val Phe Cys His Phe Ser Tyr Thr Ser His Pro Leu Ile Lys
1265                1270                1275                1280 act tta tca tat ttt cat tac tct caa ctt ccc tgt ggt aag cta acg      3888
Thr Leu Ser Tyr Phe His Tyr Ser Gln Leu Pro Cys Gly Lys Leu Thr
                1285                1290                1295 tag gcatttatgt atatctttaa tatccccgtc aatgccttgt ctgcaacaaa           3941
```

-continued

```
tcttgtaatg ttacgtggcc aactcgtacc cgaaaagctc aatcatgtac catcgtccgt      4001
caatcgaagt tttctaccgt catctgagac acttttttaga agacactcca aattctgaat     4061
gcgttttcgg gaatctgtct tggaatgctg agcgtcatca taaacttgct cagttcgttc      4121
tgctcgtggg gaattttctc catgtttgga atccatccgg tcaaaaatgc gttggtcgta      4181
caattcttcg ttgtgacgtt gctaggcgtc tgtcgtacat tcatggttgt taagtactac      4241
gctcaacaaa gagtctccat gccttacatg tcccccgacc aatgtccaga gatcgtggga      4301
atggtcatgg ctggaactat gccagctatg ttcagtagct cgttgggatg tgctttcagc      4361
tttttcattg                                                             4371
```

<210> SEQ ID NO 9
<211> LENGTH: 1296
<212> TYPE: PRT
<213> ORGANISM: Caenorhabditis elegans

<400> SEQUENCE: 9

```
Met Lys Gln Leu Leu Ile Phe Cys Leu Leu Phe Gly Ser Ile Phe His
 1               5                   10                  15

His Gly Asp Ala Gly Cys Ile Met Arg Gly Leu Cys Gln Lys His Thr
             20                  25                  30

Glu Asn Ala Tyr Gly Pro Cys Val Thr Asn Asp Thr Asn Val Glu Pro
         35                  40                  45

Thr Ala Phe Asp Lys Thr His Pro Ala Tyr Glu Lys Met Val Glu Phe
     50                  55                  60

Cys Pro His Leu Leu Thr Gly Asp Asn Lys Leu Cys Cys Thr Pro Ser
 65                  70                  75                  80

Gln Ala Glu Gly Leu Thr Lys Gln Ile Ala Gln Ala Arg His Ile Leu
                 85                  90                  95

Gly Arg Cys Pro Ser Cys Phe Asp Asn Phe Ala Lys Leu Trp Cys Glu
            100                 105                 110

Phe Thr Cys Ser Pro Asn Gln Gln Asp Phe Val Ser Ile Ser Glu Met
        115                 120                 125

Lys Pro Ile Glu Lys Lys Glu Gly Phe Thr Pro Glu Tyr Gln Pro Ala
    130                 135                 140

Glu Ala Tyr Val Asn Thr Val Glu Tyr Arg Leu Ser Thr Asp Phe Ala
145                 150                 155                 160

Glu Gly Met Phe Ser Ser Cys Lys Asp Val Thr Phe Gly Gly Gln Pro
                165                 170                 175

Ala Leu Arg Val Met Cys Thr Ser Thr Pro Cys Thr Leu Thr Asn Trp
            180                 185                 190

Leu Glu Phe Ile Gly Thr Gln Asn Leu Asp Leu Asn Ile Pro Ile His
        195                 200                 205

Thr Lys Phe Leu Leu Tyr Asp Pro Ile Lys Thr Pro Pro Ser Asp Arg
    210                 215                 220

Ser Thr Tyr Met Asn Val Asn Phe Thr Gly Cys Asp Lys Ser Ala Arg
225                 230                 235                 240

Val Gly Trp Pro Ala Cys Ser Thr Ser Glu Cys Asn Lys Glu Glu Tyr
                245                 250                 255

Ala Asn Leu Ile Asp Leu Asp Asp Gly Lys Thr Ser Gly Gln Thr Cys
            260                 265                 270

Asn Val His Gly Ile Ala Cys Leu Asn Ile Phe Val Met Leu Ala Phe
        275                 280                 285
```

-continued

```
Ile Gly Ser Leu Ala Val Leu Cys Val Gly Phe Val Thr Ser
    290                 295                 300
Tyr Asp Glu Asp Tyr Thr Asn Leu Arg Gln Thr Gln Ser Gly Glu Glu
305                 310                 315                 320
Ser Pro Lys Arg Asn Arg Ile Lys Arg Thr Gly Ala Trp Ile His Asn
                325                 330                 335
Phe Met Glu Asn Asn Ala Arg Asp Ile Gly Met Met Ala Gly Arg Asn
            340                 345                 350
Pro Lys Ser His Phe Phe Ile Gly Cys Ala Val Leu Ile Phe Cys Leu
        355                 360                 365
Pro Gly Met Ile Tyr His Lys Glu Ser Thr Asn Val Val Asp Met Trp
    370                 375                 380
Ser Ser Pro Arg Ser Arg Ala Arg Gln Glu Glu Met Val Phe Asn Ala
385                 390                 395                 400
Asn Phe Gly Arg Pro Gln Arg Tyr Gln Gln Ile Met Leu Leu Ser His
                405                 410                 415
Arg Asp Phe Gln Ser Ser Gly Lys Leu Tyr Gly Pro Val Phe His Lys
            420                 425                 430
Asp Ile Phe Glu Glu Leu Phe Asp Ile Leu Asn Ala Ile Lys Asn Ile
        435                 440                 445
Ser Thr Gln Asp Ser Asp Gly Arg Thr Ile Thr Leu Asp Asp Val Cys
    450                 455                 460
Tyr Arg Pro Met Gly Pro Gly Tyr Asp Cys Leu Ile Met Ser Pro Thr
465                 470                 475                 480
Asn Tyr Phe Gln Gly Asn Lys Glu His Leu Asp Met Lys Ser Asn Lys
                485                 490                 495
Glu Glu Thr Val Ser Glu Asp Asp Ala Phe Asp Tyr Phe Ser Ser
            500                 505                 510
Glu Ala Thr Thr Asp Glu Trp Met Asn His Met Ala Ala Cys Ile Asp
        515                 520                 525
Gln Pro Met Ser Gln Lys Thr Lys Ser Gly Leu Ser Cys Met Gly Thr
    530                 535                 540
Tyr Gly Gly Pro Ser Ala Pro Asn Met Val Phe Gly Lys Asn Ser Thr
545                 550                 555                 560
Asn His Gln Ala Ala Asn Ser Ile Met Met Thr Ile Leu Val Thr Gln
                565                 570                 575
Arg Thr Glu Pro Glu Ile Gln Lys Ala Glu Leu Trp Glu Lys Glu Phe
            580                 585                 590
Leu Lys Phe Cys Lys Glu Tyr Arg Glu Lys Ser Pro Lys Val Ile Phe
        595                 600                 605
Ser Phe Met Ala Glu Arg Ser Ile Thr Asp Glu Ile Glu Asn Asp Ala
    610                 615                 620
Lys Asp Glu Ile Val Thr Val Val Ile Ala Leu Ala Phe Leu Ile Gly
625                 630                 635                 640
Tyr Val Thr Phe Ser Leu Gly Arg Tyr Phe Val Cys Glu Asn Gln Leu
                645                 650                 655
Trp Ser Ile Leu Val His Ser Arg Gly Phe Thr Asp Leu Pro Ala Ile
            660                 665                 670
Arg Thr Phe Cys Leu Tyr Ala Gly Leu Ala Val Leu Ile Asp Val Val
        675                 680                 685
Leu His Cys Thr Ile Phe Leu Ala Leu Phe Val Trp Asp Thr Gln Arg
    690                 695                 700
Glu Leu Asn Gly Lys Pro Glu Phe Phe Pro Tyr Gln Ile Lys Asp
```

-continued

```
     705                 710                 715                 720
Leu Leu Gly Ala Tyr Leu Ile Gly Arg Gln Arg Ala Thr Asp Thr Phe
                725                 730                 735

Met Thr Gln Phe Phe His Phe Gln Val Ala Pro Phe Leu Met His Arg
                740                 745                 750

Met Thr Arg Ile Ile Thr Gly Ile Ile Phe Ile Ala Ser Phe Ile Thr
                755                 760                 765

Thr Val Ile Leu Ser Ser Lys Ile Ser Val Gly Phe Asp Gln Ser Met
    770                 775                 780

Ala Phe Thr Glu Lys Ser Tyr Ile Ser Thr His Phe Arg Tyr Leu Asp
785                 790                 795                 800

Lys Phe Asp Val Gly Pro Pro Val Phe Phe Thr Val Asp Gly Glu
                805                 810                 815

Leu Asp Trp His Arg Pro Asp Val Gln Asn Lys Phe Cys Thr Phe Pro
                820                 825                 830

Gly Cys Ser Asp Thr Ser Phe Gly Asn Ile Met Asn Tyr Ala Val Gly
                835                 840                 845

His Thr Glu Gln Thr Tyr Leu Ser Gly Glu Met Tyr Asn Trp Ile Asp
    850                 855                 860

Asn Tyr Leu Glu Trp Ile Ser Arg Lys Ser Pro Cys Cys Lys Val Tyr
865                 870                 875                 880

Val His Asp Pro Asn Thr Phe Cys Ser Thr Asn Arg Asn Lys Ser Ala
                885                 890                 895

Leu Asp Asp Lys Ala Cys Arg Thr Cys Met Asp Phe Asp Gly Arg Ala
                900                 905                 910

Ser Phe Lys Asp Ala Ile Ser Phe Thr Ser Arg Gly Arg Ile Gln Ala
                915                 920                 925

Ser Gln Phe Met Thr Phe His Lys Lys Leu Ser Ile Ser Asn Ser Ser
    930                 935                 940

Asp Phe Ile Lys Ala Met Asp Thr Ala Arg Met Val Ser Arg Arg Leu
945                 950                 955                 960

Glu Arg Ser Ile Asp Asp Thr Ala His Val Phe Ala Tyr Ser Lys Ile
                965                 970                 975

Phe Pro Phe Tyr Glu Gln Tyr Ser Thr Ile Met Pro Ile Leu Thr Thr
                980                 985                 990

Gln Leu Phe Ile Thr Val Val Gly Val Phe Gly Ile Ile Cys Val Thr
            995                 1000                1005

Leu Gly Ile Asp Val Lys Gly Ala Ala Cys Ala Val Ile Cys Gln Val
    1010                1015                1020

Ser Asn Tyr Phe His Ile Val Ser Gly Ile Leu Ile Glu Phe Ser
1025                1030                1035                1040

Val Asn Val Leu Lys Gly Tyr Ala Cys Ser Leu Arg Gln Arg Ala Lys
                1045                1050                1055

Asp Arg Ala Glu Ser Thr Val Gly Ser Ile Gly Pro Ile Ile Leu Ser
            1060                1065                1070

Gly Pro Val Val Thr Met Ala Gly Ser Thr Met Phe Leu Ser Gly Ala
            1075                1080                1085

His Leu Gln Ile Ile Thr Val Tyr Phe Phe Lys Leu Phe Leu Ile Thr
    1090                1095                1100

Ile Val Ser Ser Ala Val His Ala Leu Ile Ile Leu Pro Ile Leu Leu
1105                1110                1115                1120

Ala Phe Gly Gly Ser Arg Gly His Gly Ser Ser Glu Thr Ser Thr Asn
                1125                1130                1135
```

```
Asp Asn Asp Glu Gln His Asp Ala Cys Val Leu Ser Pro Thr Ala Glu
        1140                1145                1150

Ser His Ile Ser Asn Val Glu Glu Gly Ile Leu Asn Arg Pro Ser Leu
        1155                1160                1165

Leu Asp Ala Ser His Ile Leu Asp Pro Leu Leu Lys Ala Glu Gly Gly
    1170                1175                1180

Ile Asp Lys Ala Ile Gly Arg Asp Phe Lys Tyr His Asn Asn Arg Ser
1185                1190                1195                1200

Leu Leu Pro Ile Tyr Ala Ile Phe Thr Ala Met Tyr Leu Pro Asn Ala
                1205                1210                1215

Lys Ser Ser Tyr Arg Thr Gly Ser Pro Ile Phe Val Asp Thr Asp Leu
        1220                1225                1230

Leu Phe Thr Tyr Ser Ile Pro Tyr Ile His Phe Val Ile Ser Val Ser
        1235                1240                1245

Phe Ile Lys Cys His Val Leu Tyr Ile Tyr Ala Ala Thr Ile Gly Thr
    1250                1255                1260

Leu Val Val Phe Cys His Phe Ser Tyr Thr Ser His Pro Leu Ile Lys
1265                1270                1275                1280

Thr Leu Ser Tyr Phe His Tyr Ser Gln Leu Pro Cys Gly Lys Leu Thr
            1285                1290                1295

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer that
      may be used to amplify the ORF of the human NPC1
      cDNA.

<400> SEQUENCE: 10
atgaccgctc gcggcctggc ccttg                                          25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer that
      may be used to amplify the ORF of the human NPC1
      cDNA.

<400> SEQUENCE: 11
gaaatttaga agccgttcgc gctc                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer that
      may be used to amplify the ORF of the murine NPC1
      cDNA.

<400> SEQUENCE: 12
atgggtgcgc accaccggc cctc                                            24

<210> SEQ ID NO 13
<211> LENGTH: 24
<212> TYPE: DNA
<213> ORGANISM: Artificial Sequence
<220> FEATURE:
```

-continued

```
<223> OTHER INFORMATION: Description of Artificial Sequence: Primer that
      may be used to amplify the ORF of the murine NPC1
      cDNA.

<400> SEQUENCE: 13
aaaattgagg agtcgttctc tctc                                              24
```